(12) United States Patent
Ng et al.

(10) Patent No.: US 11,071,849 B2
(45) Date of Patent: Jul. 27, 2021

(54) CATHETER DEVICES WITH VALVES AND RELATED METHODS

(71) Applicant: B. Braun Melsungen AG, Melsungen (DE)

(72) Inventors: Jarryd Keng Gene Ng, Penang (MY); Boon Ping Neoh, Penang (MY); Chee Mun Phang, Penang (MY); Hang Khiang Chng, Penang (MY); Kevin Woehr, Felsberg (DE)

(73) Assignee: B. Braun Melsungen AG, Melsungen (DE)

( * ) Notice: Subject to any disclaimer, the term of this patent is extended or adjusted under 35 U.S.C. 154(b) by 412 days.

(21) Appl. No.: 15/747,310

(22) PCT Filed: Aug. 18, 2016

(86) PCT No.: PCT/EP2016/069643
§ 371 (c)(1),
(2) Date: Jan. 24, 2018

(87) PCT Pub. No.: WO2017/029374
PCT Pub. Date: Feb. 23, 2017

(65) Prior Publication Data
US 2018/0214673 A1 Aug. 2, 2018

Related U.S. Application Data

(60) Provisional application No. 62/301,917, filed on Mar. 1, 2016, provisional application No. 62/206,481, filed on Aug. 18, 2015.

(51) Int. Cl.
*A61M 25/06* (2006.01)
*A61M 39/06* (2006.01)
*A61B 5/15* (2006.01)

(52) U.S. Cl.
CPC ..... *A61M 25/0606* (2013.01); *A61B 5/15003* (2013.01); *A61M 25/0618* (2013.01);
(Continued)

(58) Field of Classification Search
CPC .......... A61M 25/0606; A61M 25/0618; A61M 39/0613; A61M 39/0693; A61M 25/0693; A61M 2039/062; A61M 2039/064
See application file for complete search history.

(56) References Cited

U.S. PATENT DOCUMENTS 4,387,879 A 6/1983 Tauschinski
4,424,833 A 1/1984 Spector et al.
(Continued)

FOREIGN PATENT DOCUMENTS

CN 101610809 A 12/2009
CN 101808692 A 8/2010
(Continued)

OTHER PUBLICATIONS

Extended European Search Report from the European Patent Office on related EP application (EP19177030.4) dated Jun. 24, 2019.
(Continued)

*Primary Examiner* — Nathan R Price
*Assistant Examiner* — Melissa A Snyder
(74) *Attorney, Agent, or Firm* — Klein, O'Neill & Singh, LLP

(57) ABSTRACT

Needle assemblies and related methods having a needle hub with a needle, a catheter tube with a catheter hub and having the needle extending through the catheter tube in a ready to use position. A valve is positioned in an interior cavity of the catheter hub, the valve having sections that can deflect in a distal direction and sections that can deflect in a proximal direction to open a fluid flow path through the valve. The valve can be deflected by a multi-piece valve opener.

17 Claims, 18 Drawing Sheets

(52) U.S. Cl.
CPC .... *A61M 39/0613* (2013.01); *A61M 39/0693* (2013.01); *A61M 25/0693* (2013.01); *A61M 2039/062* (2013.01); *A61M 2039/064* (2013.01); *A61M 2039/0666* (2013.01); *A61M 2207/00* (2013.01)

(56) References Cited

U.S. PATENT DOCUMENTS

| | | |
|---|---|---|
| 4,436,519 A | 3/1984 | O'Neill |
| 4,512,766 A | 4/1985 | Vailancourt |
| 4,673,393 A | 6/1987 | Suzuki et al. |
| 4,683,916 A | 8/1987 | Raines |
| 4,842,591 A | 6/1989 | Luther |
| 4,874,377 A | 10/1989 | Newgard et al. |
| 4,909,798 A | 3/1990 | Fleischhacker et al. |
| 4,917,668 A | 4/1990 | Haindl |
| 5,053,014 A | 10/1991 | Van Heughten |
| 5,062,836 A | 11/1991 | Wendell |
| 5,064,416 A | 11/1991 | Newgard et al. |
| 5,085,645 A | 2/1992 | Purdy et al. |
| 5,114,408 A | 5/1992 | Fleischhaker et al. |
| 5,134,996 A | 8/1992 | Bell |
| 5,154,703 A | 10/1992 | Bonaldo |
| 5,188,607 A | 2/1993 | Wu |
| 5,234,410 A | 8/1993 | Graham et al. |
| 5,242,393 A | 9/1993 | Brimhall et al. |
| 5,254,098 A | 10/1993 | Ulrich et al. |
| 5,269,763 A | 12/1993 | Boehmer et al. |
| 5,269,768 A | 12/1993 | Cheung |
| 5,300,043 A | 4/1994 | Devlin et al. |
| 5,330,435 A | 7/1994 | Vaillancourt |
| 5,342,315 A | 8/1994 | Rowe et al. |
| 5,349,950 A | 9/1994 | Ulrich et al. |
| 5,350,363 A | 9/1994 | Goode et al. |
| 5,409,461 A | 4/1995 | Steinman |
| 5,419,766 A | 5/1995 | Chang et al. |
| 5,419,769 A | 5/1995 | Devlin et al. |
| 5,429,616 A | 7/1995 | Schaffer |
| 5,456,284 A | 10/1995 | Ryan et al. |
| 5,458,640 A | 10/1995 | Gerrone |
| 5,460,613 A | 10/1995 | Ulrich et al. |
| 5,476,451 A | 12/1995 | Ensminger et al. |
| 5,480,385 A | 1/1996 | Thorne et al. |
| 5,490,503 A | 2/1996 | Hollister |
| 5,501,674 A | 3/1996 | Trombley, III et al. |
| 5,514,116 A | 5/1996 | Vaillancourt et al. |
| 5,531,720 A | 7/1996 | Atkins |
| 5,533,708 A | 7/1996 | Atkinson et al. |
| 5,542,927 A | 8/1996 | Thorne et al. |
| 5,542,933 A | 8/1996 | Marks |
| 5,607,407 A | 3/1997 | Tolkoff et al. |
| 5,611,782 A | 3/1997 | Haedt |
| 5,613,663 A | 3/1997 | Schmidt et al. |
| 5,628,732 A | 5/1997 | Antoon, Jr. et al. |
| 5,685,866 A | 11/1997 | Lopez |
| 5,688,253 A | 11/1997 | Paradis |
| 5,704,914 A | 1/1998 | Stocking et al. |
| 5,727,770 A | 3/1998 | Dennis |
| 5,749,857 A | 5/1998 | Cuppy |
| 5,755,709 A | 5/1998 | Cuppy |
| 5,759,179 A | 6/1998 | Balbierz |
| 5,792,104 A | 8/1998 | Speckman et al. |
| 5,797,880 A | 8/1998 | Erskine |
| 5,800,395 A | 9/1998 | Botich et al. |
| 5,810,835 A | 9/1998 | Ryan et al. |
| 5,817,069 A | 10/1998 | Arnett |
| 5,830,228 A | 11/1998 | Knapp et al. |
| 5,833,662 A | 11/1998 | Stevens |
| 5,843,046 A | 12/1998 | Motisi et al. |
| 5,853,394 A | 12/1998 | Tolkoff et al. |
| 5,858,002 A | 1/1999 | Jesch |
| 5,865,806 A | 2/1999 | Howell |
| 5,911,706 A | 6/1999 | Estabrook et al. |
| 5,911,710 A | 6/1999 | Barry et al. |
| 5,935,110 A | 8/1999 | Brim Hall |
| 5,954,698 A | 9/1999 | Pike |
| 5,968,068 A | 10/1999 | Dehdashtian et al. |
| 5,976,110 A | 11/1999 | Greengrass et al. |
| 6,007,519 A | 12/1999 | Rosselli |
| 6,013,058 A | 1/2000 | Prosl et al. |
| 6,024,727 A | 2/2000 | Thorne et al. |
| 6,024,729 A | 2/2000 | Dehdashtian et al. |
| 6,056,760 A | 5/2000 | Koike et al. |
| 6,074,371 A | 6/2000 | Fischell |
| 6,113,572 A | 9/2000 | Gailey et al. |
| 6,132,402 A | 10/2000 | Tessmann et al. |
| 6,171,287 B1 | 1/2001 | Lynn et al. |
| 6,213,978 B1 | 4/2001 | Voyten |
| 6,217,554 B1 | 4/2001 | Green |
| 6,217,556 B1 | 4/2001 | Ellingson et al. |
| 6,258,065 B1 | 7/2001 | Dennis et al. |
| 6,299,602 B1 | 10/2001 | Miller et al. |
| 6,352,520 B1 | 3/2002 | Miyazaki |
| 6,371,963 B1 | 4/2002 | Nishtala et al. |
| 6,379,337 B1 | 4/2002 | Mohammad |
| 6,482,186 B1 | 11/2002 | Douglas et al. |
| 6,485,473 B1 | 11/2002 | Lynn |
| 6,506,181 B2 | 1/2003 | Meng et al. |
| 6,533,759 B1 | 3/2003 | Watson et al. |
| 6,544,235 B2 | 4/2003 | Motisi et al. |
| 6,610,045 B2 | 8/2003 | Chavez et al. |
| 6,616,630 B1 | 9/2003 | Woehr et al. |
| 6,620,136 B1 | 9/2003 | Pressley, Sr. et al. |
| 6,699,221 B2 | 3/2004 | Vaillancourt |
| 6,719,726 B2 | 4/2004 | Meng et al. |
| 6,740,063 B2 | 5/2004 | Lynn |
| 6,746,420 B1 | 6/2004 | Prestidge et al. |
| 6,764,468 B1 | 7/2004 | East |
| 6,860,869 B2 | 3/2005 | Dennis |
| 6,921,386 B2 | 7/2005 | Shue et al. |
| 6,921,391 B1 | 7/2005 | Barker et al. |
| 6,981,969 B2 | 1/2006 | Chavez et al. |
| 7,008,404 B2 | 3/2006 | Nakajima |
| 7,048,729 B2 | 5/2006 | Meglin et al. |
| 7,052,507 B2 | 5/2006 | Wakuda et al. |
| 7,120,487 B2 | 10/2006 | Nelson |
| 7,125,396 B2 | 10/2006 | Leinsing et al. |
| 7,156,827 B2 | 1/2007 | McNary et al. |
| 7,214,215 B2 | 5/2007 | Heinzerling et al. |
| 7,270,649 B2 | 9/2007 | Fitzgerald |
| 7,311,708 B2 | 12/2007 | McClurken |
| 7,347,839 B2 | 3/2008 | Hiejima |
| 7,470,254 B2 | 12/2008 | Basta et al. |
| 7,537,595 B2 | 5/2009 | McClurken |
| 7,625,346 B2 | 12/2009 | Grigoryants et al. |
| 7,632,243 B2 | 12/2009 | Bialecki et al. |
| 7,632,262 B2 | 12/2009 | Bates |
| 7,635,357 B2 | 12/2009 | Mayer |
| 7,641,669 B2 | 1/2010 | Roychowdhury et al. |
| 7,666,166 B1 | 2/2010 | Emmert et al. |
| 7,670,317 B2 | 3/2010 | Cindrich et al. |
| 7,670,322 B2 | 3/2010 | Fangrow, Jr. |
| 7,691,093 B2 | 4/2010 | Brimhall |
| 7,695,458 B2 | 4/2010 | Belley et al. |
| 7,713,257 B2 | 5/2010 | Brimhall et al. |
| 7,736,337 B2 | 6/2010 | Diep et al. |
| 7,736,339 B2 | 6/2010 | Woehr et al. |
| 7,758,514 B2 | 7/2010 | Grigoryants et al. |
| 7,789,861 B2 | 9/2010 | Franer |
| 7,806,869 B2 | 10/2010 | Nilsson et al. |
| 7,914,494 B2 | 3/2011 | Hiejima |
| 7,914,496 B2 | 3/2011 | Brockmeier et al. |
| 7,955,346 B2 | 6/2011 | Mauch et al. |
| 8,002,750 B2 | 8/2011 | Smith |
| 8,006,953 B2 | 8/2011 | Bennett |
| 8,029,472 B2 | 10/2011 | Leinsing et al. |
| 8,042,689 B2 | 10/2011 | Fröjd et al. |
| 8,048,039 B2 | 11/2011 | Carlyon et al. |
| 8,056,756 B2 | 11/2011 | Okiyama |
| 8,066,670 B2 | 11/2011 | Cluff et al. |
| 8,066,675 B2 | 11/2011 | Cindrich et al. |
| 8,123,727 B2 | 2/2012 | Luther et al. |
| 8,147,413 B2 | 4/2012 | Abraham |
| 8,147,455 B2 | 4/2012 | Butts et al. |

(56) References Cited

U.S. PATENT DOCUMENTS

| | | |
|---|---|---|
| 8,152,755 B1 | 4/2012 | Wach et al. |
| 8,172,757 B2 | 5/2012 | Jaffe et al. |
| 8,202,253 B1 | 6/2012 | Wexler |
| 8,206,357 B2 | 6/2012 | Bettuchi |
| 8,206,375 B2 | 6/2012 | Snow |
| 8,257,313 B2 | 9/2012 | McKinnon et al. |
| 8,257,339 B1 | 9/2012 | Rosado |
| 8,262,623 B2 | 9/2012 | Nijland et al. |
| 8,286,657 B2 | 10/2012 | Belley et al. |
| 8,308,655 B2 | 11/2012 | Grigoryants et al. |
| 8,308,691 B2 | 11/2012 | Woehr et al. |
| 8,323,249 B2 | 12/2012 | White et al. |
| 8,328,762 B2 | 12/2012 | Woehr et al. |
| 8,333,735 B2 | 12/2012 | Woehr et al. |
| 8,337,463 B2 | 12/2012 | Woehr et al. |
| 8,348,844 B2 | 1/2013 | Kunjan et al. |
| 8,361,038 B2 | 1/2013 | McKinnon et al. |
| 8,366,684 B2 | 2/2013 | Harding |
| 8,388,583 B2 | 3/2013 | Stout et al. |
| 8,419,688 B2 | 4/2013 | Woehr et al. |
| 8,454,579 B2 | 6/2013 | Fangrow, Jr. |
| 8,460,247 B2 | 6/2013 | Woehr et al. |
| 8,465,461 B2 | 6/2013 | Wu et al. |
| 8,469,928 B2 | 6/2013 | Stout et al. |
| 8,470,025 B2 | 6/2013 | Lenihan et al. |
| 8,506,533 B2 | 8/2013 | Carlyon et al. |
| 8,506,534 B2 | 8/2013 | Luther et al. |
| 8,518,013 B2 | 8/2013 | Kurrus et al. |
| 8,535,271 B2 | 9/2013 | Fuchs et al. |
| 8,540,728 B2 | 9/2013 | Woehr et al. |
| 8,562,520 B2 | 10/2013 | Rockrohr |
| 8,585,651 B2 | 11/2013 | Asai |
| 8,591,468 B2 | 11/2013 | Woehr et al. |
| 8,597,249 B2 | 12/2013 | Woehr et al. |
| 8,597,252 B2 | 12/2013 | Burkholz et al. |
| 8,608,727 B2 | 12/2013 | Michels et al. |
| 8,608,728 B2 | 12/2013 | Michels et al. |
| 8,622,972 B2 | 1/2014 | Nystrom et al. |
| 8,628,056 B2 | 1/2014 | LaBean et al. |
| 8,636,695 B2 | 1/2014 | Cluff et al. |
| 8,641,675 B2 | 2/2014 | Stout et al. |
| 8,641,676 B2 | 2/2014 | Butts et al. |
| 8,647,301 B2 | 2/2014 | Bialecki et al. |
| 8,652,104 B2 | 2/2014 | Goral et al. |
| 8,663,169 B2 | 3/2014 | Emmert et al. |
| 8,668,674 B2 | 3/2014 | White et al. |
| 8,679,063 B2 | 3/2014 | Stout et al. |
| 8,690,815 B2 | 4/2014 | Porter et al. |
| 8,690,833 B2 | 4/2014 | Belson |
| 8,715,242 B2 | 5/2014 | Helm, Jr. |
| 8,728,030 B2 | 5/2014 | Woehr |
| 8,740,850 B2 | 6/2014 | Leinsing et al. |
| 8,771,230 B2 | 7/2014 | White et al. |
| 8,790,310 B2 | 7/2014 | White et al. |
| 8,831,707 B2 | 9/2014 | Tekulve et al. |
| 8,864,715 B2 | 10/2014 | Cluff et al. |
| 8,882,742 B2 | 11/2014 | Dikeman et al. |
| 8,926,494 B1 | 1/2015 | Cook et al. |
| 8,932,257 B2 | 1/2015 | Woehr |
| 8,932,258 B2 | 1/2015 | Blanchard et al. |
| 8,932,259 B2 | 1/2015 | Stout et al. |
| 8,939,938 B2 | 1/2015 | Funamura et al. |
| 8,968,252 B2 | 3/2015 | White et al. |
| 8,979,802 B2 | 3/2015 | Woehr |
| 8,998,852 B2 | 4/2015 | Blanchard et al. |
| 9,011,382 B2 | 4/2015 | Nilsson et al. |
| 9,028,393 B2 | 5/2015 | Farnan |
| 9,089,671 B2 | 7/2015 | Stout et al. |
| 9,095,679 B2 | 8/2015 | Nishimura et al. |
| 9,108,021 B2 | 8/2015 | Hyer et al. |
| 9,114,231 B2 | 8/2015 | Woehr et al. |
| 9,114,241 B2 | 8/2015 | Stout et al. |
| 9,149,625 B2 | 10/2015 | Woehr et al. |
| 9,149,626 B2 | 10/2015 | Woehr et al. |
| 9,155,863 B2 | 10/2015 | Isaacson et al. |
| 9,155,864 B2 | 10/2015 | Stout et al. |
| 9,180,275 B2 | 11/2015 | Helm |
| 9,186,455 B2 | 11/2015 | Moyer |
| 9,220,833 B2 | 12/2015 | Robert et al. |
| 9,227,038 B2 | 1/2016 | Woehr |
| 9,227,047 B2 | 1/2016 | Khalaj |
| RE45,896 E | 2/2016 | Stout et al. |
| 9,272,088 B2 | 3/2016 | Bornhoft |
| 9,314,201 B2 | 4/2016 | Burkholz et al. |
| 9,320,870 B2 | 4/2016 | Woehr |
| 9,327,095 B2 | 5/2016 | Ma |
| 9,352,119 B2 | 5/2016 | Burkholz et al. |
| 9,370,641 B2 | 6/2016 | Woehr et al. |
| 9,381,320 B2 | 7/2016 | Vincent et al. |
| 9,381,324 B2 | 7/2016 | Fuchs et al. |
| 9,399,116 B2 | 7/2016 | Goral et al. |
| 9,427,549 B2 | 8/2016 | Wooehr et al. |
| 9,545,632 B2 | 1/2017 | Lentz et al. |
| 9,579,486 B2 | 2/2017 | Burkholz et al. |
| 9,592,366 B2 | 3/2017 | White et al. |
| 9,623,210 B2 | 4/2017 | Woehr |
| 9,737,252 B2 | 8/2017 | Teoh et al. |
| 9,750,920 B2 | 9/2017 | Vincent et al. |
| 9,764,085 B2 | 9/2017 | Teoh |
| 9,844,648 B2 | 12/2017 | Nakajima et al. |
| 9,919,136 B2 | 3/2018 | Lim et al. |
| 9,962,525 B2 | 5/2018 | Woehr |
| 10,004,891 B2 | 6/2018 | Woehr |
| 10,080,869 B2 | 9/2018 | Woehr et al. |
| 10,166,370 B2 | 1/2019 | Woehr et al. |
| 10,173,002 B2 | 1/2019 | Tan et al. |
| 10,207,081 B2 | 2/2019 | Fuchs et al. |
| 10,286,185 B2 | 5/2019 | Tanabe et al. |
| 10,376,686 B2 | 8/2019 | Burkholz et al. |
| 10,449,331 B2 | 10/2019 | Lim et al. |
| 10,456,572 B2 | 10/2019 | Woehr |
| 10,463,395 B2 | 11/2019 | Reid et al. |
| 10,463,839 B2 | 11/2019 | Woehr |
| 10,493,262 B2 | 12/2019 | Tran et al. |
| 10,500,376 B2 | 12/2019 | Isaacson et al. |
| 10,543,343 B2 | 1/2020 | Woehr et al. |
| 10,549,072 B2 | 2/2020 | Burkholz et al. |
| 10,646,253 B2 | 5/2020 | Blanc |
| 2001/0053895 A1 | 12/2001 | Vaillancourt |
| 2002/0128604 A1 | 9/2002 | Nakajima |
| 2004/0210194 A1 | 10/2004 | Bonnette et al. |
| 2005/0256500 A1 | 11/2005 | Fujii |
| 2006/0118749 A1 | 6/2006 | Ryan et al. |
| 2006/0155245 A1* | 7/2006 | Woehr .............. A61M 39/0693 604/164.08 |
| 2007/0083162 A1 | 4/2007 | O'Reagan et al. |
| 2007/0225647 A1 | 9/2007 | Luther et al. |
| 2007/0233007 A1 | 10/2007 | Adams |
| 2008/0058720 A1 | 3/2008 | Spohn et al. |
| 2008/0108944 A1 | 5/2008 | Woehr et al. |
| 2008/0108976 A1 | 5/2008 | Johnson et al. |
| 2009/0221975 A1 | 9/2009 | Rodd |
| 2010/0179480 A1 | 7/2010 | Sugiki et al. |
| 2010/0185153 A1 | 7/2010 | Sugiki et al. |
| 2010/0204648 A1 | 8/2010 | Stout et al. |
| 2010/0280456 A1 | 11/2010 | Nijland et al. |
| 2011/0054406 A1 | 3/2011 | McKinnon |
| 2011/0282286 A1 | 11/2011 | Argentine |
| 2011/0301553 A1 | 12/2011 | Goral et al. |
| 2011/0319825 A1 | 12/2011 | Goral et al. |
| 2011/0319838 A1 | 12/2011 | Goral et al. |
| 2012/0016266 A1 | 1/2012 | Burkholz |
| 2012/0089101 A1 | 4/2012 | Carlyon et al. |
| 2012/0259293 A1 | 10/2012 | Bialecki et al. |
| 2012/0271235 A1* | 10/2012 | Fuchs ................ A61M 5/1626 604/164.08 |
| 2012/0330238 A1 | 12/2012 | Robert et al. |
| 2013/0006223 A1 | 1/2013 | Michels et al. |
| 2013/0165868 A1 | 6/2013 | Isaacson et al. |
| 2013/0204226 A1 | 8/2013 | Keyser |
| 2013/0304026 A1 | 11/2013 | Luther et al. |
| 2014/0052065 A1 | 2/2014 | Woehr et al. |
| 2014/0107619 A1 | 4/2014 | Butts et al. |
| 2014/0135702 A1 | 5/2014 | Woehr et al. |

(56) References Cited

U.S. PATENT DOCUMENTS

| | | | |
|---|---|---|---|
| 2014/0228775 A1 | 8/2014 | Burkholz et al. | |
| 2014/0276453 A1 | 9/2014 | Woehr | |
| 2014/0276462 A1* | 9/2014 | Vincent | A61M 25/0097 604/256 |
| 2014/0288500 A1 | 9/2014 | Leinsing et al. | |
| 2015/0038909 A1 | 2/2015 | Christensen et al. | |
| 2015/0038910 A1 | 2/2015 | Harding et al. | |
| 2015/0088095 A1 | 3/2015 | Luther et al. | |
| 2015/0151085 A1 | 6/2015 | Tan et al. | |
| 2015/0151088 A1 | 6/2015 | Lim et al. | |
| 2015/0190570 A1 | 7/2015 | Teoh | |
| 2015/0335858 A1 | 11/2015 | Woehr et al. | |
| 2015/0335864 A1 | 11/2015 | Knutsson | |
| 2016/0008580 A1 | 1/2016 | Woehr et al. | |
| 2016/0114136 A1 | 4/2016 | Woehr | |
| 2016/0114137 A1 | 4/2016 | Woehr et al. | |
| 2016/0296724 A1 | 10/2016 | Goral et al. | |
| 2017/0035992 A1 | 2/2017 | Harding et al. | |
| 2017/0173304 A1 | 6/2017 | Teoh | |
| 2017/0326341 A1 | 11/2017 | Liska | |
| 2018/0093077 A1 | 4/2018 | Harding et al. | |
| 2018/0361119 A1 | 12/2018 | Goral et al. | |
| 2018/0361120 A1 | 12/2018 | Goral et al. | |
| 2019/0038870 A1 | 2/2019 | Isaacson et al. | |
| 2019/0076625 A1 | 3/2019 | White et al. | |
| 2019/0160264 A1 | 5/2019 | Isaacson | |

FOREIGN PATENT DOCUMENTS

| | | |
|---|---|---|
| CN | 203724591 U | 7/2014 |
| CN | 203763665 U | 8/2014 |
| CN | 104039384 A | 9/2014 |
| CN | 104043167 A | 9/2014 |
| CN | 104415446 A | 3/2015 |
| CN | 105407959 A | 3/2016 |
| EP | 0875262 A2 | 11/1998 |
| EP | 1911485 A1 | 4/2008 |
| EP | 2213328 A1 | 8/2010 |
| EP | 3097939 A1 | 11/2016 |
| EP | 3337549 B1 | 6/2019 |
| FR | 2829396 A1 | 3/2003 |
| JP | H05-028348 U | 4/1993 |
| JP | H06-304250 A | 11/1994 |
| JP | H7-136285 A | 5/1995 |
| JP | H11-004894 A | 1/1999 |
| JP | H11-299898 A | 11/1999 |
| JP | 2005-531377 A | 10/2005 |
| JP | 2010-508905 A1 | 3/2010 |
| JP | 2012-525877 A | 10/2012 |
| JP | 2013-533023 A | 8/2013 |
| JP | 2014-528807 A | 10/2014 |
| JP | 2016-509916 A | 4/2016 |
| RU | 2009120995 A | 12/2010 |
| RU | 2477639 C2 | 3/2013 |
| WO | WO 2010/093791 A1 | 8/2010 |
| WO | WO 2009/041522 A1 | 1/2011 |
| WO | WO 2009/041523 A1 | 1/2011 |
| WO | WO 2013/052668 A1 | 4/2013 |
| WO | WO 2014/140265 A1 | 9/2014 |
| WO | WO 2015/104336 A1 | 7/2015 |
| WO | WO 2015/161294 A1 | 10/2015 |
| WO | WO 2018/033626 A1 | 2/2018 |
| WO | WO 2018/077748 A1 | 5/2018 |

OTHER PUBLICATIONS

International Preliminary Report on Patentability (Chapter I) on related PCT application (PCT/EP2017/070934) from International Searching Authority (EPO) dated Feb. 28, 2019.
International Preliminary Report on Patentability on corresponding PCT application (PCT/EP2016/069643) from International Searching Authority (EPO) dated Mar. 1, 2018.
International Preliminary Report on Patentability on related PCT application (PCT/EP 2016/069619) from International Searching Authority (EPO) dated Mar. 1, 2018.
Office Action on corresponding foreign application (JP Application No. 2018-508169) from the Japanese Patent Office dated Oct. 1, 2019.
Decision to Grant on corresponding foreign application (RU Application No. 2018109391/14) from the Russian Patent Office dated Oct. 14, 2019.
International Search Report & Written Opinion on related PCT application (PCT/EP2016/069643) from International Searching Authority (EPO) dated Nov. 16, 2016.
International Search Report & Written Opinion on corresponding PCT application (PCT/EP 2016/069619) from International Searching Authority (EPO) dated Dec. 8, 2016.
International Search Report & Written Opinion on related PCT application (PCT/EP2014/055089) from International Searching Authority (EPO) dated Jul. 17, 2014.
International Search Report & Written Opinion on related PCT application (PCT/EP2017/070934) from International Searching Authority (EPO) dated Oct. 25, 2017.
Non-Final Office Action on related US application (U.S. Appl. No. 14/012,568) dated Aug. 8, 2014.
Final Office Action on related US application (U.S. Appl. No. 14/012,568) dated Dec. 2, 2014.
Non-Final Office Action on related US application (U.S. Appl. No. 14/818,687) dated Feb. 10, 2016.
Office Action on related foreign application (JP Application No. 2018-508170) from the Japanese Patent Office dated Jun. 23, 2020.
Office Action including Search Report on corresponding foreign application (CN Application No. 201680048610.6) from the National Intellectual Property Administration, P.R. China dated Mar. 27, 2020.
Office Action including Search Report on corresponding foreign application (CN Application No. 201680048615.9) from the National Intellectual Property Administration, P.R. China dated Mar. 30, 2020.
Examination Report on corresponding foreign application (AU Application No. 2016309744) from the IP Australia dated May 6, 2020.
Preliminary Office Action on corresponding foreign application (BR Application No. 11 2018 002976-9) from the Brazilian Intellectual Property Office dated May 6, 2020.
Office Action on related foreign application (AU Application No. 2016309744) from the Australian Patent Office dated Aug. 31, 2020.
Office Action on related foreign application (CN Application No. 201310650219.1) from the Chinese Intellectual Property Office dated Feb. 13, 2018.
Office Action on related foreign application (CN Application No. 201310650219.1) from the Chinese Intellectual Property Office dated Oct. 24, 2018.
Extended European Search Report from European Patent Office on related EP application (EP 20172492.9) dated Nov. 5, 2020.
Office Action on related foreign application (JP Application No. 2015-562191) from the Japanese Patent Office dated Apr. 25, 2017.
Office Action on related foreign application (JP Application No. 2015-562191) from the Japanese Patent Office dated Oct. 17, 2017.
Office Action on related foreign application (MX Application No. MX/a/2018/001987) from the Mexican Institute of Industrial Property (IMPI) dated Dec. 8, 2020.
International Preliminary Report on Patentability on corresponding PCT application (PCT/EP2014/055089) from International Searching Authority (EPO) dated Apr. 10, 2015.
International Search Report and Written Opinion on corresponding PCT application (PCT/EP2019/085732) from International Searching Authority (EPO) dated Apr. 28, 2020.
Supplementary Examination Report on related foreign application (SG Application No. 11201506983W) from the Singaporean Intellectual Property Office dated Jan. 29, 2016.
Office Action on related foreign application (MX Application No. MX/a/2018/001987) from the Mexican Patent Office dated Jul. 23, 2020.

(56) References Cited

OTHER PUBLICATIONS

Office Action on related foreign application (JP Application No. 2018-508169) from the Japanese Patent Office dated Aug. 4, 2020.
Office Action on related foreign application (CN Application No. 201780064583.6) from the National Intellectual Property Administration, P.R. China dated Jan. 27, 2021.
Office Action on related foreign application (CN Application No. 201680048610.6) from the National Intellectual Property Administration, P.R. China dated Feb. 20, 2021.
Office Action on related foreign application (JP Application No. 2018-508170) from the Japan Patent Office dated Mar. 2, 2021.
First Examination Report on related foreign application (IN Application No. 201817000337) from the Indian Patent Office dated May 18, 2021.
Office Action on related foreign application (JP Application No. 2019-508949) from the Japan Patent Office dated May 11, 2021.
Substantive Examination Adverse Report on related foreign application (MY Application No. PI 2018700453) from the Malaysian Patent Office dated May 12, 2021.
Non-Final Office Action on related US application (U.S. Appl. No. 16/323,379) dated May 17, 2021.
Preliminary Office Action on related foreign application (BR Application No. 12 2019 017170-0) from the Brazilian Patent Office dated Apr. 7, 2021.
Office Action on related foreign application (CN Application No. 201680048615.9) from the National Intellectual Property Administration, P.R. China dated Mar. 9, 2021.

\* cited by examiner

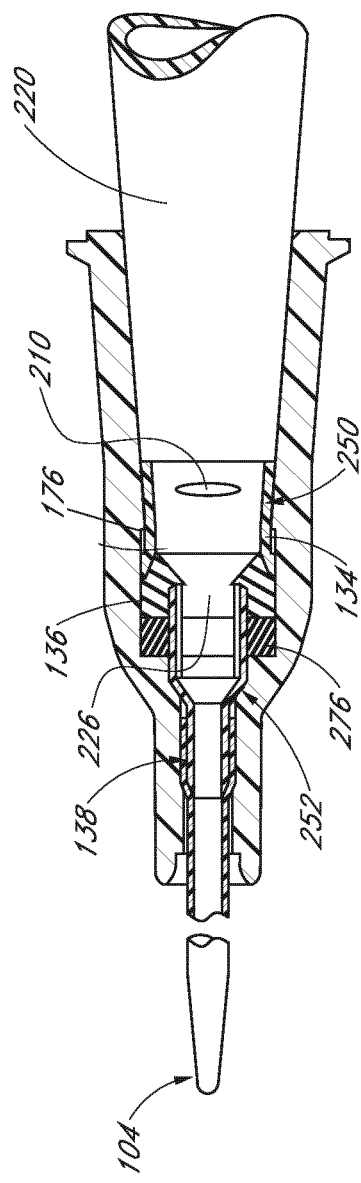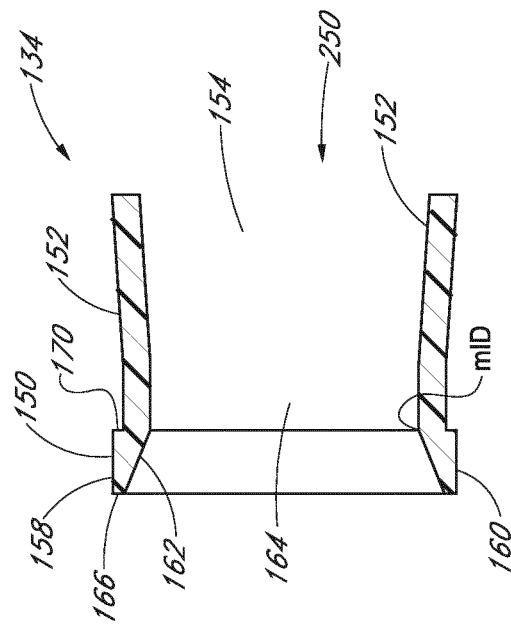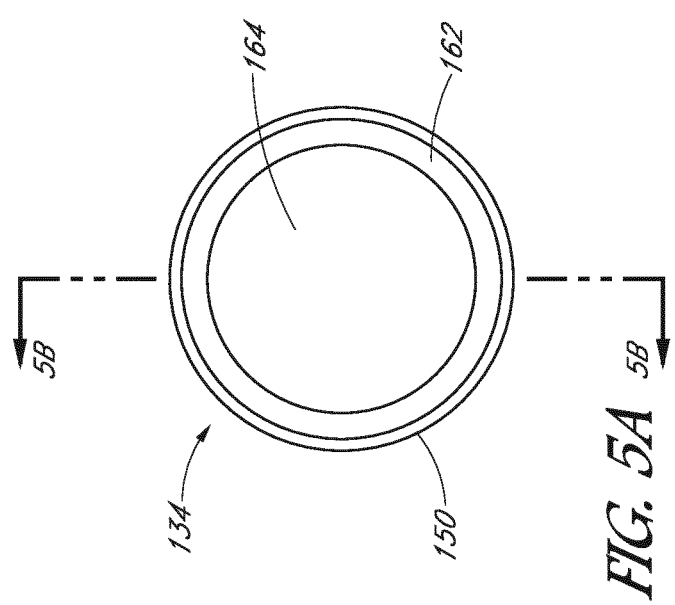

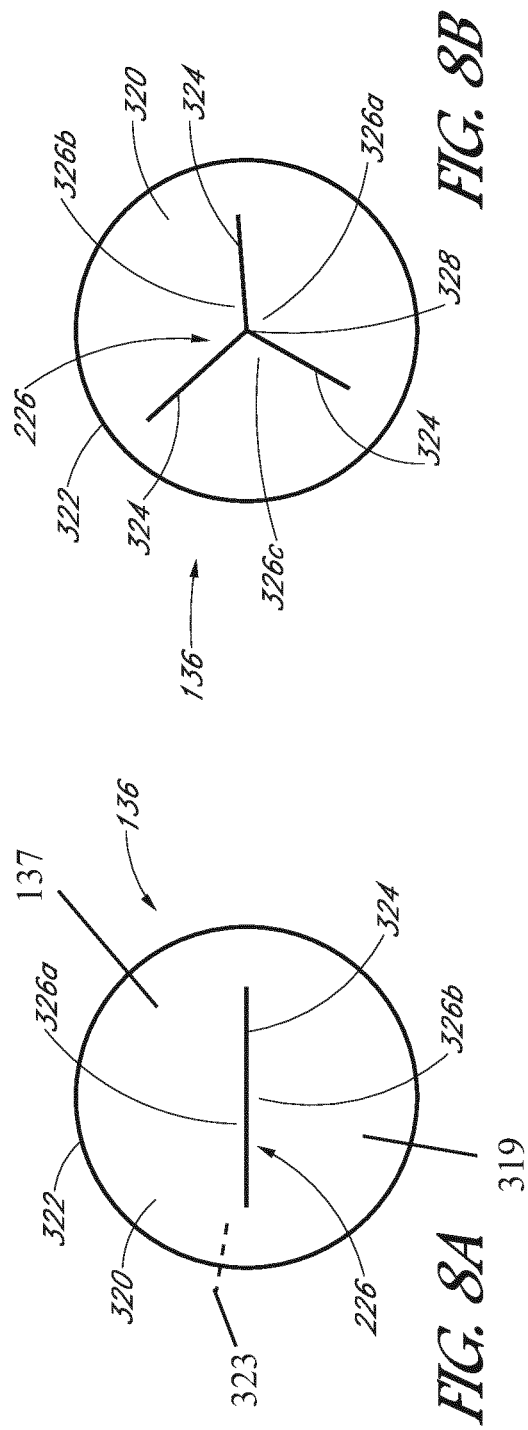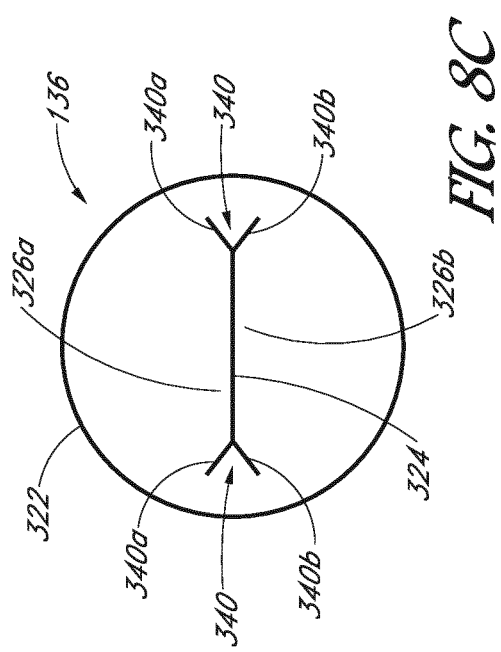

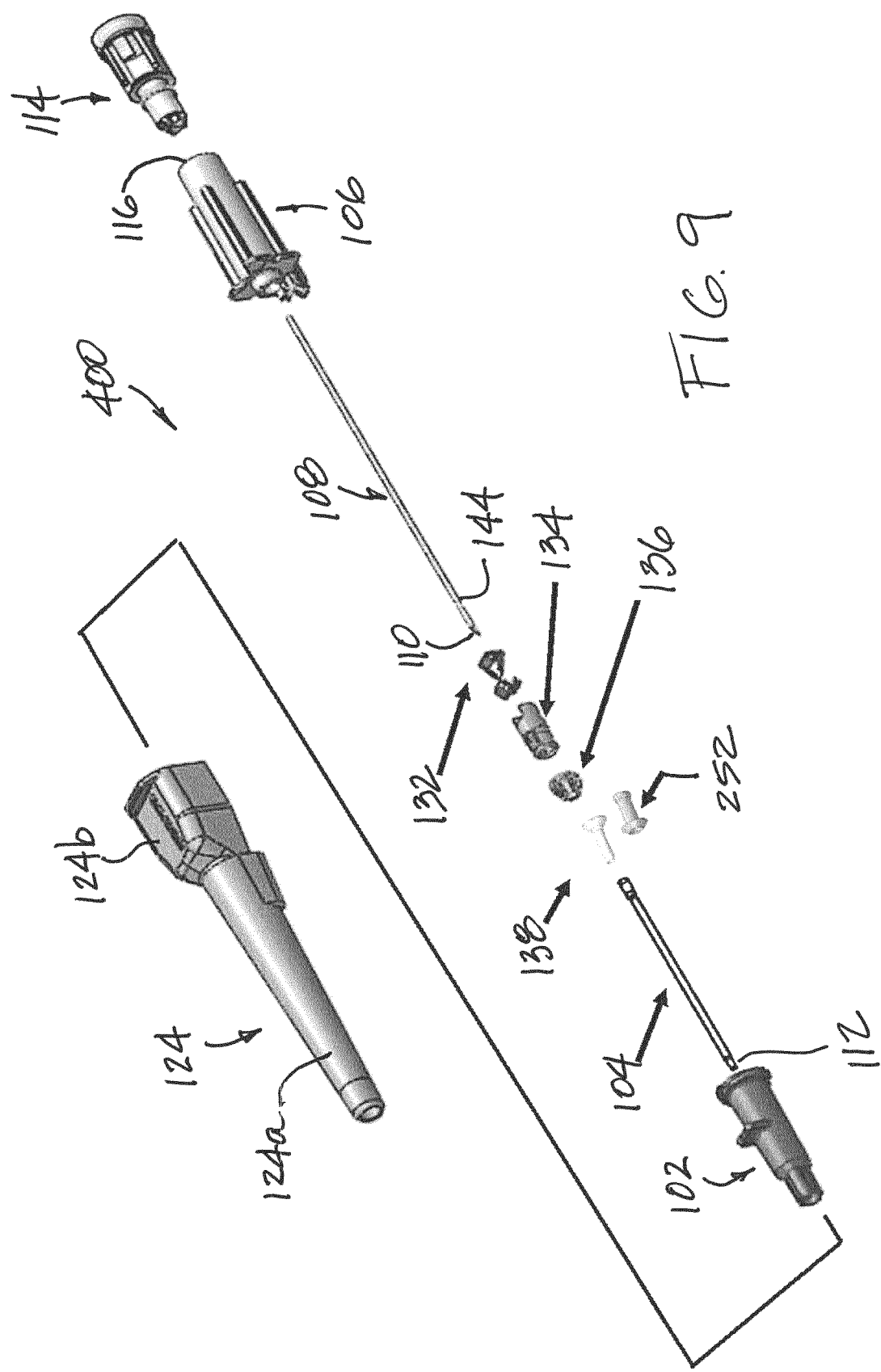

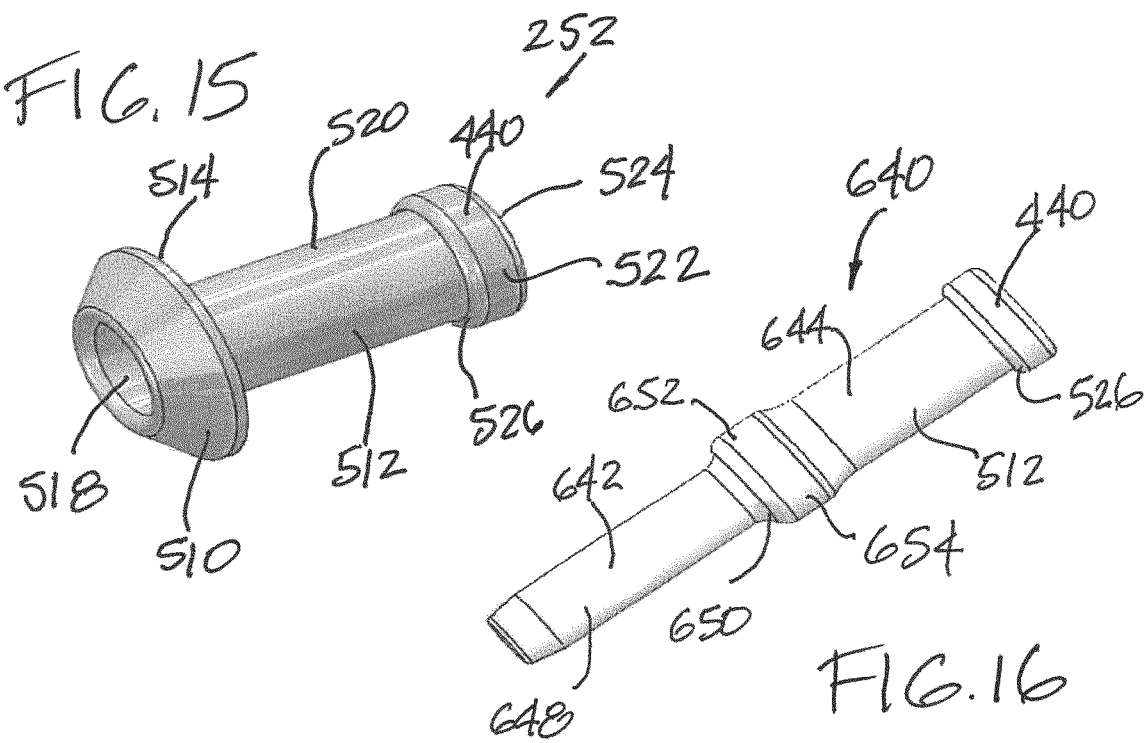
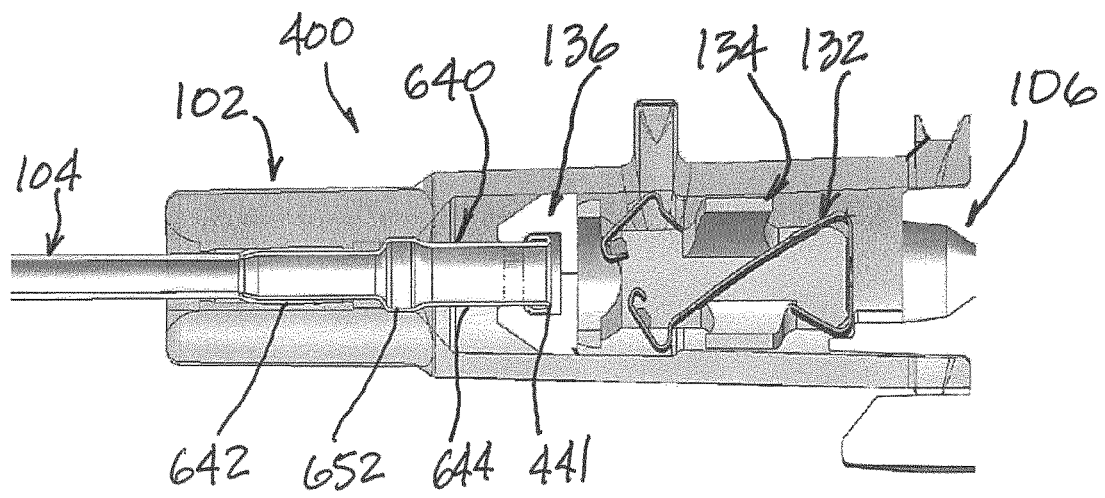

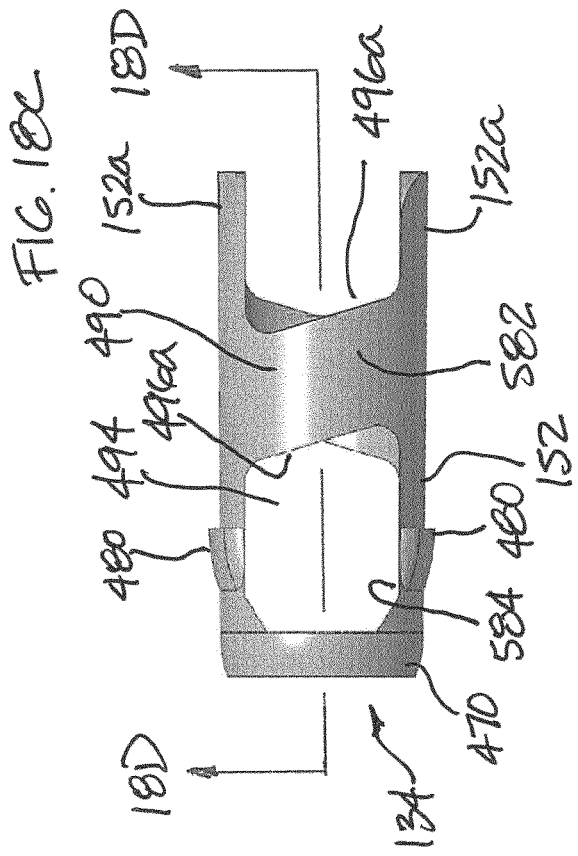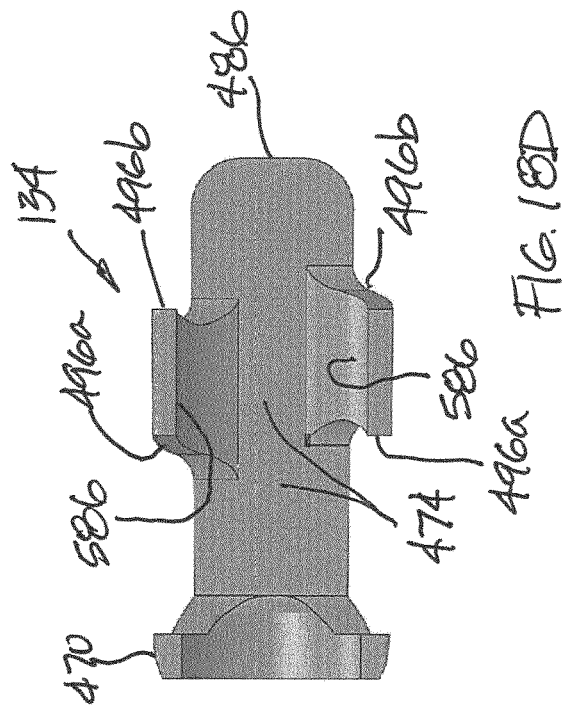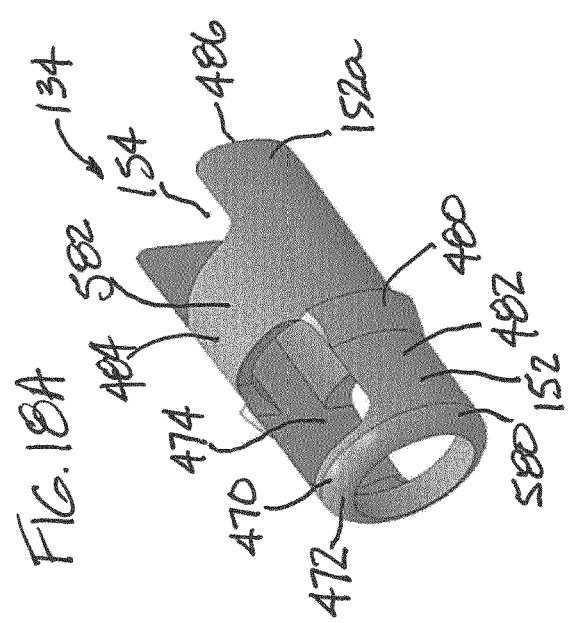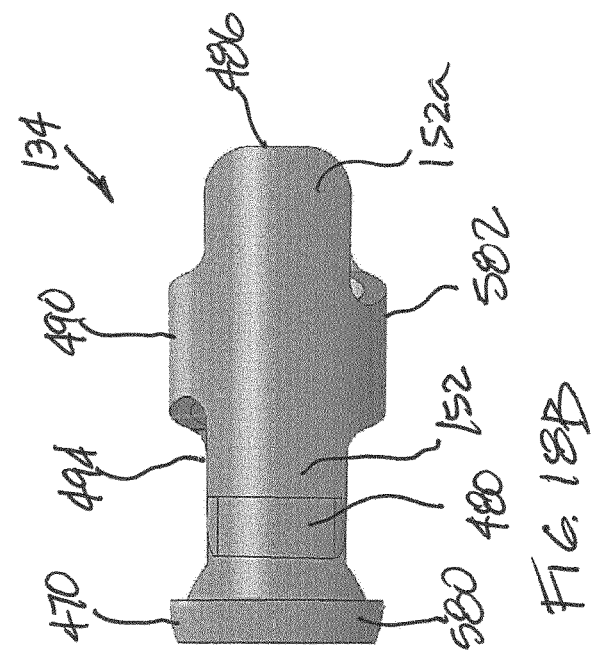

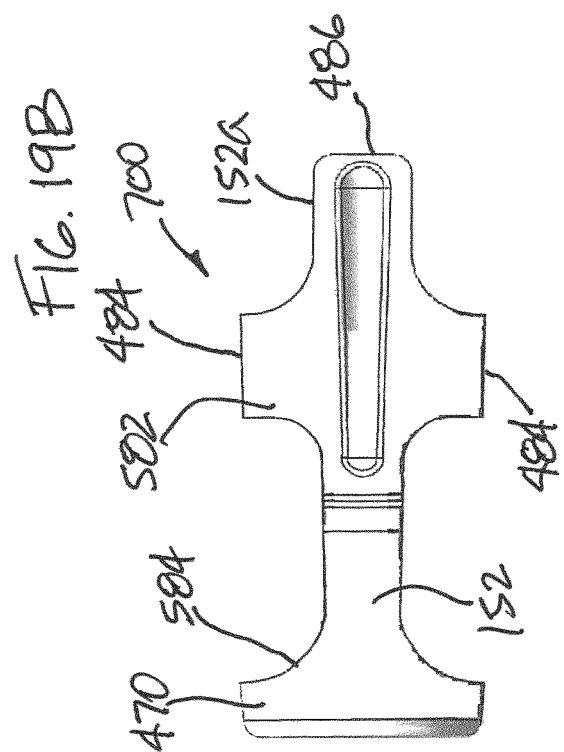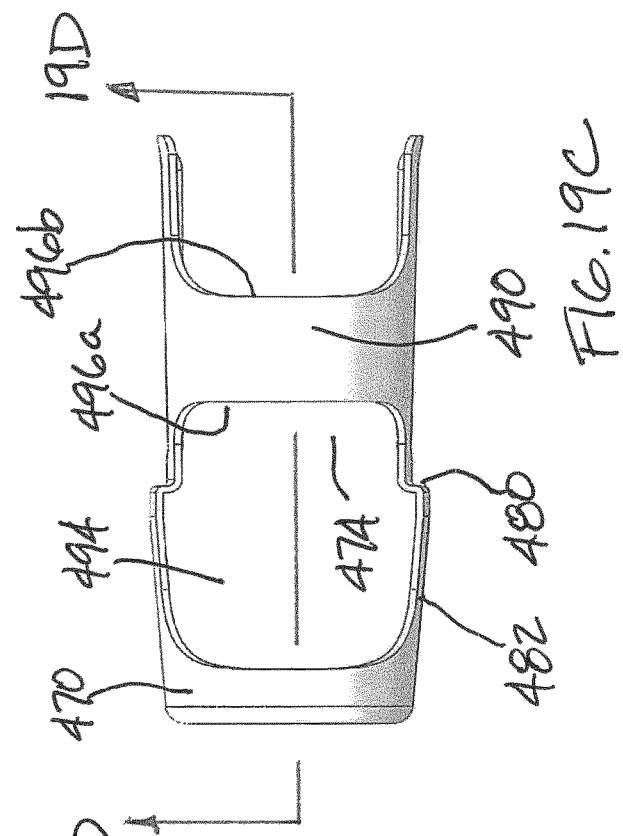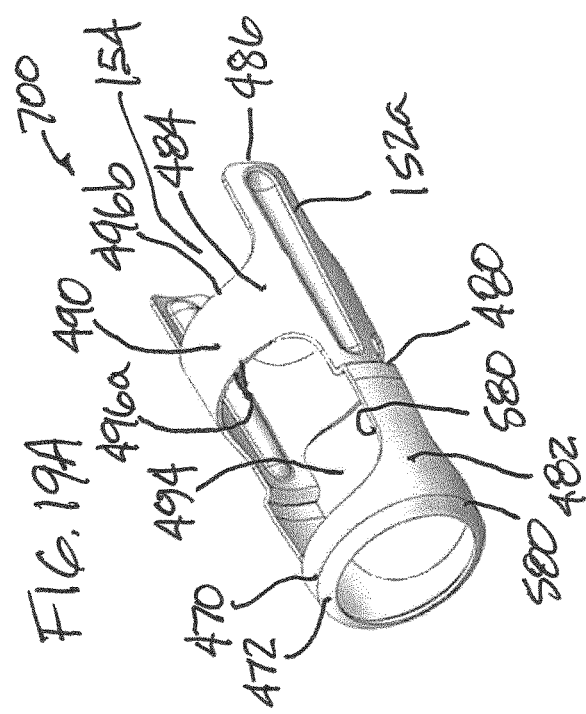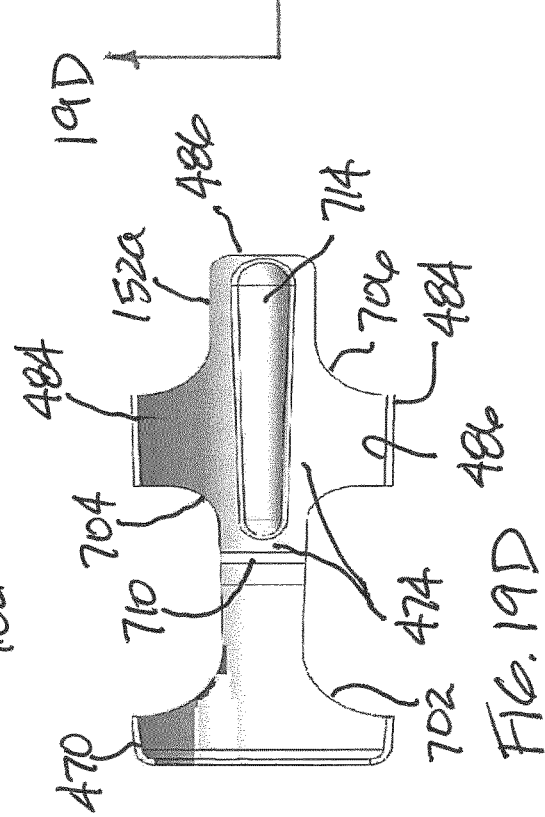

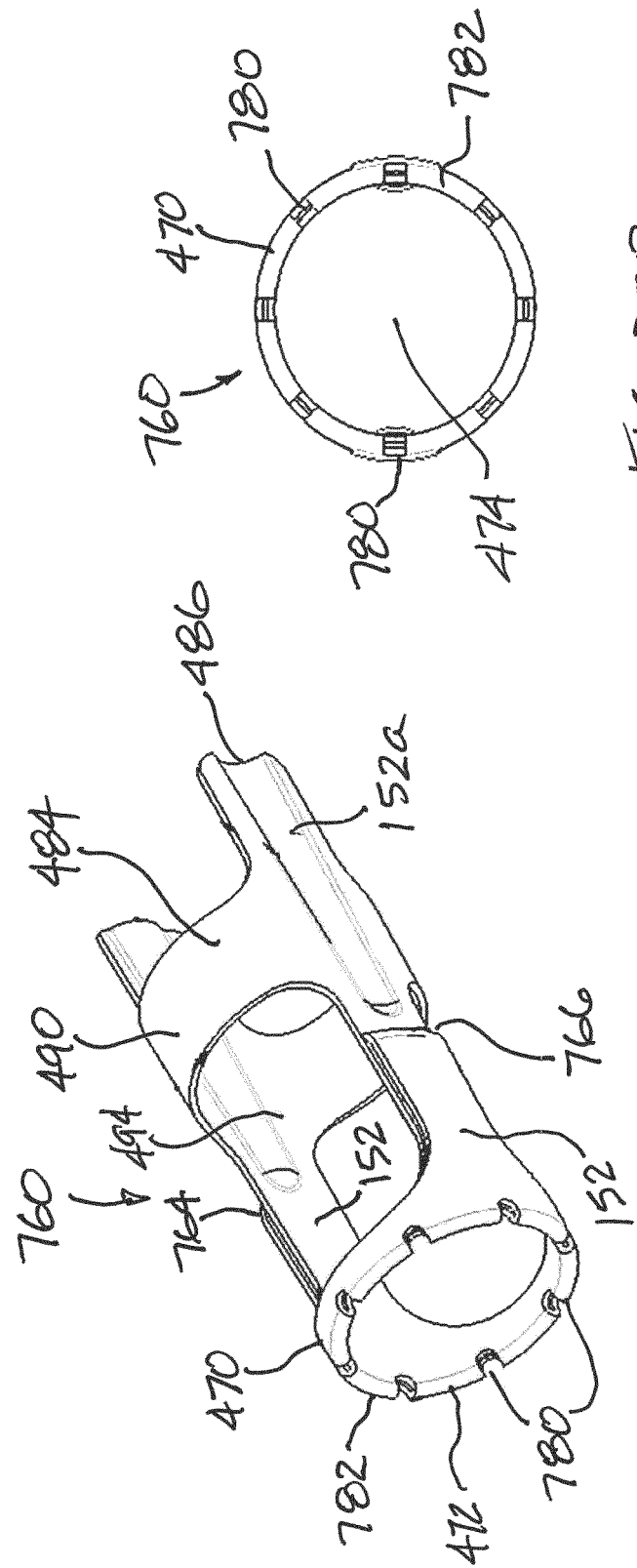

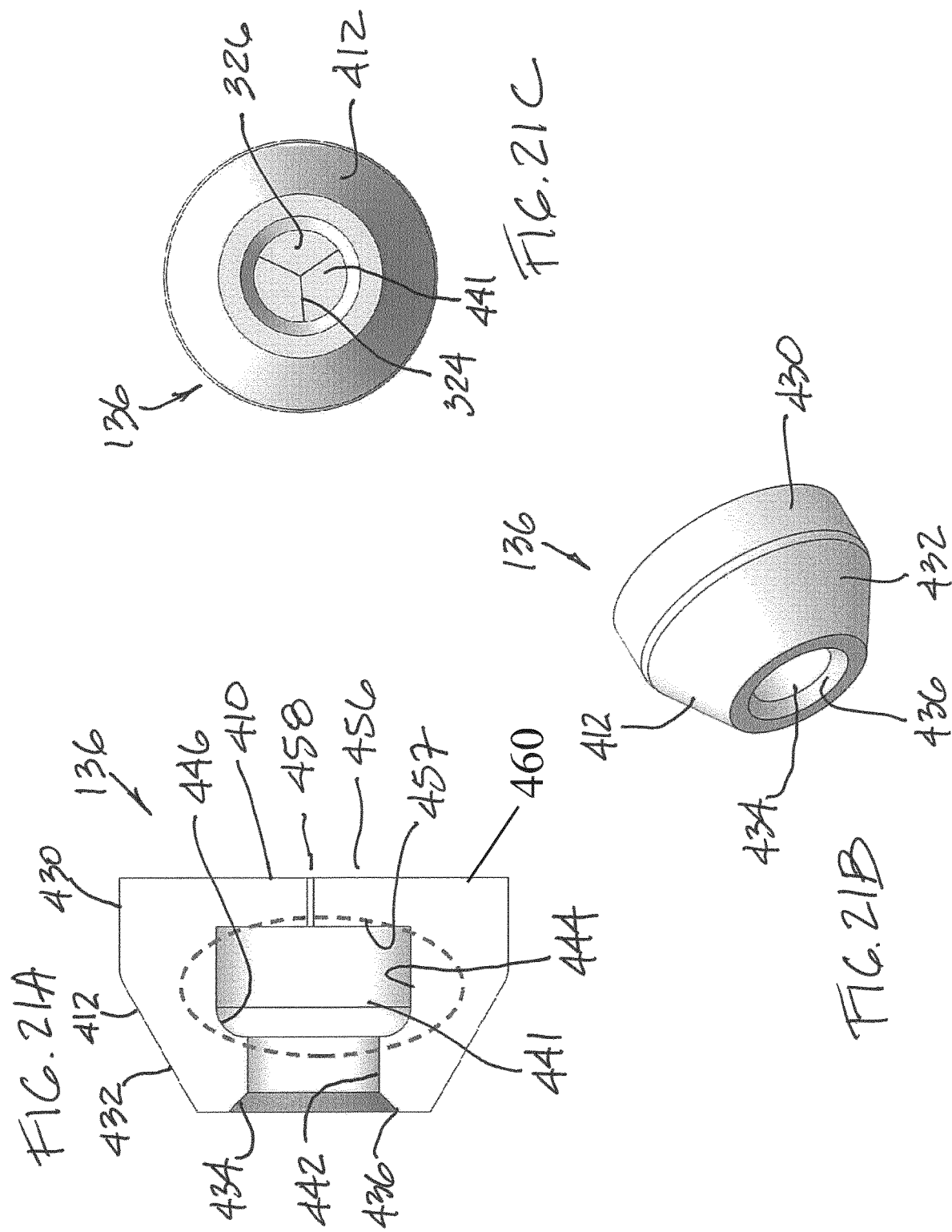

CATHETER DEVICES WITH VALVES AND RELATED METHODS

FIELD OF ART

The disclosed invention generally relates to needle devices and intravenous (IV) infusion devices, including IV catheters. In particular, IV catheter assemblies having a valve and a valve actuator for opening the valve are disclosed.

BACKGROUND

IV catheters are commonly used for a variety of infusion therapies, including infusing fluids into a patient, withdrawing blood from a patient, or monitoring various parameters of the patient's vascular system. Catheters are typically connected to a catheter adapter that accommodates the attachment of IV tubing to the catheter. Blood control catheters include an internal blood control valve that is opened by the insertion of a male Luer or other object into a proximal end of the catheter adapter. Non-limiting examples of blood control valves are disclosed in United States Patent Application Publication No. 2011/0046570, filed Aug. 20, 2009, titled "Systems and Methods for Providing a Flushable Catheter Assembly." Following placement of the catheter into the vasculature of a patient, an IV fluid source can be connected to the catheter adapter or catheter hub, opening the blood control valve. Thus connected, fluid from the IV source can begin flow into a patient through the catheter.

As is well known in the art, typical blood pressure is 10 to 20 centimeters of water. Infusion bags are usually placed about 100 cm above the patient's heart to direct flow into the patient. At roughly that height, the pressure exerted by the fluid from the infusion bag is much greater than the blood pressure of the patient and therefore can flow into the patient.

Some catheter adapters permit verification of proper placement of the catheter in the blood vessel before fluid infusion begins, such as by providing a flashback chamber of the catheter assembly where a "flashback" of blood can be observed. To confirm flashback in catheter assemblies that do not include a blood control valve, a clinician must manually occlude the vein to prevent undesirable exposure to blood. In contrast, blood control valves can eliminate the need for such manual occlusion, while also reducing the likelihood of blood exposure during catheter placement.

SUMMARY

An aspect of the present disclosure includes the provision for a compact design for a valve housing of a Luer activated valve.

Another aspect of the present disclosure includes the provision for a relatively strong construction for use with high pressure injection devices.

A still further aspect of the present disclosure is the provision for improving the state of the art of blood control or closed system infusion devices including intravenous catheters.

As described, a needle assembly of the present disclosure can include a number of different components. The needle assembly can comprise a needle hub with a needle extending from a distal end of the needle hub; a catheter tube attached to a catheter hub and having the needle extending through the catheter tube in a ready to use position; a valve positioned in an interior cavity of the catheter hub, said valve comprising an outer perimeter that axially floats when moved by a proximal valve opener, which is also positioned in the interior cavity of the catheter hub and proximal of the valve; and a distal valve opener having two or more leg extensions extending in a proximal direction of a body of a bushing.

The needle assembly wherein the two or more leg extensions of the distal valve opener can be axially fixed inside the interior cavity of the catheter hub.

The needle assembly wherein the valve can comprise three slits and three flaps and wherein the distal valve opener can comprise three leg extensions.

The needle assembly wherein the three leg extensions can be aligned with the three flaps.

The needle assembly wherein the proximal valve opener can comprise a ring and two plunger elements with a gap therebetween.

The needle assembly can further comprise a tip protector located at least in part in the gap of the two plunger elements.

The tip protector can be optionally and the needle assembly can be practiced without the tip protector.

The needle assembly wherein sections of the valve can be deflectable in a distal direction and sections of the valve can be deflectable in a proximal direction to open a fluid flow path through the valve.

The needle assembly wherein the sections of the valve that can be deflected in the distal direction can comprise outer edges of the valve and sections of the valve that can be deflected in a proximal direction can be flaps formed with the valve.

The needle assembly wherein the body of the bushing and the leg extensions can be integral.

In an example, only part of the tip protector or needle guard can extend into one or more gaps of the valve opener while the proximal section of the tip protector can extend proximally of the proximal most surfaces of the tip protector. For example, part of the needle guard can overlap with the valve opener along an axial direction or position while a proximal section of the tip protector, such as the proximal wall, extends proximally or be located proximally of the proximal most surfaces of the valve opener.

A still further aspect of the present disclosure is a method of manufacturing a needle assembly, such as a catheter assembly. The method can comprise: providing a catheter hub with a catheter tube with a distal opening, said catheter hub comprising a hub body defining an interior cavity and a proximal opening; positioning a bushing inside the catheter hub and against the catheter tube and positioning a valve proximal of the bushing; the valve being floatable inside the interior cavity of the catheter hub along an axial direction of the catheter hub and comprises two or more flaps; positioning a proximal valve opener proximal of the valve and inside the interior cavity of the catheter hub; placing a needle, which is attached to a needle hub, through the catheter hub, the valve, and the catheter tube so that a tip of the needle extends out the distal opening of the catheter tube; and wherein two or more leg extensions extend in a proximal direction of a body of the bushing.

The method wherein the two or more leg extensions can be aligned with the two or more flaps on the valve.

The method wherein the proximal valve opener can comprise a ring and at least one plunger element.

The method wherein the proximal valve opener can comprise two spaced apart plunger elements having a gap therebetween.

The method wherein a needle guard can be located at least in part in the gap and between the two plunger elements.

The method wherein two or more leg extensions can be fixed along an axial direction.

The method wherein the proximal valve opener can be slidable in a distal direction to move the valve in a distal direction against the two or more leg extensions.

A further aspect of the present disclosure can include a needle assembly comprising: a needle hub with a needle extending from a distal end of the needle hub; a catheter tube attached to a catheter hub and having the needle extending through the catheter tube in a ready to use position; a valve positioned in an interior cavity of the catheter hub, said valve comprising an outer perimeter that axially floats when moved by a proximal valve opener, which is also positioned in the interior cavity of the catheter hub and proximal of the valve; a distal valve opener comprising a leg extension extending in a proximal direction of a base of a bushing; and a needle guard comprising a proximal wall with an opening having the needle passing therethrough located, at least in part, in a holding space of the proximal valve opener.

The leg extension of the distal valve opener can be axially fixed inside the interior cavity of the catheter hub.

The distal valve opener can abut against a bushing and be axially fixed. A base of the distal valve opener can contact a surface of a funnel section of the bushing.

The valve can comprise three slits and three flaps and wherein the distal valve opener can comprise three spaced apart leg extensions.

The three leg extensions of the distal valve opener can be aligned with the three flaps of a valve.

The proximal valve opener can have a nose section sized for abutting contact with a proximally facing surface of a valve. The proximally facing surface can be part of a valve disc. A valve skirt can extent distally of the valve disc and define a distal holding space.

A proximal valve opener cab include two reliefs or through passages and wherein the needle guard can have two elbows, one each extending at least partly through a respective relief or through passage. In some examples, the guard can have a single elbow and the single elbow can extend through one of the two reliefs or through passages.

A needle guard of the present disclosure can be unitarily formed as a one-piece or integrally formed from multiple pieces. The needle guard can include one arm or two arm and the two arms can intersect along a side view or not intersect.

A needle guard of the present disclosure can be located in a third housing. In an example, the third housing can be located between a catheter hub and a needle hub.

A distal valve opener can be separately formed from a bushing or unitarily formed with the bushing.

A distal valve opener can comprise one continuous leg extension or can comprise two or more leg extensions each with a proximal tip or a nose section. The nose section of each leg extension can be tapered or can include a bulge section.

A proximal valve opener can have a first continuous perimeter section spaced from a second continuous perimeter section.

A space between a first continuous perimeter section and a second continuous perimeter section of a proximal valve opener or actuator can comprise one or more plunger elements.

One or more plunger element stubs can extend proximally of a second continuous perimeter section of a proximal valve opener or actuator.

A valve can comprise a skirt or valve skirt section extending distally of a valve disc. The skirt can include a generally cylindrical section and a frusto-conical section.

A base of a bushing and a leg extension of a distal valve opener can be unitarily formed.

A proximal valve opener can comprise two stabilizer elements connecting two plunger elements and wherein a gap between the two stabilizer elements can define a choke point for limiting proximal movement of a needle guard.

Aspects of the present disclosure can include a method of manufacturing a needle assembly. The method of manufacturing can comprise the steps: providing a catheter hub with a catheter tube with a distal opening, said catheter hub comprising a hub body defining an interior cavity and a proximal opening; positioning a bushing inside the catheter hub and against the catheter tube and positioning a valve proximal of the bushing and proximal of a leg extension, which has a nose section for abutting a distally facing surface of the valve; the valve being axially displaceable inside the interior cavity of the catheter hub along an axial direction of the catheter hub and comprises two or more flaps; positioning a proximal valve opener proximal of the valve and inside the interior cavity of the catheter hub; placing a needle, which is attached to a needle hub, through the catheter hub, the valve, and the catheter tube so that a tip of the needle extends out the distal opening of the catheter tube; and positioning a needle guard comprising a proximal wall with an opening having the needle passing therethrough located, at least in part, in a holding space of the proximal valve opener.

The method can further comprise placing an elbow of a needle guard through a relief or through passage of a proximal valve opener.

The method wherein a leg extension can be unitarily formed with a bushing.

The method wherein a proximal valve opener can have a nose section sized for abutting contact with a proximally facing surface of a valve.

The method wherein a proximal valve opener can have a first continuous perimeter section spaced from a second continuous perimeter section.

The method wherein a proximal valve opener can comprise two stabilizer elements connecting two plunger elements and wherein a gap between the two stabilizer elements can define a choke point for limiting proximal movement of a needle guard.

A still further aspect of the present disclosure can include a catheter assembly comprising: a needle hub with a needle having a needle tip extending from a distal end of the needle hub; a catheter tube attached to a catheter hub and having the needle extending through the catheter tube in a ready to use position; a valve comprising a valve disc positioned in an interior cavity of the catheter hub, a first valve opener positioned distally of the valve disc; a second valve opener positioned proximally of the valve disc; and a needle guard comprising a proximal wall with an opening having the needle passing therethrough, said needle guard configured to cover said needle tip in a protective position.

Also infusion or injection hypodermic needles may utilize the valve in a housing having a female Luer connector. For example, the valve and valve opener of the present disclosure may be placed inside a needle hub. Also, a needleless valve integrated in a medical device or a standalone needleless valve can utilize the valve described herein.

A needle assembly or a needle device can include a catheter hub with a catheter tube attached to the hub body and a needle hub with a needle extending through the catheter hub and the catheter tube with the needle tip extending out a distal end or distal opening of the catheter tube in a ready to use position.

In the ready position, the catheter assembly is ready for use, such as to perform a venipuncture or intravenous access. Sometimes the ready position first requires removing a protective cap (not shown) from the catheter assembly or needle assembly.

A valve and an actuator for use with the catheter hub of the present disclosure can also be placed within the needle hub as a second valve.

A needle guard or tip protector, a valve opener or actuator, a valve, and a bushing can be provided with the catheter hub.

The tip protector may embody any number of prior art guards configured for blocking or covering the needle tip of the needle. The tip protector can have a proximal wall and two resilient arms and wherein a change in profile on the needle, such as a crimp or a bulge, can engages a perimeter defining an opening on the proximal wall of the tip protector to retract the tip protector in the proximal direction out of the catheter hub following successful venipuncture. The two arms can intersect or they can run along different sides of the needle and do not intersect along a side view.

The needle guard arms can be spread by the needle shaft in a ready position and engage the inside of the catheter hub, such as the guard engagement section the catheter hub. The needle guard can be rolled or bent to final configuration from a stamped metal sheet. Alternatively, the needle guard can be formed from different components, from all metal components, from plastic components, or combinations thereof.

A valve opener or actuator can comprise a ring and at least one plunger element, such as a leg element or an elongated extension. The ring can be in contact with the valve in the needle assembly ready to use position but can be spaced or slightly spaced from the proximally facing surface of the valve.

Two plunger elements can extend from the ring in the proximal direction. In other examples, there can be more than two plunger elements, such as three or more plunger elements having gaps therebetween. The one or more plunger elements can each be sized and shaped for contact by a male Luer to transfer a distally directed force from the male Luer to the ring to then push against the valve to open the valve.

The one or more plunger elements can each have an arc shape or arc cross section along a width. In another example, the at least one plunger element can be generally flat or planar. The thickness of each of two plunger elements is sufficiently small or thin so that the needle guard and the two plunger elements have sufficient clearance to fit within the interior cross-sectional space of the catheter hub without being physically binding against the catheter hub and rendered unmovable or fixed.

In an example, the thickness of each of two plunger elements and the width of the needle guard are such that no undercut or channel is required to be formed in the interior wall surfaces of the catheter hub to accommodate them.

The valve opener can be made from a metal material or from a plastic material. When made from a metal material, the valve opener can be formed by deep draw methods and the arc shape cross section of the plunger element can provide added rigidity when pushed by the male Luer.

Each plunger element can comprise at least two lengthwise edges and a rib can be provided along one or both of the lengthwise edges to further add structural rigidity. One or more gaps can be provided between any two plunger elements. The gaps can provide clearance or space for fluid flow flowing thereacross, such as during IV infusion. The gap can also be utilized to accommodate a needle guard.

The ring of the valve opener can comprises a body with an outer perimeter. The outer perimeter can be generally cylindrical. The outer perimeter can have a taper. The body can comprise a chamfer and an opening.

The distal edge or intersection of the body between the chamfer and the outer perimeter can have a sharp edge or a blunt edge. In an example, the intersection is a blunt edge comprising a planar surface for pushing against the valve.

On the proximal side of the ring, the two plunger elements can be recessed inwardly from the outer perimeter to form a shoulder. The outer perimeter of the ring can have an outside diameter of a first dimension and the two plunger elements can define an outside diameter of a second dimension, which is smaller than the first dimension. A shoulder can be provided between the two different dimensions.

The valve opener can have an inside diameter measured adjacent the intersection. The inside diameter can change or vary along the chamfer section of the ring. The valve opener can further include a minimum inside diameter mID, which can be viewed as the smallest inside diameter of the valve opener.

The needle guard can be located between one or more gaps defined by the plunger elements. The plunger elements can each comprise an arc-shape cross section. The arc-shape cross section of each plunger element can be generally C-shaped with the concave portion facing internally towards the needle guard and the convex portion facing outwardly away from the needle guard.

The radius of curvature of the two C-shaped plunger elements should be different than the radius of a male Luer tip and/or the radius of the interior cavity of the catheter hub. A gap can be provided on each side edge of the proximal wall of the needle guard and the adjacent plunger element.

The two plunger elements can each have an abutting proximal surface that is sized and shaped to be pushed against by a male Luer tip or a syringe tip when said tip is inserted into the proximal opening of the catheter hub following successful venipuncture to push the valve opener distally to open the valve. The arc-shape cross section of each of the two plunger elements can provide a sufficiently thick profile to ensure overlapping abutting surfaces with the male Luer tip and rigidity from buckling.

The C-shaped plunger elements can avoid deflection when pushed by a syringe tip or other male Luer tip, avoid slippage of the syringe tip or Luer tip missing the end surfaces of the plunger elements when the syringe tip or Luer tip is inserted into the open proximal end of the catheter hub, and/or avoid a situation in which the syringe tip or Luer tip is pushed between the two plunger elements to wedge the two plunger elements between the tip and the interior surface of the catheter hub during activation of the valve opener.

In some embodiments, the concave portion of the arc-shape cross-section of each plunger element can face outwardly, away from the needle guard, while the convex portion of each plunger element faces inwardly towards the needle guard.

The ring of the valve opener can be elastically deformed and then expand when it reaches a recessed hub section of the catheter hub, which can accommodate the ring without deforming the ring. Alternatively, the catheter hub can be designed to expand to allow the assembly of the valve opener. A shoulder can be provided at the recessed hub section, which can form a physical stop for engaging the shoulder on the valve opener. This can allow the valve opener to be retained within the interior cavity of the catheter hub during needle withdrawal and during use, when the valve opener is pushed distally to activate the valve and subsequently moves proximally when the male Luer is removed, thus allowing the valve to close.

A valve can have a valve disc comprising a valve body comprising a valve diameter, a valve thickness measured orthogonal to the valve diameter between a proximally facing surface and a distally facing surface, and one or more slits defining two or more flaps.

Three slits can be provided through the valve thickness to define three flaps. The three slits can originate from a point and extend radially from about a center point or central portion of the body of the valve, similar to a three-point star, to form three flaps that can deflect along the slits.

The valve can comprise an outer perimeter that can float inside the interior cavity of the catheter hub, between the valve opener and the bushing. The outer perimeter of the valve can move proximally and distally within the interior cavity of the catheter hub and not be restrained by the catheter hub along an axial direction of the catheter assembly.

The outer perimeter of the valve can be the same or smaller or larger than the outer perimeter of the ring of the valve opener. However, at least some part or all of the distal edge or intersection of the ring can be recessed from the outer perimeter of the valve so that the distal edge can abut or touch the proximally facing wall surface of the valve. Also, since the valve can float, the valve can be positioned inside a single hub body catheter hub and can avoid being wedged between a multi-part hub body. However, the various components described herein may readily be used with a multi-piece catheter hub without deviating from the scope of the present disclosure.

The bushing of the present disclosure can comprise a body comprising a first body section and a second body section extending from the first body section. The second body section can having a cone shape section and two or more leg extensions extending from the second body section, such as extending from the cone shape section.

The first body section can have an elongated body that can have a cylindrical shape with an optional tapered distal tip or nose section. In some examples, a generally cylindrical ring extends from the second body section and the two or more leg extensions extend from the cylindrical ring.

One or more gaps can be provided between two adjacent leg extensions. The number of leg extensions incorporated with the bushing can be the same as the number of flaps incorporated with a valve.

The leg extensions on the bushing can define an outside diameter that is smaller than the minimum inside diameter mID of the valve opener. The proximal tip of each leg extension can have a chamfer or a blunt tip. In one example, a chamfer can be incorporated at the proximal tip of each leg extension and wherein the chamfer can taper inwardly from the exterior of the leg extension.

The bushing can be made from a metal material and the leg extensions can be unitarily formed with the body. Alternatively, the leg extensions can be welded to the body.

The bushing and the valve can be oriented in the catheter hub so that the leg extensions on the bushing are aligned with the flaps on the valve. This allows the flaps on the valve to be pushed by the leg extensions on the bushing. Thus, if there are three flaps on the valve, the three flaps will be pushed into physical contact with three leg extensions on the bushing.

The distally facing wall surface of the valve can touch the leg extensions and/or the elastic element or be spaced from the leg extensions on the bushing and/or the elastic element in the valve closed position and be pushed against the leg extensions during use. In other examples, the valve can touch the proximal tips of the leg extensions and/or the elastic element in the closed position of the valve or be spaced therefrom.

The three leg extensions can be equally spaced along a circumference of the second body section of the bushing. In another example, the three leg extensions can be located and spaced in accordance with the positions of the lugs on the valve so that when assembled inside the catheter hub, the valve can be pushed distally by the valve opener or valve actuator and the leg extensions on the bushing are aligned to push the lugs of the valve in the proximal direction to open the valve.

During retraction of the needle in the proximal direction following successful venipuncture, the tip protector can be held axially by the engagement between one or both resilient arms on the tip protector and a guard engagement section on the catheter hub.

The guard engagement section can be a surface discontinuity formed on the interior surface of the catheter hub. For example, the guard engagement section can comprise a section of a first inside diameter and a section of a second inside diameter, which is larger than the first inside diameter.

The guard engagement section can embody an internal projection or a groove or a combination of both a groove and a projection formed on the interior surface of the catheter hub. When a combination of a groove and a projection is used for a guard engagement section to engage the needle guard or tip protector, the groove can be distal to the projection. Two spaced-apart guard engagement sections can be provided for engaging the two resilient arms on the tip protector. The two guard engagement sections can be located diametrically opposed of each other just distal of the section of the female Luer taper of the catheter hub.

In an example, the valve opener can incorporate a single plunger element. The single plunger element can embody a generally cylindrical body section having an interior surface defining a bore having a path or channel. The cylindrical body section can be located proximally of a distal push end. A guard engagement section can form on the interior surface of the present valve opener. In other words, the guard engagement segment can be provided with the interior surface of the valve opener instead of the interior surface of the catheter hub. This allows the two resilient arms of the tip protector to engage the valve opener in the ready to use position and during retraction of the needle following successful venipuncture.

The guard engagement section formed on or with the valve opener can be a projection, a recess, or an opening.

In yet another example, two openings can be provided through the wall layer of the cylindrical body portion of the valve opener for use with the guard engagement segment formed with or on the interior of the catheter hub. The openings each can comprise a perimeter, which can be a closed perimeter.

In the ready to use position using the valve opener with two large openings provided through the wall layer of the valve opener, the resilient arm or arms of the tip protector can project through the openings to engage the guard engagement segment of the inside of the catheter hub instead of or in addition to engaging opening of the valve opener.

The guard engagement segment can be formed on the interior surface of the catheter hub and the proximal cylindrical body section comprises an opening that surrounds the guard engagement segment.

During retraction of the needle, the needle tip moves proximally of two distal walls, one on each end of the resilient arms of the tip protector. The needle guard can instead have one distal wall and/or one arm.

The change in profile on the needle can engage the inside perimeter of a hole or bore through the proximal wall of the tip protector. Once engaged, the tip protector is moved proximally with the needle to be removed from the catheter hub. In the protective position in which the tip protector covers or blocks the needle tip, the valve remains inside the interior cavity of the catheter hub. Thus, the valve is located inside the catheter hub in both the ready position of the needle and the protective position of the needle.

A male medical implement or instrument can be a male Luer, a syringe tip, an IV set connector, or other male tip having a Luer taper, and can be inserted into the open proximal end of the catheter hub. The male medical implement can be connected to an IV tubing, which can be connected to an IV fluid source for fluid delivery through the male medical implement.

When initially inserting the male medical implement or male tip into the proximal opening of the catheter hub, the male tip initially contacts the two plunger elements on the valve opener to advance a distally directed force on the two plunger elements to open the valve. The arc cross section of the plunger elements can have a smaller diameter than the inside diameter of the catheter hub to provide a larger contact surface for the distal end of the male medical instrument.

The distally directed force can move the valve opener in the distal direction until the geometries of the male tip and the proximal opening of the catheter hub stop further distal advancement of the male tip. A seal can be provided by the Luer engagement to prevent fluid from leaking out the proximal opening of the catheter hub.

The ring can be urged distally and pushes against the proximally facing surface of the valve. The distal edge of the valve opener can initially push against the proximally facing surface of the valve. As the valve is axially movable inside the catheter hub, the valve can be urged distally by the valve opener, which can be urged distally by the male tip.

Due to the presence of the leg extensions on the bushing, the outer edges or outer valve sections of the valve can move distally while other parts on the valve that abut or contact the leg extensions can be stopped from moving distally by the leg extensions. In effect, the valve outer edges can move distally while the flaps on the valve can deflect from a central point or location radially outwardly and in a proximal direction by the leg extensions on the bushing to open a flow path through the valve.

The chamfer on the ring and the chamfers on the leg extensions can facilitate deflection of the flaps on the valve radially outwardly and in the proximal direction. Also, the relative diameters defined by the leg extensions and the minimum inside diameter mID of the valve opener can allow the valve opener and the bushing to deflect the valve therebetween to open the valve. Alternatively, the outer perimeter of the valve can remain in contact with the inside wall of the catheter hub, when pushed distally, with only the flaps opening around the slit or slits.

Thus, an aspect of the present disclosure is understood to include a catheter assembly comprising a valve comprising one or more slits and two or more flaps wherein the valve comprises parts or sections that move in a distal direction and parts or sections that open along a radial direction and in a proximal direction to open a flow path through the valve.

In an example, outer edges of the valve can be configured to move distally while the flaps of the valve can be configured to move radially outwards to open a flow path through the valve. Also, by incorporating a valve that can move in this fashion to open a fluid flow path, the actuation distance that the valve opener has to travel in the axial direction of the catheter assembly can be minimized compared to a valve having flaps that only open in the distal direction by a valve opener. Thus, the size of the catheter hub, such as the length of the catheter hub, can be reduced compared to one that utilizes a valve and a valve opener that opens the valve by deflecting the valve flaps only in the distal direction.

A catheter assembly comprising a valve and wherein the valve perimeter can float in the axial direction relative to the catheter hub is disclosed. By incorporating a valve with a valve perimeter that can float in the axial direction, a two-part catheter hub is not required to secure the valve perimeter therebetween and inside the catheter hub, although a two-part hub can be used. Therefore, a catheter hub with a singularly formed hub body may be used with the present catheter assembly. Thus, the size of the catheter hub, such as the outer diameter or dimension of the catheter hub, can be reduced compared to one that utilizes a two-part hub body. The two part hub body where they join along a seam can thus be reduced to provide a catheter assembly with a relatively smaller outer profile.

The valve opener can be configured to push the valve against another structure, such as the leg extensions on the bushing. The present valve opener may be viewed as having a multi-piece valve opening structure. For example, the part with the ring and the plunger elements may be viewed as a proximal valve opener and the bushing with the leg extensions may be viewed as a distal valve opener. The two valve openers can cooperate to open a valve.

A proximal valve opener can be sized and shaped to push against the outer edges of the valve in the distal direction to move the valve against the distal valve opener. The distal valve opener can be sized and shaped to push the flaps on the valve in a radially outward direction and part of the flaps in a proximal direction to open a fluid path or flow path through the valve.

In an example, the leg extensions 196 on the distal valve opener are axially fixed and by pushing the flaps of the valve in a distal direction against the leg extensions, the flaps are deflected radially outward by the leg extensions on the distal side of the valve. In other words, when the valve is actuated to open a flow path through the valve, the valve is being physically pushed by an actuator on a proximal side of the valve and an actuator on the distal side of the valve. In a particular embodiment, the valve can be actuated to open a flow path through the valve by being physically pushed by a ring on a proximal side of the valve and leg extensions on the distal side of the valve.

The proximal tips of the leg extensions and the distal edge of the ring can be spaced from a plane drawn orthogonally to the lengthwise axis of the catheter assembly. In other words, the proximal tips of the leg extensions and the distal edge of the ring do not have to overlap from the perspective of this plane and a gap can be provided between the two to accommodate the valve therebetween.

The proximal tips of the leg extensions and the distal edge of the ring can alternatively overlap along an axial direction, which can produce the effect of deflecting the flaps radially outwards a relatively greater amount than when there is no overlapping. Further, because the flaps can be pushed against axially fixed leg extensions on the bushing, the flaps can deflect backwards in the proximal direction by the leg extensions. In yet other examples, the proximal tips of the leg extensions and the distal edge of the ring can just touch along a plane drawn orthogonally to the lengthwise axis of the catheter assembly.

A catheter assembly can be provided comprising a valve, a proximal valve opener, a distal valve opener, a needle hub with a needle, and a catheter hub with a catheter tube.

The valve assembly can further include a tip protector for blocking the needle tip in a needle protective position.

Following successful venipuncture, a male tip, such as a male Luer, can be inserted into a proximal opening of the catheter hub to advance the proximal valve opener in a distal direction, which moves the valve in a distal direction against the distal valve opener.

The flaps of the valve can be pivoted in a proximal direction to open the fluid path through the valve. The flaps of the valve can deflect in a proximal direction by the leg extensions of the bushing of the present device. The flaps can be deflected in the proximal direction by pushing the flaps against stationary leg extensions on a distal valve opener.

The flaps on the valve can be deflected in a proximal direction by a structure located distally of the valve and abutting a distally facing surface of the valve.

The distal valve opener can be a metal bushing having a body with a cone shaped section having two or more leg extensions extending therefrom in a proximal direction. The bushing may also be made from a thermoplastic material.

The biasing or resilient nature of the valve, which can be made from an elastomer, allows the valve to recoil to its more relaxed state when the male tip of a syringe or male medical implement is removed from the catheter hub. Thus, the flaps on the valve can recoil by moving distally while the outer edges or outer sections of the valve body can recoil proximally. This recoil can push the proximal valve opener in a proximal direction and the shoulder on the proximal valve opener can move towards or against the shoulder inside the interior cavity of the catheter hub.

A coil spring, a leaf spring, or an elastomeric cylinder can optionally be placed between the distally facing surface of the valve and an inside distal step or shoulder of the catheter hub to facilitate closing the valve. This spring or elastomeric cylinder, if incorporated, can provide extra biasing force to return the valve to a closed position when the male medical instrument is removed. The added component can optionally be omitted. If incorporated, the elastic component can be spaced from the valve in the ready to use position shown or can contact the valve in the ready to use position.

The valve may be opened again by placing a male tip into the proximal opening of the catheter hub and pushing the proximal valve opener in the distal direction.

Methods of making and of using the catheter assemblies and their components described elsewhere herein are within the scope of the present disclosure.

The proximal opening of the catheter hub can be sized and shaped to receive a male medical implement, such as a male Luer tip.

A tip protector is configured to be removed with the needle following use and a valve and valve actuator can remain with the catheter hub for controlling fluid flow therethrough. The actuator can be configured to push into the valve to open the valve for fluid flow.

A flash back plug can be provided at a proximal end of a needle hub, which allows air to vent but stops blood from spilling out the proximal end of the needle hub when entering the flashback chamber during primary flashback. Alternatively, a syringe can be attached to the proximal end of the needle hub. The valve and actuator described further below can also be placed within the needle hub as a second valve.

The needle hub can comprise a shoulder or other surfaces to physically contact the catheter hub, such as the proximal end surface of the catheter hub, to axially register the two hubs to set the length of the needle tip projecting out of a distal opening of the catheter tube.

A protective cap with a sleeve and a saddle can be provided to cover the needle during packaging and before use. The saddle can surround at least part of the catheter hub and the needle hub and be removably engaged to the needle hub. The cap should be removed from the needle assembly before use.

The catheter hub can be provided with a pair of wings to facilitate securement of the catheter hub to a patient following use.

A valve with a valve disc and a valve skirt can be located in a catheter hub. The valve disc can comprise one or more flaps and one or more slits to be opened by a valve actuator. In an embodiment, the valve skirt can be positioned in a recessed section formed in an interior cavity of a catheter hub and is axially slidable along the interior of the catheter hub when actuated to open for fluid flow.

The valve can be spaced from a reduced neck section of the catheter hub, which can anchor the funnel section of the bushing in place. The space between the reduced neck section and the valve skirt of the valve may be referred to as the distal interior cavity.

The valve disc of a valve can comprise a valve outside diameter, a valve thickness measured orthogonal to the valve diameter, and one or more slits formed through the valve thickness defining two or more flaps. For example, one or two or three slits may be provided through the thickness of the valve disc to define two, three, or more flaps.

A valve skirt can extend axially of a valve disc, forming a generally cylindrical skirt section. In some embodiments, the valve skirt may be sloped such that the valve skirt forms a frusto-conical structure. Thus, a valve skirt can have a generally cylindrical section and a frusto-conical structure or section.

A valve skirt can have a distal opening having an area or dimension that is sized and shaped to receive a distal valve opener. A tapered or radiused entrance can be provided at the distal opening of the valve skirt to receive the nose of the distal valve actuator to open the valve flaps of the valve disc when the valve is actuated.

The distal opening of the valve skirt can lead into a distal holding space of the valve skirt. In other words, the valve skirt can have an interior space, which can be a distal holding space.

The holding space can be defined by a first interior section having a first internal diameter and a second interior section having a second internal diameter, which is a larger than the first internal diameter. A shoulder can be provided at the interface between the first interior section and the second interior section. In an example, the shoulder inside the distal holding space can have a radius.

The valve can comprise an outer perimeter that can float inside the interior cavity of the catheter hub, between the proximal valve actuator and the bushing. For example, the outer perimeter of the valve can move proximally and distally within the interior cavity of the catheter hub and not be restrained, other than perhaps friction or touching, by the catheter hub along an axial direction of the catheter assembly.

In an example, the cylindrical portion of the skirt section of the valve can be pressed against the interior surface of the interior cavity in a slight interference fit to form a seal therebetween. The generally flat outer contour of the cylindrical portion of the skirt can allow the valve to move in the axial direction when pushed by the proximal valve actuator while maintaining concentricity with the bore of the catheter hub.

In some examples, the outer perimeter of the cylindrical section of the valve can be the same, smaller, or larger than the outer perimeter of the nose section of the proximal valve actuator. The relative dimensions between the cylindrical section of the valve and the outer perimeter of the proximal valve actuator, such as the nose section, can be configured so that the valve actuator can push against the proximally facing surface of the valve disc to axially move the valve.

Generally speaking, the relative dimensions of the nose section of the proximal valve actuator and the outer perimeter of the cylindrical section of the valve can be such that the nose section can push against the proximally facing surface of the valve, when pushed distally by a male medical implement, at a location closer to the outer perimeter of the valve disc than to a center or central portion of the valve disc.

The distal valve actuator, such as the nose section of the distal valve actuator, can be configured to push against the valve disc at a location closer to the center or central portion of the valve disc than to the outer perimeter of the valve disc.

The proximal valve actuator can push against the proximally facing surface of the valve disc while the distal valve actuator can push against the distally facing surface of the valve disc.

Since a valve can float within the interior of a catheter hub, such as move axially along the lengthwise axis of the catheter hub, the valve can be positioned inside a single hub body catheter hub. In other words, the valve does not have to be retained inside a catheter hub by two or more catheter hub bodies, such as along a seam of two or more hub bodies. However, the various components described herein may readily be used with a multi-piece catheter hub without deviating from the scope of the present disclosure.

The proximal valve actuator can comprise a nose section, which can be generally cylindrical and terminates in an actuation end. The actuation end can have a blunt distal end surface or has a sharp edge. The nose section can have a wall surface with a continuous circumference or continuous perimeter section, without a gap or slit, such as a cylinder with a continuous wall. The nose section can define a bore. In some examples, a plurality of spaced apart slits and/or openings can be provided on the nose section of the proximal valve actuator, away from the continuous perimeter section, to permit flow or fluid flushing.

Two actuating elements or plunger elements can extend proximally of a nose section. For example, the two plunger elements can be unitarily formed with the nose section and can extend from the nose section in the proximal direction. A gap or space can be provided between the two plunger elements for positioning the needle guard or tip protector therebetween. The gap of a proximal valve opener for positioning a needle guard can be called a holding space.

The plunger elements can each comprise at least two lengthwise edges and the edges can be spaced from one another. The lengthwise edges of the plunger elements can align with a lengthwise axis of the valve opener.

A projection can extend outwardly from an outer surface of one or both plunger elements of a valve actuator. A projection can extend from the outer surface of each plunger element. Each projection can resemble a ramp surface having a generally flat edge for abutting a shoulder in the recessed section of a catheter hub to restrict the valve actuator from moving in the proximal direction.

The ramp surface of a projection and the direction of the ramp can allow the actuator to be inserted into the interior of the catheter hub from the open end and be seated within the recessed section. Some embodiments of a valve actuator may utilize other shapes for the nose section, such as cuboid, rectangular, conical, pyramidal, chamfered or the like.

In an example, a valve actuator or valve opener has a lengthwise axis and one or more actuating elements extend axially or parallel to the lengthwise axis. In a particular example, two actuating elements can be diametrically opposed to one another along the lengthwise axis. In other examples, the actuating elements are not equally space around the periphery of the nose section.

Two actuating elements can define an outer diameter having a dimension that is approximately similar or the same as a diameter of a nose section.

In an example, the actuating elements of a valve opener can be flexible and deflectable so that when pushed by a male Luer tip, the actuating elements can defect or flex. The actuating elements can be deflectable by selecting a material that has the requisite resilient properties. In other examples, the actuating elements can be deflectable by incorporating one or more weakened sections, such as by incorporating a structurally thin section, by incorporating cut-outs, by employing a small cross-section compared to other sections of the same elongated actuating element, or combinations thereof. Alternatively, the actuating elements can be flexible and deflectable by selecting a material that has the requisite resilient properties and by incorporating one or more weakened sections.

In still other examples, each actuating element of a valve opener can have more than one different cross-sectional profiles or contour along a length section. For example, an elongated plunger element can have a square profile located adjacent a crescent-shaped profile.

In an example, the actuating elements can be rigid and not deflectable or deformable when loaded, such as when pushed, by a male Luer tip. Further, stabilizing elements may be incorporated to increase the rigidity of the actuating elements.

The actuating elements may each include a cross-sectional profile, at least at a proximal end, that overlaps a push end of a male tip so that the male tip can push the valve actuator into the valve 1.

The nose section of a valve actuator can be configured to engage the valve to open the valve disc when an axial force is applied by a male tip to the actuating elements towards the distal end of a catheter assembly, such as during the insertion of an IV drip line of a male Luer connector.

Generally, a nose section of a proximal valve opener is rigid relative to the more pliable valve, which allows the nose section, and more specifically the actuation end, to actuate the valve, such as to deflect the one or more flaps of a valve disc and open the one or more slits on the valve disc. The nose section may be made of a non-compressible material, such as metal, a rigid plastic, or a hard elastomer for pushing against and opening the valve.

The proximal valve actuator can include a pair of opposed bands or stabilizers connecting two actuating elements at a location along the length of the actuating elements that are between the nose section and the proximal most end or end surface of the valve actuator. In some examples, the stabilizers can be located at the proximal end of the two actuating elements so that proximal edges of the stabilizers can be generally flush with the proximal end surfaces of the actuating elements. The two stabilizer elements can be referred to as a first or upper stabilizer element and a second or lower stabilizer element. One or more holes can be provided with the actuating elements and/or the stabilizer elements for molding purposes, such as for the core pins.

In one embodiment, the stabilizers or stabilizer elements can be arc-shaped, forming an arc following the interior profile of the catheter hub and connecting one actuating element to another actuating element. The stabilizers or stabilizer elements may form a substantially cylindrical section on the body of the valve actuator, which cylindrical section can be spaced apart from the nose section of the valve actuator. In other words, the valve actuator can be elongated and can have sections that are continuous along a radial direction and sections with reliefs or through passages through the wall of the actuator that are not continuous along the radial direction.

In an example, the stabilizers can define a continuous body section along a perimeter or radial direction of a proximal valve actuator that is spaced from a continuous body section of a nose section, which can also include a continuous section along a perimeter or radial direction.

Two stabilizers or stabilizer elements may join with two plunger elements to form a ring structure, which can be called a stabilizing ring. Optionally, the stabilizer elements may be slightly offset and angled from each other. In some embodiments, there may be one, three, or a different number of actuating elements or different number of stabilizer elements.

In an example, the valve actuator, with the stabilizers or stabilizer elements and projections, can be made from plastic, such as by plastic injection molding.

The stabilizers can help the proximal valve actuator remain centered within the catheter hub while the actuator moves, such as when pushed by a male Luer tip following successful venipuncture. By staying centered, the nose section can be better aligned with the valve disc, such as the slits on the valve disc, allowing for smooth actuation of the valve.

The stabilizers or the stabilizing ring can also provide an engagement with the catheter hub, via friction or snug fit, with the interior of the catheter hub to prevent the actuator from sliding in the proximal direction following removal of the male Luer tip.

In one embodiment, the nose section of a proximal valve opener can be configured to push against the proximal facing surface of the valve disc and the distal valve opener can be configured to push against the distally facing surface of the valve disc to open the slits and deflect the flaps on the valve disc.

In an example, a nose section of a proximal valve actuator can be configured to push against an outer region of a proximal facing surface of a valve disc and a distal valve opener, such as a nose section of the distal valve actuator, can be configured to push against a central region of a distally facing surface of the valve disc to open the slits and deflect the flaps of the valve disc. The perimeter and the central region can be radially positioned relative to one another.

A relief, opening, or through passage can be provided between a nose section and a stabilizing ring. Two reliefs or through passages can provide clearance so that the interior or central part of the valve actuator and the interior surface of the catheter hub can be in open communication. In other words, between a continuous section of a nose section, the continuous perimeter section defined by two stabilizers and two plunger elements, i.e., the stabilizing ring, can be one or two reliefs, through passages, or openings.

The nose section of a valve opener can define a bore and the stabilizing ring can define a bore. A needle guard or tip protector can be located in a holding space of a valve actuator and can project from the holding space at least partially through the through passages to either contact the perimeter of the reliefs and/or the interior surface of the catheter hub.

The stabilizing ring of a valve actuator can have an inside diameter that is smaller than the diameter defined by the diagonal section or elbows of two arms of a needle guard when the two arms are biased outwardly by the needle shaft in the ready to use position. Thus, during installation of the needle guard into a holding space of a valve actuator, the diagonal section or elbows of needle guard can deflect to pass through the stabilizing ring and into the open areas defined by the reliefs.

When a tip protector is positioned between two plunger elements, the two distal walls of the needle guard, more specifically the two diagonal sections or elbows, can be located in the reliefs to engage the guard engagement surface on the interior surface of the catheter hub. This can allow the needle guard to project from the holding space of the valve actuator through the two reliefs so that one or both elbows can engage the guard engagement surface of the catheter hub, such as the shoulder in the recessed section of the catheter hub or other guard engagement surfaces in the catheter hub.

The needle guard can be retained within the interior of a catheter hub by projecting through two reliefs of a proximal valve opener in a ready to use position and during retraction of a needle following successful venipuncture until the needle tip moves proximal of the two distal walls on a needle guard, at which time the needle guard can close over the needle tip and be removed with the needle.

Each stabilizer element of a valve opener can have a distal edge or first edge and a proximal edge or second edge.

Alternatively to contacting the shoulder of a recessed section of a catheter hub or other guard engagement surface inside the catheter hub, the elbows of a needle guard can be spaced from the interior surface of the catheter hub, or spaced from the shoulder, and be retained by the perimeters of the reliefs or through passages, such as by the distal edges of the two stabilizer elements.

The perimeters or distal edge of one or both stabilizer elements of a valve opener can provide the restraining surface to prevent the needle guard from early activation during retraction of the needle, prior to the needle tip moving proximally of two distal walls of a needle guard. Thus, the reliefs or through passages of a valve actuator can function as choke points or restraining points to restrict the needle guard from proximal movement until the needle guard reduces its radial profile, such as following movement of the needle tip proximally of the distal walls of the needle guard.

In an example, the perimeters of the through passages can function as choke points for limiting proximal movement of the needle guard until after activation. In a particular example, one or both distal edges of stabilizer elements can function as choke points. In other examples, a gap between two interior surfaces of two stabilizer elements can define the choke gap for restricting early activation of the needle guard.

In some examples, one or both stabilizer elements can have a slit or a channel, thus dividing the arc-shaped of each stabilizing element into two segments having a gap or a slit between the two segments. Even with a slit on one or both stabilizer elements, the stabilizing ring formed with the segments, which can be a non-continuous ring, similar to a ring with one or more slots formed through the ring, can still provide the restraining surface to prevent the needle guard from early activation during retraction of the needle, prior to the needle tip moving proximally of two distal walls of a needle guard. Further, the two segments of each stabilizer element can provide stability and reinforcement of the two plunger elements on the valve actuator.

The restraining surface of each distal edge can be referred to as a restrict point, choke gap, or choke point since it provides a rigid structure that prevents the needle guard from moving proximally thereof unless or until the needle guard first activates and collapses radially to reduce its radial profile to then slip proximally of the choke point. In an example, one or two elbows of a needle guard can be restricted by the choke point from moving in the proximal direction until the one or two elbows of the needle guard deflect to reduce needle guard's radial profile.

In an example, when the radial profile of a needle guard is reduced, the needle guard can slip through a bore defined by a stabilizing ring, from a distal position of the stabilizing ring to a proximal position of the stabilizing ring.

The valve opener can be made from a metal material or from a plastic material. When made from a metal material, the valve opener can be formed by deep draw methods and the arc shape cross section of the actuating element can provide added rigidity when pushed by a male Luer. When made from a metal material, the stabilizer elements can each be made from two stabilizer segments having a slit or a slot between the two segments. When utilizing stabilizing segments, the stabilizing ring formed thereby can be non-continuous.

Each actuating element of a valve opener can comprise at least two lengthwise edges and a rib can be provided along one or both of the lengthwise edges of the actuating element to further add structural rigidity. One or more gaps can be provided between any two actuating elements. In some embodiments, a majority or most if not all of a tip protector can fit within a holding space formed by the body of a valve actuator having a nose section for pushing against a valve.

A needle guard can be located in a holding space between two plunger elements, in a ready to use position. This arrangement can allow the catheter hub to be more compact, as less longitudinal space is needed within the hub to fit both the actuator and the tip protector serially lengthwise or when the two only partially overlap in the axial direction.

A tip protector can fit completely within a holding space of a valve actuator to further reduce the needed space or length in the catheter hub to accommodate the two. The proximal wall of a needle guard can be generally flush or even with the proximal end surfaces of two plunger elements. In other examples, the proximal wall of the needle guard can locate distally of the proximal end surfaces or proximally of the proximal end surfaces.

When a tip protector only engages with a distal edge of a relief or through passage of an actuator, then no deformity or change of diameter is required on the inside wall of the catheter hub and the tip protector can be placed further proximally in the female Luer taper section of the catheter hub while complying with the international Luer standard for conical fittings and the overall length of the catheter hub can be reduced accordingly.

The distal valve actuator or opener of the present embodiment can comprise a base, a leg extension and a proximal tip or nose section. The base can be sized with an outward tapering feature to mate with the funnel section of a bushing.

In an example, a base of a distal actuator can be sized to have a contact fit with the funnel section of a bushing. For example, the base can contact the proximally facing surface of a funnel section of a bushing.

The base of a distal actuator can have a rim for wedging against a reduced neck section at a distal interior cavity of a catheter hub. As shown, the reduced neck section can block the rim of the base from displacing in the proximal direction.

In an example, a distal valve actuator can be formed by deep draw methods, allowing the base to be flared from a proximal end of a cylindrical tube or structure.

The leg extension of a distal valve actuator can be elongated and can extend in the proximal direction of the base and terminates in a nose section or proximal tip. In an example, the leg extension can be generally cylindrical and defines a bore.

The wall defining the bore of the distal actuator can be continuous along the circumference. In some examples, slits or slots may be provided in or through the wall of the leg extension for fluid flow thereacross, such as for flushing.

In an example, the proximal end of a leg extension can be folded to form a folded section, similar to a hemmed pants. The folded section can include two wall layers 520 a rounded proximal edge formed by folding a surface on itself, which can be called a folded edge. A shoulder can provided at the interface between the leg extension and the nose section.

The nose section of a distal valve actuator can project into a distal holding space of a valve in a ready to use position with the rounded proximal edge of the actuator either in contact with the distally facing surface of a valve disc or spaced from the distally facing surface.

In an example, the interior diameter of the first interior section of the valve contacts the exterior surface of the wall of the actuator. In a particular example, the interior diameter of the first interior section can grip the exterior surface of the wall of the leg extension of a distal valve actuator. A seal can be provided between the first interior section of the valve and the exterior surface of the wall of the distal actuator. The seal can be a fluid tight seal.

The tension or interference provided by the first interior section of a valve gripping the exterior of the wall of the distal valve actuator can be adjusted by selecting the inside diameter of the first interior section, the material type for the seal, which can be made from a poly-isoprene or any suitable bio-compatible elastic material, the durometer of the molded seal, and/or the length of the first interior section. In an alternative embodiment, there is no seal between the first interior section and the exterior wall of the valve actuator, such as a distal valve actuator.

In a ready to use position, a shoulder at a nose section of a distal valve actuator can be located distally of a shoulder located between the first interior section and the second interior section of a distal holding space of a valve. In an example, the folded section, which can have a larger diameter than the diameter of the leg extension, can be located in the second interior section.

The wall of the leg extension can contact the first interior section when the folded section is located in the second interior section. The shoulder of the distal valve actuator can contact or be spaced from the shoulder inside the distal holding space in the ready to use position.

Two arms and two distal walls of a needle guard can move radially to reduce the radial profile of the needle guard. The distance between two elbows of a needle guard can decrease when the two distal walls of the needle guard are no longer biased by a needle to decrease the radial profile of the needle guard.

The radial profile at the elbows can be smaller than the choke points defined by two distal edges of a stabilizing ring of a proximal valve actuator. Further, because the proximal wall on a needle guard remains the same, a needle guard section distal of a stabilizing ring can be smaller in radial dimension than the radial dimension of the proximal wall located proximal of the stabilizing ring.

In an example, proximal movement of a needle can move the distal walls and the two elbows of a needle guard through a bore defined by a stabilizing ring of a proximal valve actuator and out a proximal opening of a catheter hub.

In an example, the valve can close upon removal of the needle from the valve disc. In some examples, there may or may not be a slight gap or leakage of fluid through the slits when the valve closes. However, leakage, if any, is minimal and a practitioner is allotted ample time to prepare the catheter hub for fluid transfer without risking fluid flow out the open proximal end of the catheter hub when the valve closes.

In an example, blood flashback from a patient can accumulate at a distal holding space of the valve. As a fluid tight seal can be provided between the leg extension of a distal valve actuator and a first interior section of a valve, the distal interior cavity of a catheter hub can remain relatively free of any blood flashback.

A distal end of a male tip can contact a proximal end surface of a proximal valve actuator. Following insertion of a male Luer tip into a catheter hub, the male Luer tip can still advance further distally into the catheter hub until the two Luer surfaces, of the tip and of the catheter hub, register, to push a valve disc of a valve into a distal valve opener.

When a male medical implement is fully inserted into a proximal opening of a catheter hub and advancing a proximal valve opener distally forward to push a valve axially distally forward, the valve can be pushed against a distal valve opener.

In an example, a stabilizing ring can provide a bearing surface or support for the proximal valve actuator as the actuator moves.

The nose section of a proximal valve actuator can push against an outer periphery of a proximally facing surface of a valve disc to axially move the valve.

A cylindrical section of a valve skirt can slide axially against the interior surface of the interior cavity of a catheter hub. In an example, the valve skirt can be pushed distally until the frusto-conical section of the valve skirt contacts the reduced neck section of the catheter hub. In another example, the registering of the two Luer surfaces stops the male tip from moving the valve skirt into contact with the reduced neck section.

In an example, when a valve is moved distally by a proximal valve opener, the valve disc can slide over the leg extension and the nose section of the distal valve opener and the distal valve opener can penetrate through the slits and deflect the flaps.

In an example, the flaps can deflect radially and proximally when actuated.

Whereas a valve skirt and a valve disc can move distally forward when actuated by a proximal valve opener, which can move distally forward by a male Luer tip, the flaps of a valve disc can deflect radially and proximally, opposite to the direction of movement of the valve skirt.

In an example, part of two or more flaps of a valve can be situated between the nose section of a proximal valve opener and the leg extension of a distal valve opener when the valve is actuated by both the proximal and distal valve actuators.

In some examples, part of two or more flaps of a valve can be situated between the nose section of a proximal valve opener and the nose section of a distal valve opener when the valve is actuated by both the proximal and distal valve actuators.

In an example, the needle device has a one-time valve actuation mechanism or one-time use since the valve can remain opened and not return to its closed position from its activated position upon removal of a male Luer tip.

When a valve is actuated, the nose section of a distal valve actuator can move a penetrating distance into the valve and proximally of a valve disc such that friction and other constraints prevents their separation.

The nose section of a distal valve actuator can be configured so that when a valve disc is pushed into the nose section of the distal valve actuator during activation, the actuation or activation end of the distal actuator does not extend too far proximally of a plane defined by the valve disc of the valve. This configuration can ensure that the valve is pushed back in the proximal direction by the flaps as the flaps return to their more relaxed state when the male Luer implement is removed.

A conical configuration at a nose section of a distal valve actuator can be such a configuration, which can maintain an axial directed force vector that is greater than a perpendicular force vector. The angle of the cone can be designed to provide the necessary force vectors when the distal actuator has reached its maximum proximal movement and its minimum proximal movement. The difference between the maximum movement and minimum movement of a standard Luer connector is approximately 2.5 millimeters. Thus, current and future ISO standards for a male standard Luer connector can be consulted or considered in designing the angle of the cone of the distal actuator to ensure separation between the valve and the distal valve actuator.

Alternatively or additionally, a resilient element, such as a spring or an elastic element or ring, can be incorporated at a distal cavity chamber of the catheter hub to increase the re-coil or returning forces of the valve to facilitate pushing the valve and the proximal valve actuator in the proximal direction and away from the distal valve actuator following removal of the male tip to return to the pre-activated position or valve closed position.

The resilient element, which can be an elastic element or a helical spring, can also help to close the flaps of a valve disc. In this manner, the valve can be re-closed and the proximal valve actuator can return to the proximal position after the initial activation and re-open and so forth, repeatedly. Alternatively or additionally, the flaps of a valve can be made thicker to provide sufficient restoring forces without the need for a resilient element to close the valve following activation.

A combination structure can be provided. The combination structure can have a bushing end and an actuator end. The combination structure can be called a bushing or a distal valve opener.

In an example, the bushing end of a combination structure can have a sleeve and a base, which can have a funnel shape, for wedging a proximal end of a catheter tube against an interior of a catheter hub. The valve actuator end can comprise a base, a shoulder, a leg extension, and a nose section, which can be similar to the valve actuator.

In an example, a combination structure, which can alternatively be called a bushing or a valve actuator, can be unitarily formed from a metal material, such as by deep draw methods. Alternatively, the combination structure can be formed from two or more separately formed components that are subsequently attached to one another, such as by crimping or welding.

When a combination structure is inserted into a catheter hub to secure a catheter tube, the base of the bushing end can wedge against a shoulder inside a bore of the nose section and the base of the actuator end can wedge against the internal surface of the bore.

The nose section of a proximal valve opener can define a first continuous perimeter section. Other locations of the nose section, away from the first continuous perimeter section, can comprise a slit or a slot.

Two stabilizer elements can attach to two plunger elements to form a stabilizing ring. The stabilizing ring can define a second continuous perimeter section of a proximal valve actuator and can have a bore.

Each stabilizer element can comprise two edges. In an example, the two edges of each stabilizer element can be parallel to one another. The stabilizer elements can be skewed or slanted so that while two edges of each stabilizer element can be parallel to one another, the two edges from one stabilizer element can be non-parallel to the two edges of the other stabilizer element.

The proximal edges of two stabilizer elements can be offset along an axial direction or lengthwise direction of a valve actuator. The distal edges of the two stabilizer elements can be offset along an axial direction.

Two reliefs or two through passages can be provided on a valve opener, each defined or bounded by a first continuous perimeter section, two plunger elements, and a stabilizing ring. The two reliefs or through passages may be referred to as a first relief or first through passage and a second relief or second through passage. In an example, each relief or through passage can have a perimeter.

In an example, each perimeter of a relief can be defined by the structure of a continuous perimeter section of a nose section, two plunger elements, and a respective stabilizer element.

As two stabilizer elements can skew or slant in different directions, the two perimeters of two reliefs or through passages can be different, such as having different perimeter contours or shapes.

Two perimeters of two reliefs can each be defined by a continuous loop. In other words, in the present disclosure, the perimeters of two reliefs do not have to include a slit or a slot to form an open perimeter. However, where a stabilizer element includes a slot or a slit, the perimeter of a relief can be an open perimeter or a non-continuous perimeter.

In some examples, two stabilizer elements can extend laterally without skewing or slanting in a distal direction or a proximal direction. When so configured, the edges of the two stabilizer elements can be parallel to one another. Additionally, the four edges of a two stabilizer elements can be parallel to one another and axially offset. That is, the proximal edge of one stabilizer element can be located more proximally or distally that the proximal edge of another stabilizer element while the four edges are parallel to one another. One or more holes can be incorporated with the stabilizer elements and/or the plunger elements for manufacturing purposes, such as for core pins.

Two plunger element stubs or extensions can extend proximally of a stabilizing ring. In an example the two plunger element stubs can extend from the stabilizing ring and axially align with the plunger elements located distally of the stabilizing ring. In other examples, the two plunger element stubs are not axially aligned with the two plunger elements located distally of the stabilizing ring. In still other examples, only one plunger element stub aligns with one of the two plunger elements.

For a valve opener or actuator with only one plunger element between the first and second continuous perimeter sections, only one of the two plunger element stubs or none of the plunger element stubs can align with the one plunger element.

In some examples, there can be more than two plunger element stubs or extensions extending proximally of a stabilizing ring. The two or more plunger element stubs or extensions can be equally spaced around the proximal periphery of the stabilizing ring or randomly spaced around the proximal periphery of the stabilizing ring. The plunger element stubs can extend the overall length of a valve actuator.

The number of plunger element stubs and/or the arc-curve of each plunger element stub, which can define a width of each plunger element stub, can provide a greater overlapping surface with a male Luer tip than fewer numbers or for a plunger element stub with a relatively smaller arc-curve.

The plunger elements can each include a projection on an outside surface of each plunger element. The two projections can be located inside a recessed section of a catheter hub so that a shoulder at a proximal end of the recessed section can provide a stop surface to prevent dislodgement of the valve opener in the proximal direction.

In some examples, only one projection is employed on one of the two plunger elements of the actuator to prevent dislodgement of the valve opener in the proximal direction. The projection can be formed by adding material to the plunger element during injection molding at the site of the projection.

A holding space can be located between two plunger elements, inside the stabilizing ring, between two plunger element stubs, or combinations thereof.

Part or all of a needle guard or tip protector can be located in a holding space in a ready to use position and one or two elbows of a tip protector can project out one or two relief.

The distance between two inside surfaces of the two stabilizer elements can define a choke gap, choke point, or restricting point for a needle guard to limit proximal movement of the needle guard in a ready to use position and/or during retraction of the needle following intravenous access. That is, before the needle tip moves proximally of one or two distal blocking walls of a needle guard, the choke point or gap can be sized relatively small for the needle guard to pass proximally of the choke point or restricting point.

After the needle tip of a needle moves proximally of one or two distal blocking walls of a needle guard, the two distal walls move radially inwardly to decrease the needle guard's radial profile, which can be smaller than the choke point. At that point, with a smaller radial profile measured at the two elbows of the needle guard, the needle guard can move proximally of the choke point.

In an example, two edges of each stabilizer element can be parallel to one another. The two edges from one stabilizer element can also parallel to two edges of another stabilizer element.

The proximal edges of two stabilizer elements can be aligned along an axial direction or lengthwise direction of the valve actuator. The distal edges of two stabilizer elements can also aligned along an axial direction. In other examples, the edges of two stabilizer elements can be offset axially.

In some examples, rather than a single stabilizer element, two stabilizer segments having a slit or slot therebetween can be used.

The valve opener of the present embodiment can be made from a metal material. For example, a stamped metal sheet, such as a stamped stainless steel sheet, can be cold worked using deep draw methods to form the shape shown. The various openings or gaps of the actuator can be punched or stamped and then cold worked to form the disclosed shaped.

Each plunger element of a valve actuator can comprise at least two lengthwise edges and a rib can be provided along one or both of the lengthwise edges to further add structural rigidity. One or more gaps can be provided between any two plunger elements. The gaps can provide clearance or space for fluid flow flowing thereacross, such as during IV infusion. The gap can also be utilized to accommodate a needle guard.

The plunger elements can each comprise a projection on an outside surface of each plunger element. The projections can be located inside a recessed section of a catheter hub so that a shoulder at a proximal end of the recessed section can provide a stop surface to prevent dislodgement of the valve opener in the proximal direction. In an example, each projection can be formed by cold-working a surface of a stamped metal sheet at the respective plunger element to push out a protruding surface.

The nose section of a valve opener can neck down with two radiused sections and flow into plunger elements.

Each plunger element can extend in a proximal direction with a generally constant width and then necks up with a second set of radiused sections, which can transition into the stabilizer segments.

A pair of radiused sections can be located proximally of a stabilizer segments to form plunger element stubs. The plunger elements and the plunger element stubs can both have two spaced apart lengthwise edges, which can be provided with ribs to add strength to the respective structure.

From about within a bore of a stabilizing ring and extending in a proximal direction, each plunger element stub can bulge outwardly with an outward bulging portion relative to the lengthwise axis to form curved surfaces along the cross-section of each stub. The bulging portion can also be formed inwardly to form an inward bulging portion. This feature can be included to form the concave and convex surfaces for the plunger element stubs.

A valve actuator of the present disclosure can include a nose section formed by folding a wall layer to produce a folded section.

An end surface of a folded layer can terminate roughly between the nose section and the stabilizing ring of the valve actuator. In an example, the end surface can be located closer to the stabilizing ring than the nose section but the final location is not so limited. In an example, the end surface can define a shoulder on each of the two plunger elements. The two shoulders can provide similar functions as the projections on the valve actuators described elsewhere herein for use with a recessed section of a catheter hub.

In an example, cut-outs or notches can be provided at a folded edge of a nose section of a proximal valve actuator. Optionally, the notches can be omitted. The notches can be provided to permit flow-through, such as for flushing and reducing or eliminating fluid stagnation. In an example, eight equally spaced apart notches can be provided at the folded edge. In other examples, fewer or more than eight notches can be provided and the notches can be randomly spaced along the folded edge.

BRIEF DESCRIPTION OF THE DRAWINGS

These and other features and advantages of the present device, system, and method will become appreciated as the same becomes better understood with reference to the specification, claims and appended drawings wherein:

FIG. 4 is a schematic cross-sectional side view of the catheter assembly of FIG. 1 in which the catheter hub is now connected with a male Luer and the proximal valve actuator advanced by the male Luer to push the valve into a distal valve actuator to open the valve.

FIGS. 5A and 5B show an end view and a cross-sectional side view, respectively, of a proximal valve actuator in accordance with aspects of the present disclosure.

FIG. 8A is a front view of an exemplary single slit disk valve.

FIG. 8B is a front view of an exemplary three slit disk valve.

FIG. 8C is a front view of a single slit disk valve with v shaped slits at each end of the single slit.

FIG. 9 is an exploded perspective view of a needle assembly in accordance with aspects of the present disclosure.

FIG. 15 is a perspective view of a valve actuator embodiment.

FIG. 16 is a perspective view of another valve actuator embodiment.

FIG. 17 is a partial cross-sectional side view of a needle assembly having a valve actuator of FIG. 16, shown without a needle for clarity.

FIGS. 18A-18D are different views of the valve actuator of FIG. 9.

FIG. 19A-19D are different views of another valve actuator embodiment.

FIGS. 20A-20B are different views of another valve actuator embodiment.

FIG. 21A-21C are different views of the valve of FIG. 9.

DETAILED DESCRIPTION

The detailed description set forth below in connection with the appended drawings is intended as a description of the presently preferred embodiments of catheter assemblies with control valves provided in accordance with aspects of the present devices, systems, and methods and is not intended to represent the only forms in which the present devices, systems, and methods may be constructed or utilized. The description sets forth the features and the steps for constructing and using the embodiments of the present devices, systems, and methods in connection with the illustrated embodiments. It is to be understood, however, that the same or equivalent functions and structures may be accomplished by different embodiments that are also intended to be encompassed within the spirit and scope of the present disclosure. As denoted elsewhere herein, like element numbers are intended to indicate like or similar elements or features.

Figure 1:
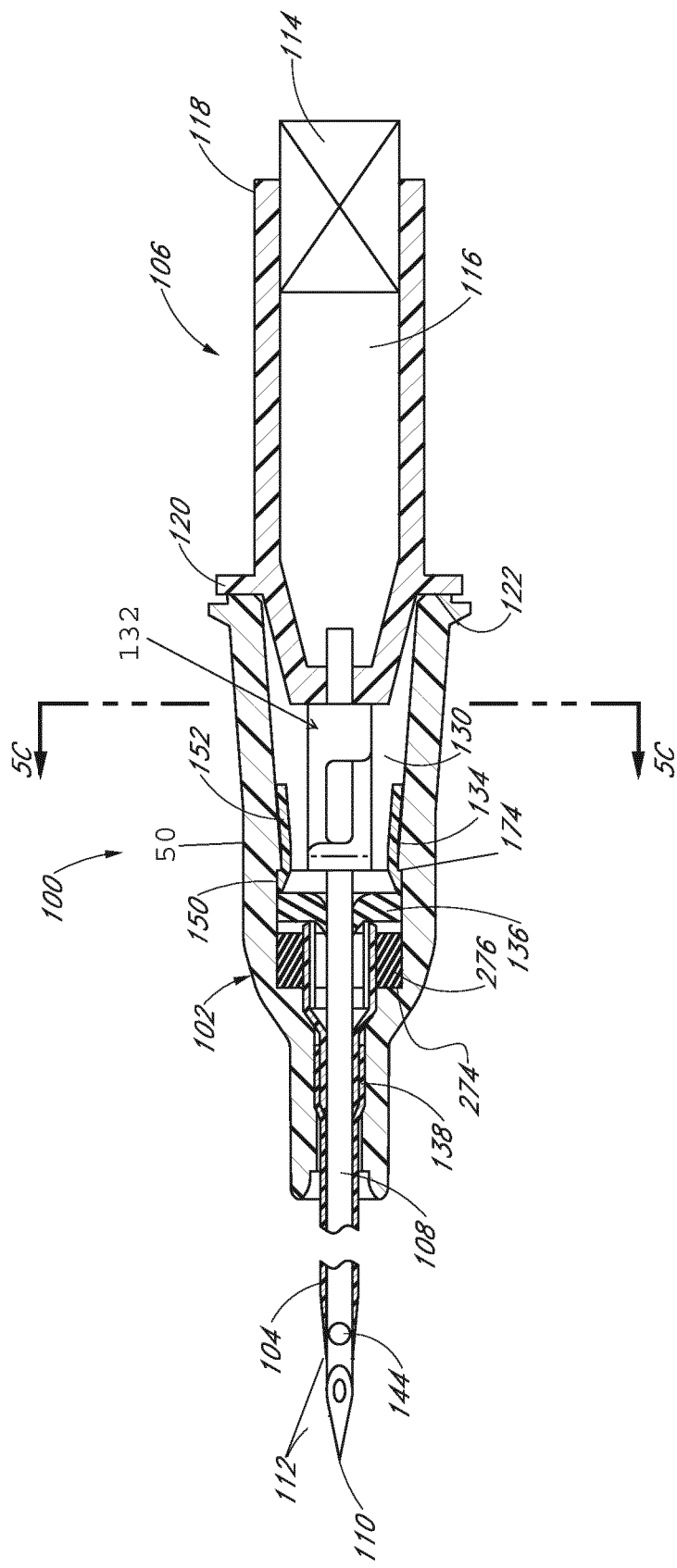
FIG. 1 is a schematic cross-sectional side view of a catheter assembly in a ready position in which the needle tip extends out a distal end of a catheter tube.

With reference now to FIG. 1, a catheter assembly 100, which may more broadly be referred to as a needle assembly or a needle device, is shown comprising a catheter hub 102 with a catheter tube 104 attached to the hub body 50 and a needle hub 106 with a needle 108 extending through the catheter hub 102 and the catheter tube 104 with the needle tip 110 extending out a distal end or distal opening 112 of the catheter tube in a ready to use position. In the ready position, the catheter assembly 100 is ready for use, such as to perform a venipuncture or intravenous access. Sometimes the ready position first requires removing a protective cap (not shown) from the catheter assembly or needle assembly 100.

A flash back plug 114 can be provided at the proximal end 118 of the needle hub 106, which allows air to vent but stops blood from spilling out the proximal end 118 when entering the flashback chamber 116 during primary flashback. Alternatively, a syringe can be attached to the proximal end of the needle hub. The valve and actuator described further below can also be placed within the needle hub as a second valve. The needle hub 106 further comprises a shoulder 120 or other surfaces that physically contact the catheter hub 102, such as the proximal end surface 122 of the catheter hub, to axially register the two hubs 102, 106 to set the length of the needle tip 110 projecting out of the distal opening 112 of the catheter tube 104.

Interiorly of the catheter hub 102, in the interior cavity 130, a needle guard or tip protector 132, a valve opener or actuator 134, a valve 136, and a bushing 138 are provided. The proximal opening of the catheter hub 102 can be sized with a female Luer taper. The bushing 138 has a base that is configured to wedge the proximal end of the catheter tube 104 against the interior wall surfaces of the catheter hub 102 to retain the catheter tube 104 to the catheter hub 102.

The tip protector 132 may embody any number of prior art guards configured for blocking the needle tip 110 of the needle. In the exemplary embodiment shown, the tip protector 132 can embody one of the guards shown in U.S. Pat. No. 6,616,630, the contents of which are expressly incorporated herein by reference. For example, the tip protector 132 can have a proximal wall and two resilient arms and wherein a change in profile 144 on the needle 108, such as a crimp or a bulge, engages a perimeter defining an opening on the proximal wall of the tip protector 132 to retract the tip protector in the proximal direction out of the catheter hub following successful venipuncture. The two arms can intersect as described in U.S. Pat. No. 6,616,630 and shown in FIG. 7 or they can run along different sides of the needle and do not intersect along a side view. The needle guard arms are spread by the needle shaft in a ready position and engage the inside of the catheter hub, such as the guard engagement section 210 (FIG. 3) of the catheter hub 102. In an example, only part of the tip protector or needle guard 132 can extend into one or more gaps of the valve opener 134 while the proximal section of the tip protector, such as the proximal wall, can extend proximally or be located proximally of the proximal most surfaces of the tip protector 132.

When the needle tip 110 is pulled into the needle guard 132 following successful venipuncture, the arms of the needle guard collapse to their protecting position to block accidental access to the needle tip. At the same time, the engagement of the arms with the inside of the catheter hub is released. The same working can also be achieved by one of the one armed needle guards described in U.S. Pat. No. 6,616,630, which runs along a side the needle shaft, instead of crossing the needle as shown in some of the embodiments of the '630 patent. Likewise the distal wall of the one arm is pushed aside by the needle shaft in the ready position. When the needle tip 110 is moved proximal of the distal wall, then the distal wall springs in front of the needle tip to block accidental access to the needle tip and at the same time the engagement between the needle guard and the inside of the catheter hub is released.

FIG. 5A shows a front view of a valve opener or actuator 134 and FIG. 5B shows a cross-sectional side view of the same valve opener taken along line 5B-5B of FIG. 5A. With further reference to FIG. 1, the valve opener 134 can comprise a ring 150 and at least one plunger element 152, such as a leg element or an elongated extension. The ring 150 is shown in contact with the valve 136 in the needle assembly ready to use position of FIG. 1 but can be slightly spaced from the proximally facing surface of the valve. In an exemplary embodiment, two plunger elements 152 can extend from the ring 150 in the proximal direction and each having a length measured in a lengthwise direction of the catheter assembly and a width, measured orthogonally to the length. The at least one plunger element 152 is sized and shaped for contact by a male Luer to transfer a distally directed force from the male Luer to the ring 150 to then open the valve 136, as further discussed below.

As can be visualized from the front view of FIG. 5A and the side view of FIG. 5B, the at least one plunger element 152 can have an arc shape or arc cross section along a width. In another example, the at least one plunger element 152 can be generally flat or planar. The thickness of each of two plunger elements 152 is sufficiently small or thin so that the needle guard 132 and the two plunger elements 152 have sufficient clearance to fit within the interior cross-sectional space of the catheter hub 102 without being physically binding against the catheter hub and rendered unmovable or fixed. In an example, the thickness of each of two plunger elements 152 and the width of the needle guard are such that no undercut or channel is required to be formed in the interior wall surfaces of the catheter 102 hub to accommodate them. When the plunger element 152 has an arc cross section, it will be mechanically stronger to take a greater load when being pushed by a male tip to push the ring 150 against the valve 136. This allows a thin and compact design for the infusion device and gives more room in the standardized space of a female Luer taper.

The valve opener 134 can be made from a metal material or from a plastic material. When made from a metal material, the valve opener 134 can be formed by deep draw methods and the arc shape cross section of the plunger element 152 can provide added rigidity when pushed by the male Luer. Each plunger element 152 comprises at least two lengthwise edges and a rib can be provided along one or both of the lengthwise edges to further add structural rigidity. One or more gaps 154 can be provided between any two plunger elements 152. The gaps 154 can provide clearance or space for fluid flow flowing thereacross, such as during IV infusion. The gap 154 can also be utilized to accommodate a needle guard 132, as shown in FIG. 1.

The ring 150 of the valve opener 134 comprises a body 158 with an outer perimeter 160. In an example, the outer perimeter 160 is generally cylindrical. In other examples, the outer perimeter can have a taper. Interiorly, the body 158 comprises a chamfer 162 and an opening 164. The distal edge or intersection 166 of the body 158 between the chamfer 162 and the outer perimeter 160 can have a sharp edge or a blunt edge. In an example, the intersection is a blunt edge comprising a planar surface for pushing against the valve 136, as further discussed below. On the proximal side of the ring 150, the two plunger elements 152 can be recessed inwardly from the outer perimeter 160 to form a shoulder 170. Said differently, the outer perimeter 160 can have an outside diameter of a first dimension and the two plunger elements 152 can define an outside diameter of a second dimension, which is smaller than the first dimension. A shoulder 170 is provided between the two different dimensions.

The valve opener 134 has an inside diameter measured adjacent the intersection 166. The inside diameter changes or varies along the chamfer 162 section of the ring 150. The valve opener 134 further has a minimum inside diameter mID, which can be viewed as the smallest inside diameter of the valve opener. As shown, the minimum inside diameter mID can be located at a corresponding inside location of the shoulder 170. In other examples, the minimum inside diameter mID can be located at other interior locations of the valve opener 134, such as somewhere inside the ring 150 or somewhere between the plunger elements 152.

Figure 5C:
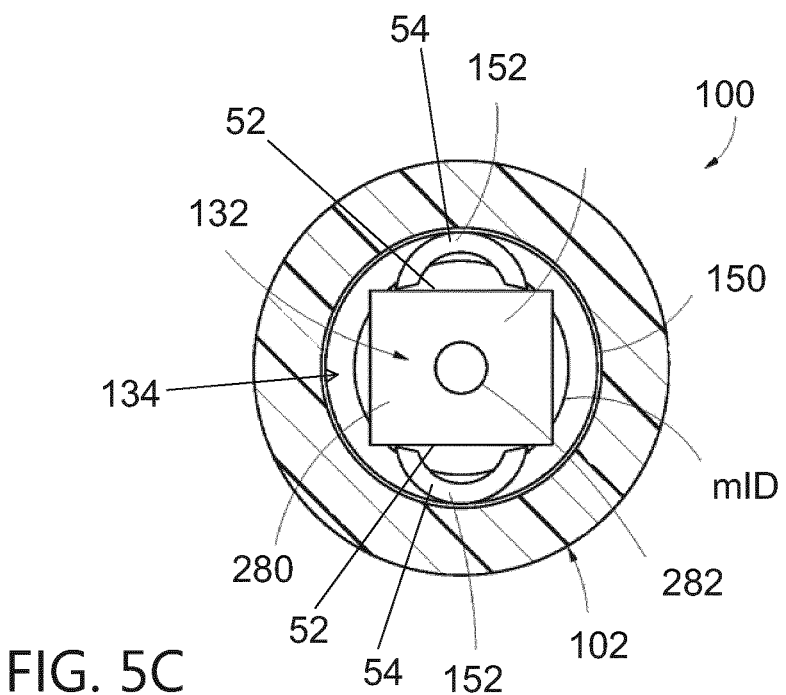
FIG. 5C shows a cross-section end view taken along line 5C-5C of FIG. 1, which shows the needle guard and inwardly arc-shaped plunger elements of the proximal valve opener.

FIG. 5C is a cross-sectional end view of the needle assembly 100 of FIG. 1 taken along line 5C-5C and shown without the needle 108. FIG. 5C shows the proximally facing wall surface of the proximal wall 280 of the needle guard 132 and two plunger elements 152. As shown, the needle guard 132 is located between one or more gaps defined by the two plunger elements 152 and the proximal wall 280 extends proximally of the proximal most edges of the valve opener 134. As previously alluded to, the plunger elements 152 can each comprise an arc-shape cross section. As shown, the arc-shape cross section of each plunger element 152 is generally C-shaped with the concave portion facing internally towards the needle guard 132 and the convex portion facing outwardly away from the needle guard 132. The arc-shape cross section of the two plunger elements 152 should have a radius of curvature that is different than the radius of the female Luer of the catheter hub 102, such as a smaller radius of curvature than the female Luer of the catheter hub. The radius of curvature of the two C-shaped plunger elements should also be different than the radius of a male Luer tip. A gap can be provided on each side edge 52 of the proximal wall 280 and the adjacent plunger element 152.

The present configuration of the valve opener 134 allows the two plunger elements 152 to define an abutting proximal surface 54 that is sized and shaped to be pushed against by a male Luer tip or a syringe tip when said tip is inserted into the proximal opening of the catheter hub 102 following successful venipuncture to push the valve opener 134 distally to open the valve 136. The arc-shape cross section of each of the two plunger elements 152 provides a sufficiently thick profile to ensure overlapping abutting surfaces with the male Luer tip and rigidity from buckling. Consequently, the C-shaped plunger elements can avoid deflection when pushed by a syringe tip or other male Luer tip, avoid slippage of the syringe tip or Luer tip missing the end surfaces 54 of the plunger elements 152 when the syringe tip or Luer tip is inserted into the open proximal end of the catheter hub, and/or avoid a situation in which the syringe tip or Luer tip is pushed between the two plunger elements to wedge the two plunger elements between the tip and the interior surface of the catheter hub 102 during activation of the valve opener 134.

Figure 5D:
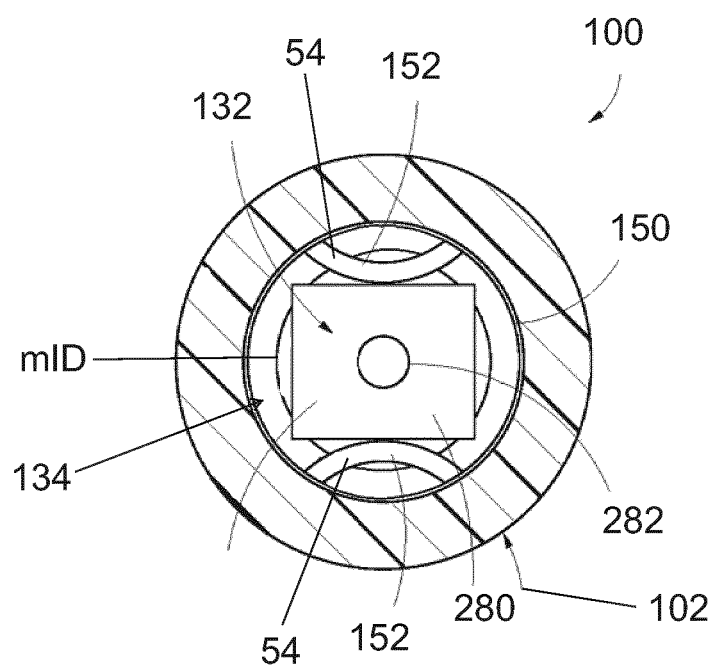
FIG. 5D is an alternative embodiment of the valve opener of FIG. 5C, showing outwardly arc-shaped plunger elements.

FIG. 5D shows the same cross-section end view of a catheter hub 102 as that of FIG. 5C but with an alternative arc-shape cross-sections on the plunger elements 152 of the valve opener 134. As shown, the two plunger elements 152 each comprises a C-shaped cross-section. However, in the present embodiment, the concave portion of the arc-shape cross-section of each plunger element 152 faces outwardly, away from the needle guard 132, while the convex portion of each plunger element faces inwardly towards the needle guard 132. Like the embodiment of FIG. 5C, the arc-shape cross-section of the two plunger elements 152 provide overlapping abutting surfaces with a syringe tip or Luer tip when the same is inserted into the catheter hub 102 to push the valve opener 134 into the valve to open the valve following successful venipuncture.

When mounted inside the interior cavity 130 of the catheter hub 102, the ring 150 of the valve opener 134 is elastically deformed and then expands when it reaches a recessed hub section 174 of the catheter hub 102, which can accommodate the ring without deforming the ring. Alternatively, the catheter hub 102 is designed to expand to allow the assembly of the valve opener 134. A shoulder 176 (FIG. 4) is provided at the recessed hub section 174, which forms a physical stop for engaging the shoulder 170 on the valve opener 134. This allows the valve opener 134 to be retained within the interior cavity 130 of the catheter hub 102 during needle withdrawal and during use, when the valve opener 134 is pushed distally to activate the valve and subsequently moves proximally when the male Luer is removed, thus allowing the valve to close.

With reference again to FIG. 1, the valve 136 is located inside the catheter hub 102 just distal of the ring 150 of the valve opener 134. In an example, the valve 136 embodies a valve disc 137 comprising a valve body comprising a valve diameter, a valve thickness measured orthogonal to the valve diameter, and one or more slits defining two or more flaps. In a particular example, three slits are provided through the valve thickness to define three flaps. The three slits can originate from a point and extend radially from about a center point or central portion of the body of the valve 136, similar to a three-point star, to form three flaps that can deflect along the slits. The valve 136 can comprise an outer perimeter that can float inside the interior cavity of the catheter hub, between the valve opener 134 and the bushing 138. For example, the outer perimeter of the valve 136 can move proximally and distally within the interior cavity 130 of the catheter hub 102 and not be restrained by the catheter hub along an axial direction of the catheter assembly. The outer perimeter of the valve 136 can be the same or smaller or larger than the outer perimeter of the ring 150 of the valve opener 150. However, at least some part or all of the distal edge or intersection 166 of the ring 150 is recessed from the outer perimeter of the valve 136 so that the distal edge 166 can abut or touch the proximally facing wall surface of the valve 136, as further discussed below. Also, since the valve 136 can float, the valve can be positioned inside a single hub body catheter hub 102. In other words, the valve 136 does not have to be retained inside a catheter hub by two or more catheter hub bodies, such as along a seam of two or more hub bodies. However, the various components described herein may readily be used with a multi-piece catheter hub without deviating from the scope of the present disclosure.

Figure 6A:
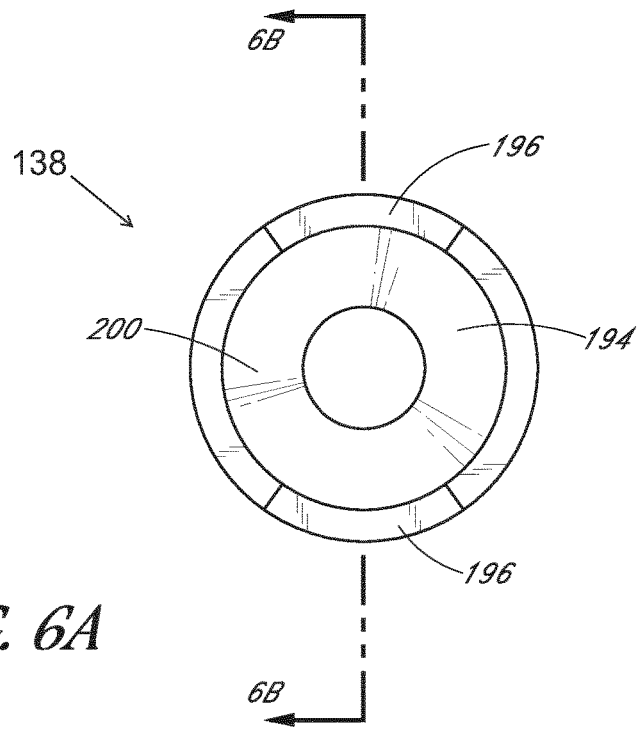
FIGS. 6A and 6B show an end view and a cross-sectional side view, respectively, of a distal valve actuator in accordance with aspects of the present disclosure.
Figure 6B:
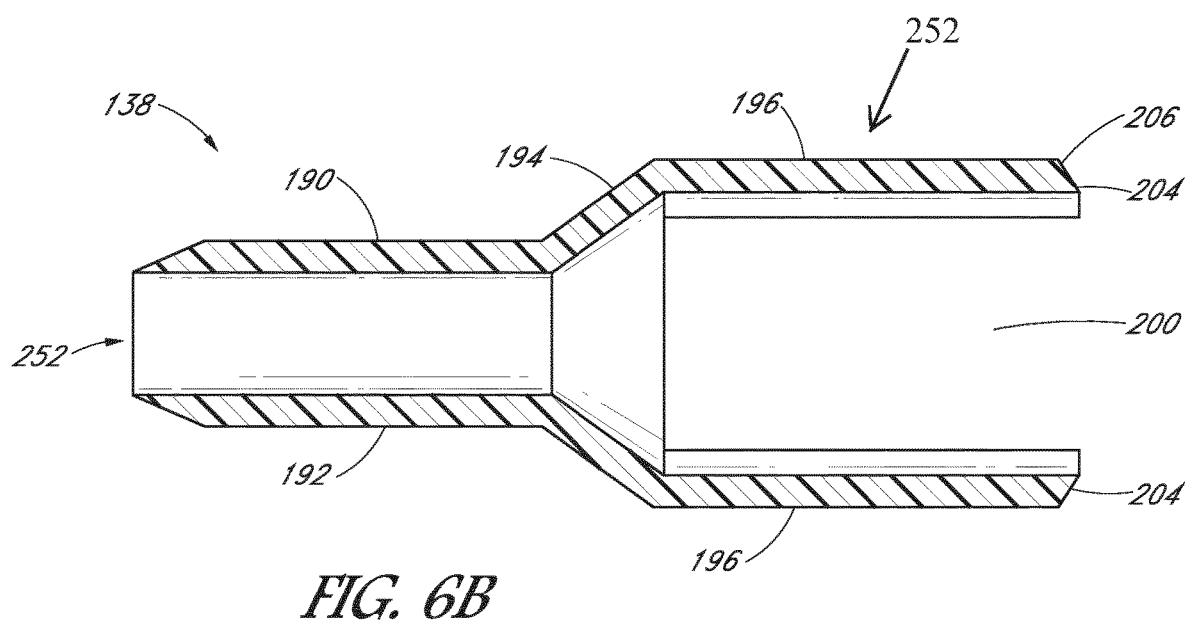

FIG. 6A shows an end view of a bushing 138 and FIG. 6B shows a cross-sectional side view of the same bushing taken along line 6B-6B of FIG. 6A. With further reference to FIG. 1, the bushing 138 comprises a body 190 comprising a first body section 192, a second body section 194 extending from the first body section 192 having a cone shape, and two or more leg extensions 196 extending from the second body section 194. The first body section 192 can have an elongated body that can have a cylindrical shape with an optional tapered distal tip or nose section. In some examples, a generally cylindrical ring extends from the second body section 194 and the two or more leg extensions 196 extend from the cylindrical ring. One or more gaps 200 are provided between two adjacent leg extensions 196. In an example, the number of leg extensions 196 incorporated with the bushing 138 is the same as the number of flaps incorporated with the valve 136. Thus, if the valve has three flaps, then there can be three leg extensions 196 on the bushing 138. If the valve 136 has a single slit, then there can be two leg extensions 196. The leg extensions 196 on the bushing 138 can define an outside diameter that is smaller than the minimum inside diameter mID of the valve opener 134. The proximal tip or nose section 204 of each leg extension 196 can have a chamfer or a blunt tip. In one example, a chamfer 206 is incorporated at the proximal tip or nose section 204 of each leg extension 196 and wherein the chamfer 206 tapers inwardly from the exterior of the leg extension 196. This chamfer direction is configured to match the folding direction of the flaps on the valve 136. The bushing 138 can be made from a metal material and the leg extensions 196 can be unitarily formed with the body 190. Alternatively, the leg extensions 196 can be welded to the body 190.

When positioned in the catheter hub 102, the bushing 138 and the valve 136 are oriented so that the leg extensions 196 on the bushing are aligned with the flaps on the valve. In other words, the two components are aligned so that when the valve 136 is advanced distally by the valve opener 134 from the proximal side, as further discussed below, the flaps on the valve are pushed into physical contact with the leg extensions 196 on the bushing 138. Thus, if there are three flaps on the valve, the three flaps will be pushed into physical contact with three leg extensions on the bushing. The distally facing wall surface of the valve 136 can touch the leg extensions and/or the elastic element 276 or be spaced from the leg extensions 196 on the bushing 138 and/or the elastic element 276 in the valve closed position and be pushed against the leg extensions during use. In other examples, the valve can touch the proximal tips of the leg extensions and/or the elastic element 276 in the closed position of the valve or be spaced therefrom.

Figure 2:
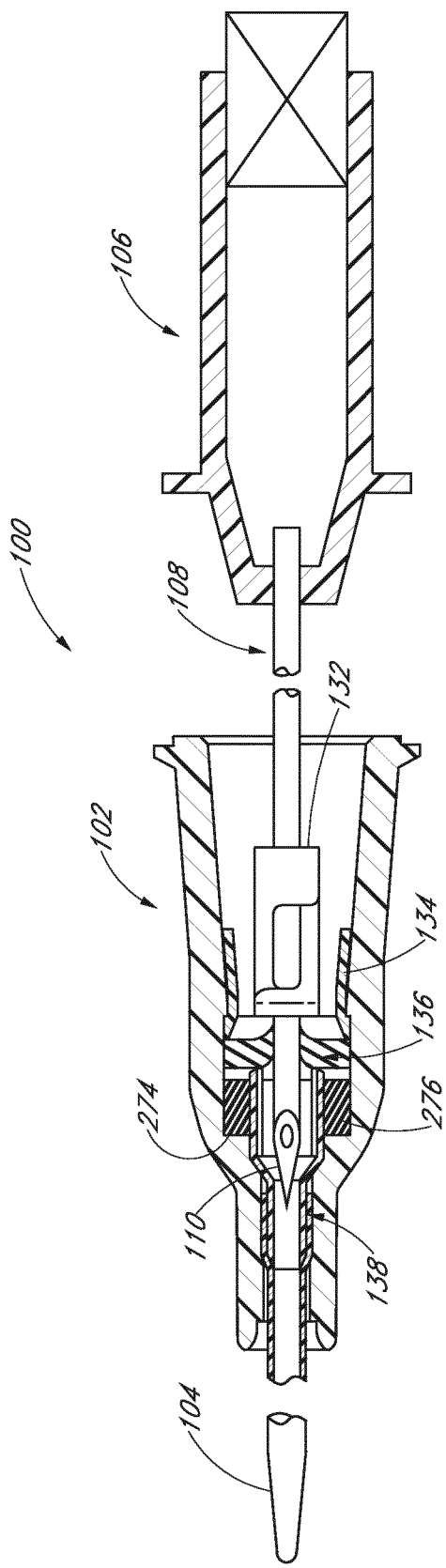
FIG. 2 is a schematic cross-sectional side view of the catheter assembly of FIG. 1 in a transition position or state in which the needle is in the process of being removed from the catheter tube and the catheter hub, such as following successful venipuncture.
Figure 6C:
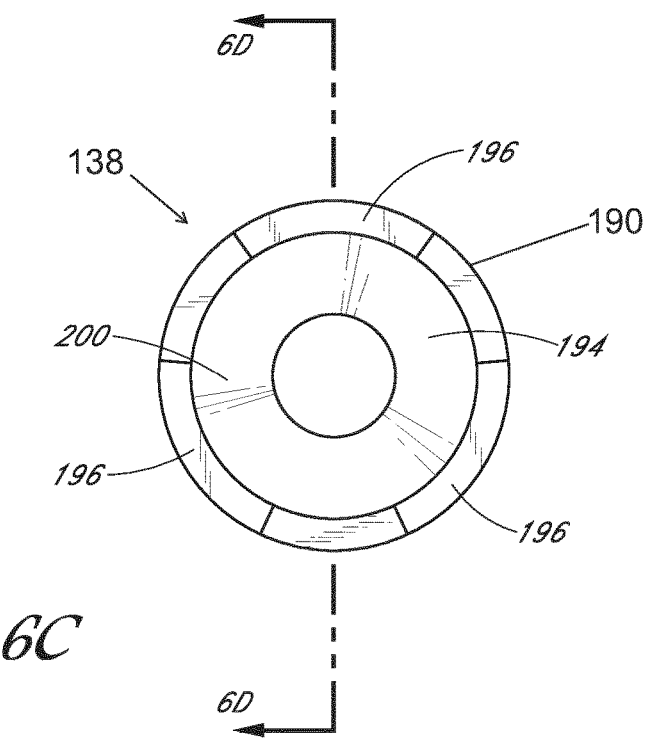
FIGS. 6C and 6D show an end view and a cross-sectional side view, respectively, of an alternative distal valve actuator having three fingers or plunger elements for use with a valve having three lugs.
Figure 6D:
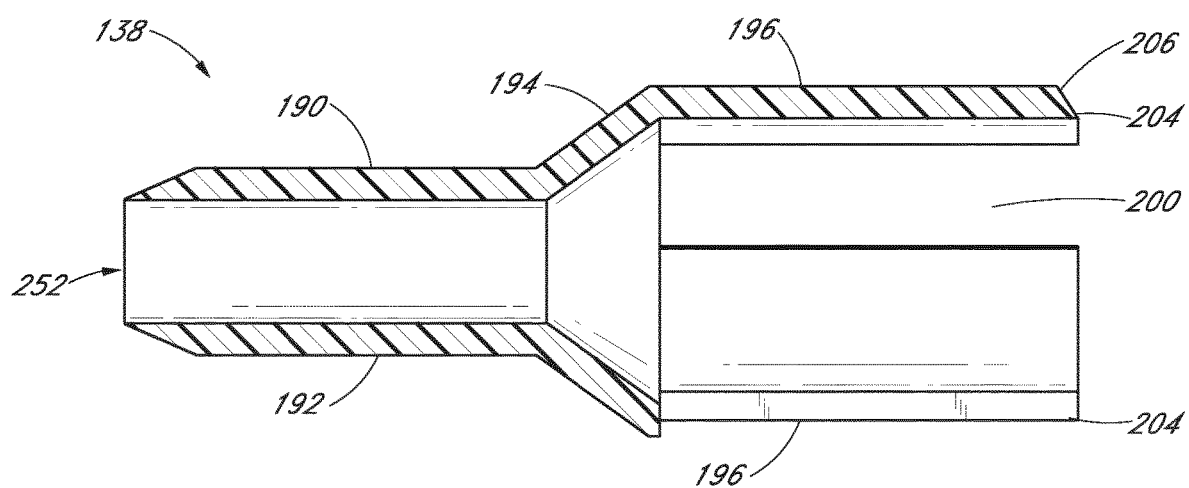

FIG. 6C shows an end view of an alternative bushing 138 and FIG. 6D shows a cross-sectional side view of the same bushing taken along line 6D-6D of FIG. 6C. Like the bushing of FIG. 6A, the present embodiment comprises a body 190 comprising a first body section 192 and a second body section 194. In the present embodiment, three leg extensions 196 are provided for use with a valve comprising three slits defining three lugs, as previously alluded. The three leg extensions 196 can be equally spaced along a circumference of the second body section 194. In another example, the three leg extensions 196 can be located and spaced in accordance with the positions of the lugs on the valve 136 so that when assembled inside the catheter hub 102, the valve can be pushed distally by the valve opener or valve actuator 134 and the leg extensions 196 on the bushing 138 are aligned to push the lugs of the valve in the proximal direction to open the valve, as further discussed below. With reference now to FIG. 2, the catheter assembly 100 is shown in a transition position whereby the needle 108 is in the process of being separated from the catheter hub 102 and the catheter tube 104, such as following successful venipuncture. The needle tip 110 is shown just distal of the valve 136. During retraction of the needle 108 in the proximal direction, the tip protector 132 is held axially by the engagement between one or both resilient arms on the tip protector 132 and a guard engagement section 210 (FIGS. 3 and 4) on the catheter hub 102. In an example, the guard engagement section 210 is a surface discontinuity formed on the interior surface of the catheter hub 102. For example, the guard engagement section 210 can comprise a section of a first inside diameter and a section of a second inside diameter, which is larger than the first inside diameter. The guard engagement section 210 can embody an internal projection or a groove or a combination of both a groove and a projection formed on the interior surface of the catheter hub 102. When a combination of a groove and a projection is used for a guard engagement section 210 to engage the needle guard or tip protector 132, then it is preferred that the groove is distal to the projection. In an example, two spaced-apart guard engagement sections 210 are provided for engaging the two resilient arms on the tip protector 132. The two guard engagement sections 210 can be located diametrically opposed of each other just distal of the section of the female Luer taper of the catheter hub 102.

Figure 5E:
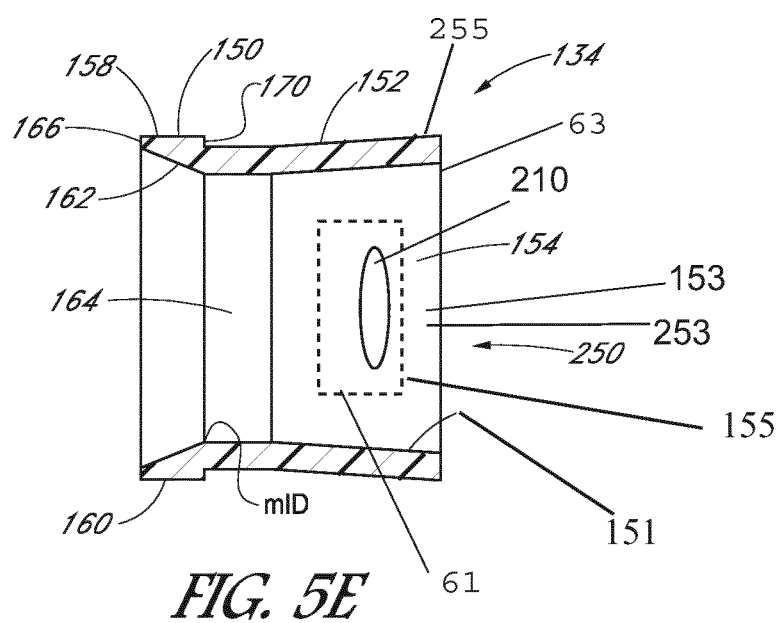
FIG. 5E shows an alternative embodiment of the valve opener of FIG. 5B, wherein the proximal section is a cylinder for surrounding at least part of a needle guard.

FIG. 5E shows a valve opener 134 provided in accordance to an alternative embodiment of the present disclosure. The present valve opener 134 is similar to the valve opener 134 of FIGS. 5A and 5B and comprises a nose section 150 with an activation end 166 and two plunger elements 152 extending in the proximal direction of the nose section 150. However, rather than incorporating two plunger elements 152 with two free ends, the present embodiment incorporates a band or ring connecting the two plunger elements 152 together. Two arc-shape, curved sections, or stabilizer elements 253 can attach to the two plunger elements 152 to form the band or ring 255. The band 255 can be called a stabilizing ring 255 and can connect the two plunger elements 152 together to form a stabilizing structure. The stabilizing ring 255 forms a continuous perimeter section of the valve actuator that is spaced from another continuous perimeter section defined by the nose section 150 of the valve actuator.

The present valve actuator embodiment 134 can also be viewed as a valve opener 134 with a single plunger element 152 extending from a nose section 150 and wherein the single plunger element 152 comprises two or more reliefs or through passages 61 formed through the wall of the plunger end. The needle guard 132 can engage the edges or perimeters of the reliefs 61 in the ready to use position and during retraction of the needle following successful venipuncture. Alternatively, the tip protector or needle guard 132 can project from the holding space defined by the valve opener 134 through the reliefs 61 to engage the interior surface of the catheter hub 102.

Thus, in the embodiment with two reliefs or through passages 61, the perimeters of the two reliefs or through passages can function as guard engagement sections 210 by allowing the elbows of the tip protector to engage thereto. Alternatively, the two elbows of the needle guard can project through the two reliefs from the holding space defined by the valve opener to engage the guard engagement sections or segments formed on the interior surface of the catheter hub. Thus, the perimeters of the reliefs or the interior surfaces of the catheter hub can form anchor points for the arms of the tip protector to engage thereto in the ready to use position and during retraction of the needle following successful venipuncture.

In an example, the single plunger element 152 of the valve opener 134 of FIG. 5E can embody a generally cylindrical body section 151 having an interior surface 153 defining a bore having a path or channel 154, which can also be a gap for fluid flow, and a proximal perimeter or end edge 63. At least part of the bore of the proximal valve opener 134 can define a holding space 155 for receiving part or all of a needle guard. A guard engagement section 210, similar to the guard engagement segment 210 shown in FIG. 4, can be formed on the interior surface 153 of the present valve opener 134. In other words, the projection, bump, recess or guard engagement section 210 can be formed on the interior wall surface 153 of the valve opener to allow engagement between the needle guard and the interior surface of the valve opener.

When the present alternative valve opener 134 of FIG. 5E is used with a needle device or catheter assembly 100, such as the assembly of FIG. 1, the guard engagement segment 210 can be on the catheter hub, on the interior wall of the valve opener, or a perimeter of a relief formed through the wall of the valve opener. There can be one or more reliefs or guard engagement segments incorporated with the valve opener. There can also be one or more guard engagement segments formed with the catheter hub for use with the one or more reliefs of the valve opener. This allows the two resilient arms of the tip protector 132 to engage the valve opener 134 or to engage the catheter hub by projecting through the reliefs.

In yet another example, two openings 61 shown in dashed-lines (only one shown) can be provided through the wall layer of the cylindrical body portion 151 of the valve opener for use with the guard engagement segment 210 formed with or on the interior of the catheter hub 102. In the ready to use position using the valve opener of the present alternative embodiment, the resilient arm or arms of the tip protector 132 can project through the opening 61, or through two openings 61, to engage the guard engagement segment(s) 210 of the inside of the catheter hub 102 instead of or in addition to engaging the opening 61 of the valve opener 134.

Figure 3:
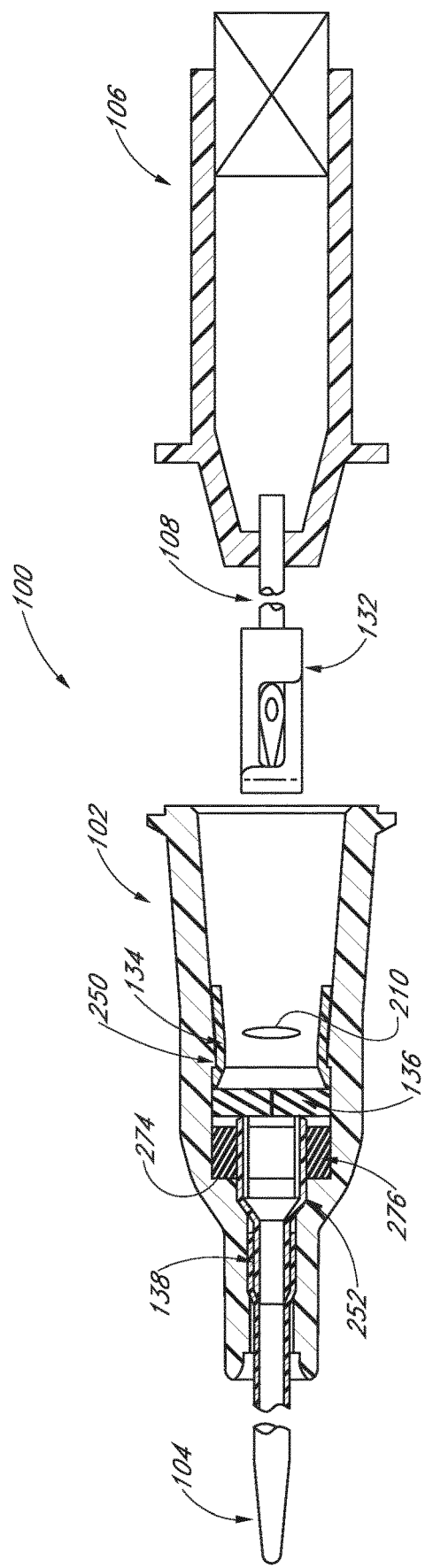
FIG. 3 is a schematic cross-sectional side view of the catheter assembly of FIG. 1 in which the needle has completely separated from the catheter hub and the needle tip is covered by a needle guard.

FIG. 3 shows the needle 108 completely removed from the catheter hub 102 and the tip protector 132 covering the needle tip 110 (FIG. 1) in a protective position. In transitioning from the position of FIG. 2 to the position of FIG. 3, the needle tip 110 moves proximally of two distal walls 300, 302 (FIG. 7), one on each end of the resilient arms 288, 290 (FIG. 7), of the tip protector 132. Alternatively, the needle guard 132 can have one distal wall and/or one arm. As the two distal walls and hence the two resilient arms are no longer biased outwardly by the needle 108, the two arms 288, 290 move radially to disengage from the two guard engagement sections 210 of the catheter hub 102, or of the valve opener 134 (FIG. 5E), if the latter is alternatively used. Alternatively, the one arm and one distal wall disengage from the one guard engagement section 210.

As the needle continues to move in the proximal direction and the change in profile 144 (FIG. 1) engages the perimeter 282 (FIG. 7) on the proximal wall of the tip protector 132, the tip protector 132 is moved proximally with the needle to the position shown in FIG. 3. Alternatively the needle guard can clamp onto the needle shaft and be removed from the catheter hub as a unit. Note that in the protective position in which the tip protector 132 covers the needle tip, the valve 136 remains inside the interior cavity of the catheter hub 102. Thus, the valve 136 is located inside the catheter hub 102 in both the ready position of the needle and the protective position of the needle. Viewed from another perspective, the valve 136 is located inside the catheter hub 102 in both the ready to use position of the catheter assembly 100, in which the needle tip projects out a distal opening 112 (FIG. 1) of the catheter tube 104, and a protective position of the catheter assembly, in which the needle is removed from the catheter hub and the needle tip is covered by a tip protector.

With reference now to FIG. 4, the catheter hub 102 is shown with a male medical implement 220 positioned in the proximal opening thereof. The male medical implement or instrument 220 can be a male Luer, a syringe tip, an IV set connector, or other male tip having a Luer taper. For example, the male medical implement can be connected to an IV tubing, which is connected to an IV fluid source for fluid delivery through the male medical implement 220, the catheter hub 102, and the catheter tubing 104 to deliver fluid therapy to a patient.

With reference to FIGS. 5A, 5B, 6A, 6B, and continued reference to FIG. 4, when initially inserting the male medical implement 220, herein male tip, into the proximal opening of the catheter hub 102, the male tip initially contacts the two plunger elements 152 on the valve opener 134 to advance a distally directed force on the two plunger elements 152 to open the valve 136. The arc cross section of the plunger elements 152 can have a smaller diameter than the inside diameter of the catheter hub 102 to provide a larger contact surface for the distal end of the male medical instrument 220, as previously discussed. This can also be designed to contact the inside wall of the catheter hub at a tangential point. In this way, the plunger elements 152 are stable and can resist being deflected outwards. This arrangement can avoid the relatively thin plunger elements from wedging between the male medical instrument 220 and the inside wall of the catheter hub 102. The distally directed force moves the valve opener 134 in the distal direction until the geometries of the male tip 220 and the proximal opening of the catheter hub stop further distal advancement of the male tip. In an example, a female Luer taper of the catheter hub 102 and a male Luer taper of the male tip 220 register and block distal advancement of the male tip further into the opening of the catheter hub. A seal is provided by the Luer engagement to prevent fluid from leaking out the proximal opening of the catheter hub.

As the valve opener 134 moves distally by the distal advancement of the male tip 220, the ring 150 is urged distally and pushes against the proximally facing surface of the valve 136. In particular, the distal edge 166 of the valve opener 134 initially pushes against the proximally facing surface of the valve 136. As the valve 136 is axially movable inside the catheter hub 102, the valve 136 is urged distally by the valve opener 134, which is urged distally by the male tip 220. For example, the ring 150 contacts and pushes the valve 136 in the distal direction. However, due to the presence of the leg extensions 196 on the bushing 138, the outer edges or outer valve sections of the valve 136 moves distally while other parts on the valve 136 that abut or contact the leg extensions 196 are stopped from moving distally by the leg extensions 196. In effect, the outer edges of valve 136, such as outer sections of the body of the valve 136, move distally while the flaps on the valve are deflected from a central point or location radially outwardly and in a proximal direction by the leg extensions 196 on the bushing 138 to open a flow path 226 through the valve. Fluid from the male tip 220 can then flow through the catheter hub 102, through the valve 136, and through the lumen of the catheter tube 104. Alternatively, a suction can be applied by the male medical instrument, such as a syringe or vacuum blood collection tube, and blood aspirated from the patient. This is often done for testing samples before infusion therapy is commenced. Also, typically any remaining blood is first flushed from the inside of the catheter hub 102 before infusion therapy is commenced.

With further reference to FIGS. 4, 5B and 6B, the chamfer 162 on the ring 150 and the chamfers 206 on the leg extensions 196 facilitate deflection of the flaps on the valve radially outwardly and in the proximal direction. Also, the relative diameters defined by the leg extensions 196 and the minimum inside diameter mID of the valve opener 134 allow the valve opener and the bushing to deflect the valve 136 therebetween to open the valve. Alternatively, the outer perimeter of the valve can remain in contact with the inside wall of the catheter hub, when pushed distally, with only the flaps opening around the slit or slits.

Thus, an aspect of the present disclosure is understood to include a catheter assembly comprising a valve comprising one or more slits and two or more flaps wherein the valve comprises parts or sections that move in a distal direction and parts or sections that open along a radial direction and in a proximal direction to open a flow path through the valve. In an example, outer edges of the valve are configured to move distally while the flaps of the valve are configured to move radially outwards to open a flow path through the valve. Also, by incorporating a valve that can move in this fashion to open a fluid flow path, the actuation distance that the valve opener 134 has to travel in the axial direction of the catheter assembly is minimized compared to a valve having flaps that only open in the distal direction by a valve opener. Thus, the size of the catheter hub 102, such as the length of the catheter hub, can be reduced compared to one that utilizes a valve and a valve opener that opens the valve by deflecting the valve flaps only in the distal direction.

A further aspect of the present disclosure is understood to include a catheter assembly comprising a valve and wherein the valve perimeter can float in the axial direction relative to the catheter hub. In other words, by incorporating a valve with a valve perimeter that can float in the axial direction, a two-part catheter hub is not required to secure the valve perimeter therebetween and inside the catheter hub. Therefore, a catheter hub with a singularly formed hub body may be used with the present catheter assembly. Thus, the size of the catheter hub 102, such as the outer diameter or dimension of the catheter hub, can be reduced compared to one that utilizes a two-part hub body. The two part hub body where they join along a seam can thus be reduced to provide a catheter assembly with a relatively smaller outer profile.

A still yet further aspect of the present disclosure is understood to include a valve opener 134 for opening a valve 136. The valve opener 134 is configured to push the valve against another structure, such as the leg extensions 196 on the bushing 138. The present valve opener 134 may be viewed as having a multi-piece valve opening structure. For example, the part with the ring 150 and the plunger elements 152 may be viewed as a proximal valve opener 250 and the bushing 138 with the leg extensions 196 may be viewed as a distal valve opener 252. The bushing 138 and the distal valve opener 252 can be unitarily formed.

The two valve openers 250, 252 cooperate to open the valve 136. As described, the proximal valve opener 250 is sized and shaped to push against the outer edges of the valve 136 in the distal direction to move the valve against the distal valve opener 252. The distal valve opener 252 is sized and shaped to push the flaps on the valve in a radially outward direction and part of the flaps in a proximal direction to open a fluid path or flow path 226 through the valve 136. In an example, the leg extensions 196 on the distal valve opener 252 are axially fixed and by pushing the flaps of the valve in a distal direction against the leg extensions, the flaps are deflected radially outward by the leg extensions on the distal side of the valve 136. In other words, when the valve is actuated to open a flow path through the valve, the valve is being physically pushed by an actuator on a proximal side of the valve and an actuator on the distal side of the valve. In a particular embodiment, the valve can be actuated to open a flow path through the valve by being physically pushed by a ring on a proximal side of the valve and leg extensions on the distal side of the valve.

In the valve open position of FIG. 4, the proximal tips 204 of the leg extensions 196 and the distal edge 166 of the ring 150 are spaced from a plane drawn orthogonally to the lengthwise axis of the catheter assembly. In other words, the proximal tips 204 of the leg extensions 196 and the distal edge 166 of the ring 150 do not overlap from the perspective of this plane and a gap is provided between the two to accommodate the valve 136 therebetween. In another example, the proximal tips 204 of the leg extensions 196 and the distal edge 166 of the ring 150 do overlap along an axial direction, which has the effect of deflecting the flaps radially outwards a relatively greater amount than when there is no overlapping. Further, because the flaps are pushed against axially fixed leg extensions 196 on the bushing, the flaps are deflected backwards in the proximal direction by the leg extensions 196. In yet other examples, the proximal tips 204 of the leg extensions 196 and the distal edge 166 of the ring 150 just touch along a plane drawn orthogonally to the lengthwise axis of the catheter assembly.

In a still further aspect of the present disclosure, a catheter assembly is provided comprising a valve, a proximal valve opener, a distal valve opener, a needle hub with a needle, and a catheter hub with a catheter tube. The valve assembly can further include a tip protector for blocking the needle tip in a needle protective position. Following successful venipuncture, a male tip, such as a male Luer, can be inserted into a proximal opening of the catheter hub to advance the proximal valve opener in a distal direction, which moves the valve in a distal direction against the distal valve opener. However, rather than deflecting the flaps in a radially outward and distal direction to open a fluid path through the valve, the flaps are pivoted in a proximal direction to open the fluid path through the valve. For example, the tips of each of the flaps of the valve, which typically originate from a point or origin near a central location of the valve, are deflected in a proximal direction by the leg extensions 196 of the bushing of the present device. In an example, the flaps are deflected in the proximal direction by pushing the flaps against stationary leg extensions 196 on a distal valve opener 252. In other words, the flaps on the valve can be deflected in a proximal direction by a structure located distally of the valve and abutting a distally facing surface of the valve 136. The distal valve opener 252 can be a metal bushing having a body with a cone shaped section having two or more leg extensions extending therefrom in a proximal direction. The bushing may also be made from a thermoplastic material.

To change the male tip 220 or to simply close the valve 136 from the open position of FIG. 4, the male tip 220 is removed in the distal direction away from the catheter hub 102. The biasing or resilient nature of the valve 136, which can be made from an elastomer, allows the valve to recoil to its more relaxed state. Thus, the flaps on the valve will recoil by moving distally while the outer edges or outer sections of the valve body recoil proximally, which pushes the proximal valve opener 250 in the proximal direction and the shoulder 170 on the proximal valve opener 250 towards or against the shoulder 176 inside the interior cavity of the catheter hub. The valve 136 and the proximal valve opener 250 therefore return to substantially the position shown in FIG. 3 after removal of the male tip from the catheter hub.

Alternatively, a coil spring, a leaf spring, or an elastomeric cylinder 276 of a softer material (not shown) than the valve 136 may optionally be placed between the distally facing surface of the valve and an inside distal step or shoulder 274 of the catheter hub 102, which is shown schematically in FIGS. 1-4. This spring or elastomeric cylinder 276, if incorporated, can provide extra biasing force to return the valve 136 to a closed position when the male medical instrument 220 is removed. The resilient component 276, which can be an elastic element, a spring, an O-ring, or other pliable element having resilient or biasing properties, can be spaced from the valve 136 in the ready to use position shown in FIG. 1 or can contact the valve in the ready to use position.

The valve 136 may be opened again by placing a male tip 220 into the proximal opening of the catheter hub 102 and pushing the proximal valve opener 250 in the distal direction, as described above with reference to FIG. 4.

Figure 7:
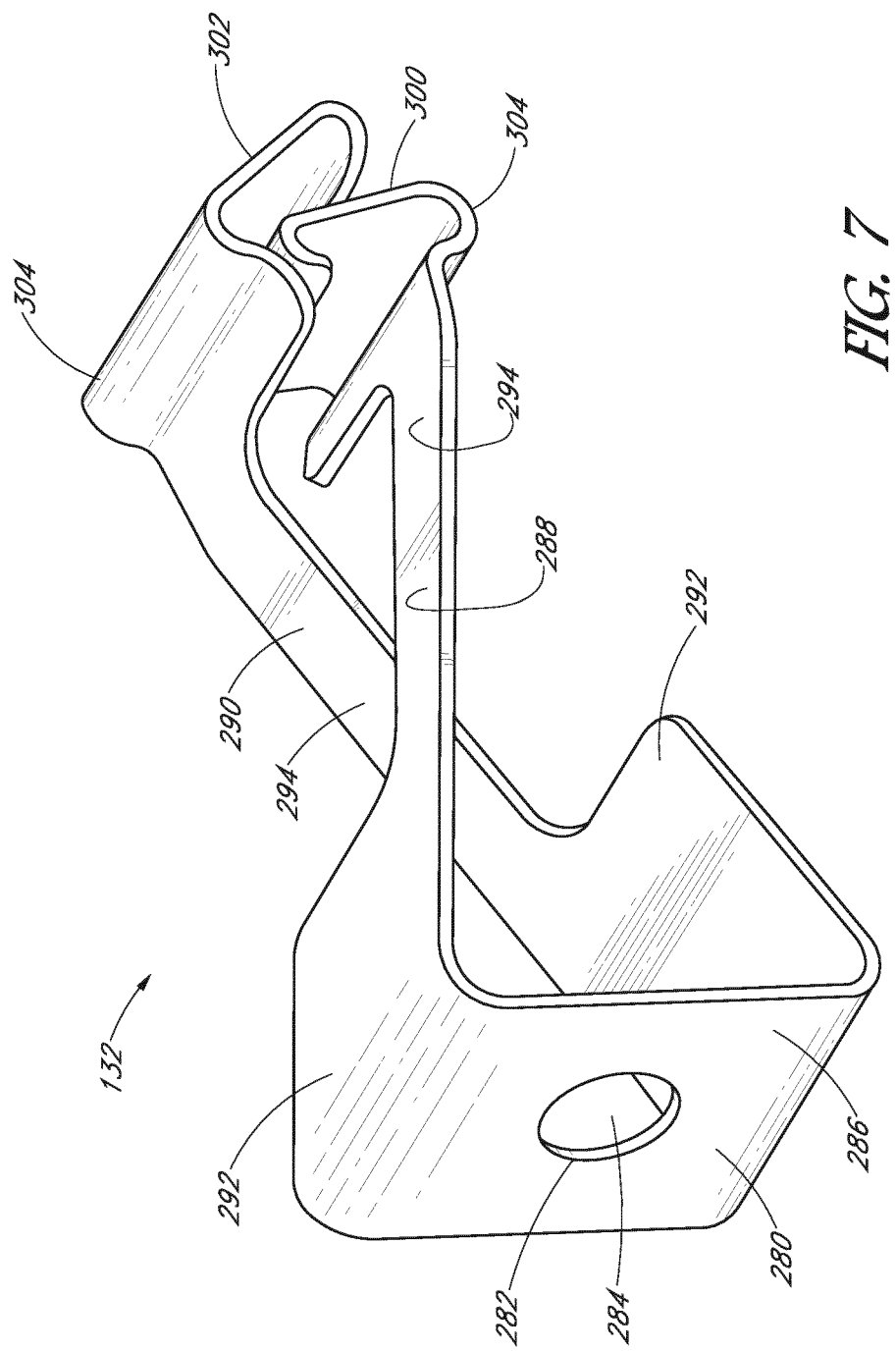
FIG. 7 is an isometric view of the needle guard of FIG. 1.

FIG. 7 is a rear isometric view of the needle guard 132 of FIG. 1. The needle guard 132 is exemplary only as needle guards with other or different features may be used instead of the exact needle guard 132 shown in FIG. 7. In the present embodiment, the needle guard 132 comprises a proximal wall 280 comprising a perimeter 282 defining an opening 284. The proximal wall 280 has a proximally facing wall surface 286 and a distally facing wall surface opposing the proximally facing wall surface. At least one resilient arm 288 extends distally of the proximal wall 280. As shown, two resilient arms 288, 290 extend distally of the proximal wall. One arm can be longer than the other arm. Each arm can also include different arm widths, including a first arm section 292 of a first width and a second arm section 294 of a second width, which is smaller than the first width. The two arms can originate from different ends of the proximal wall 280 and can cross one another at their respective second arm sections 294. Thus, when viewed from a side along the lengthwise direction of the needle guard 132, the two arms intersect one another. When used with a needle, the two arms 288, 290 intersect one another when in a ready to use position and when in the protective position. In an alternative embodiment, the two arms 288, 290 originate from different ends of the proximal wall and extend in a distal direction without crossing one another. Thus, the two arms 288, 290 can also have essentially the same arm width along the length of each respective arm.

A distal wall 300, 302 is provided at an end of each arm 288, 290. The distal walls 300, 302 can overlap one another along an axial direction of the needle guard by utilizing different arm lengths and/or angling one of the walls at an elbow 304 between the distal wall and the resilient arm. In an example, the elbow 304 of each arm, if two arms are utilized, can engage a corresponding guard engagement section 210 inside the catheter hub 102 to removably secure the needle guard to the catheter hub in the ready position and during the transition process of removing the needle 108 from the catheter hub 102. The needle guard 132 may be folded from a stamped metal sheet to form the guard as shown. Ribs may be formed on the arms, the proximal wall, and/or the distal walls to increase structurally rigidity.

With reference now to FIG. 8A, a front view of an exemplary valve 136 provided in accordance with aspects of the present disclosure is shown, which may be usable with the catheter assemblies and hubs with a female Luer described elsewhere herein. The valve 136 is shown with a valve body 320 having a valve disc 137 having a width measured from one edge to another edge of the perimeter 322 of the valve body, or between a proximally facing surface 319 and a distally facing surface 323. The width of the valve body in the present embodiment is the same as the diameter of the valve body because of the circular configuration of the exemplary valve. The valve body 320 has a thickness, which is the dimension that extends into the page of FIG. 8A or orthogonal to the width. The valve 136 is shown with a single slit 324 formed through the thickness of the valve body 320, which defines a first flap 326*a* and a second flap 326*b*. The first flap 326*a* and the second flap 326*b* can be deflected to open a flow path 226 through the valve body 320. The first flap and the second flap can be deflected by pushing the valve 136 with a valve opener on a proximal side of the valve into leg extensions on a distal side of the valve, as previously discussed.

FIG. 8B is a front view of an exemplary valve 136 provided in accordance with further aspects of the present disclosure, which may be usable with the catheter assemblies and hubs with a female Luer described elsewhere herein. The present valve 136 is similar to the valve of FIG. 8A with a few exceptions. In the present embodiment, three slits 324 are provided through the thickness of the valve body to form three flaps 326*a*, 326*b*, 326*c*. The three slits 324 can intersect at a single central point 328. The first flap 326a and the second flap 326b can be deflected to open a flow path 226 through the valve body 320. The first, second and third flaps 326a, 326b, 326c can be deflected by pushing the valve 136 with a valve opener on a proximal side of the valve into leg extensions on a distal side of the valve, as previously discussed. A fluid flow path 226 is provided when the three flaps are deflected. In an example, the flaps 326a, 326b, 326c near the central point 328 expand radially towards the perimeter 322 and in the proximal direction when deflected by leg extensions on the distal side of the valve 136. As there are three flaps 326a, 326b, 326c, the present valve is configured to be used with a bushing having at least three leg extensions, as shown in FIGS. 6C and 6D.

FIG. 8C is a front view of an exemplary valve 136 provided in accordance with still further aspects of the present disclosure, which may be usable with the catheter assemblies and hubs with a female Luer described elsewhere herein. The present valve 136 is similar to the valve of FIG. 8A with a few exceptions. In the present embodiment, the single slit 324 for forming a first flap 326a and a second flap 328b is provided with reliefs 340, 340 at both ends of the slit 324. In an example, the reliefs 340, 340 embody two short through cuts 340a, 340b at each end of the slit 324 forming a V-shaped relief 340. The two reliefs 340 and 340 provide clearance for the two flaps 326a, 326b to enable them to deflect more readily when pushed against the leg extensions with fewer restrictions at points near the two ends of the slit 324 when no reliefs are incorporated. Less preferably, a single short through cut may be incorporated at each end of the slit 324.

FIG. 9 is an exploded perspective view of a needle assembly or catheter assembly 400 in accordance to further aspects of the present disclosure. The catheter assembly 400, which may more broadly be referred to as a needle assembly or a needle device, is shown comprising a catheter hub 102 with a catheter tube 104 having a distal opening 112, and a bushing 138 with a distal valve opener 252. The bushing 138 can be configured to wedge the proximal end of the catheter tube 104 against the interior wall surfaces of the catheter hub 102 to retain the catheter tube 104 to the catheter hub 102.

Interiorly of the catheter hub, a septum or valve 136, a valve actuator 134, such a proximal valve actuator, and a safety clip 132, such as a needle guard or tip protector, are provided. A needle 108 can be inserted through the proximal opening of the catheter hub, with the needle tip protruding out the distal opening 112 of the catheter tube 104. A cannula hub or needle hub 106 can interconnect with the proximal end of the needle 108 and contact the catheter hub 102 in a ready to use position. The proximal opening of the catheter hub 102 is sized and shaped to receive a male medical implement, such as a male Luer tip.

The tip protector 132 is configured to be removed with the needle 108 following use and the valve 136 and valve actuator 134 remain with the catheter hub 102 for controlling fluid flow therethrough, as previously discussed. The actuator 134 is configured to be pushed into the valve 136 to open the valve for fluid flow, as further discussed below.

A flash back plug 114 can be provided at the proximal end 118 of the needle hub 106, which allows air to vent but stops blood from spilling out the proximal end 118 when entering the flashback chamber 116 during primary flashback. Alternatively, a syringe can be attached to the proximal end of the needle hub. The valve and actuator described further below can also be placed within the needle hub as a second valve. The needle hub 106 can comprise a shoulder or other surfaces to physically contact the catheter hub 102, such as the proximal end surface of the catheter hub, to axially register the two hubs 102, 106 to set the length of the needle tip 110 projecting out of the distal opening 112 of the catheter tube 104.

A protective cap 124 with a sleeve 124a and a saddle 124b can be provided to cover the needle 108 during packaging and before use, which is conventional. The saddle 124b can surround at least part of the catheter hub 102 and the needle hub 106 and be removably engaged to the needle hub 106. The cap 124 should be removed from the needle assembly before use. The catheter hub 102 can be provided with a pair of wings to facilitate securement of the catheter hub to a patient following use.

Figure 10A:
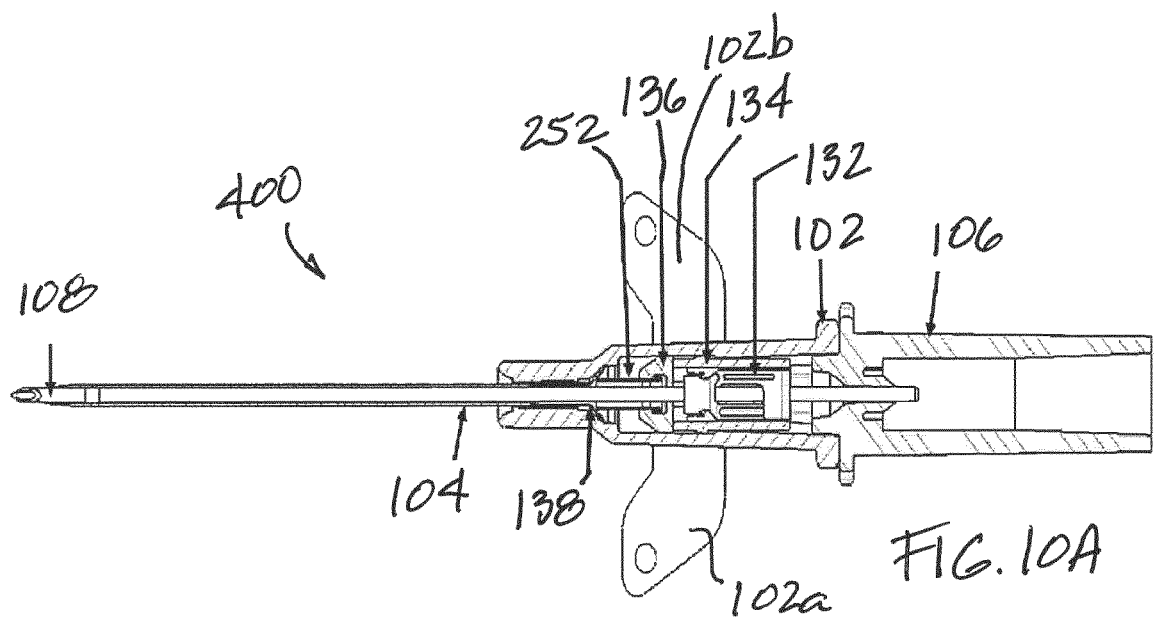
FIG. 10 is a partial cross-sectional side view of the needle assembly of FIG. 9 in an assembled state and FIG. 10A is a top cross-sectional side view of the needle assembly of FIG. 9.
Figure 10:
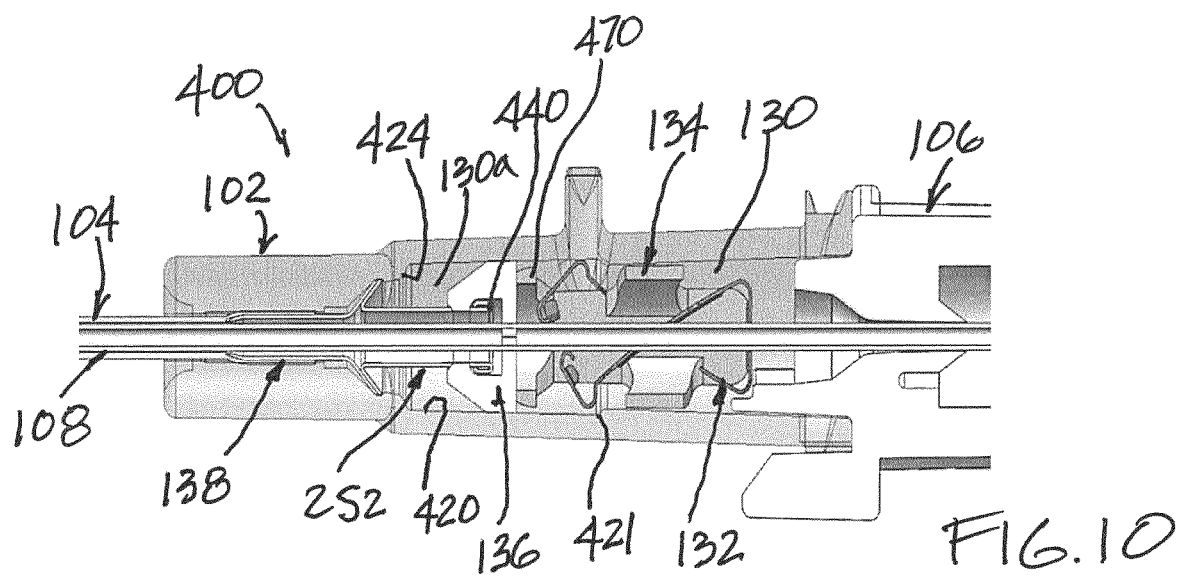

FIG. 10 is a schematic partial cross-sectional side view of the catheter assembly 400 of FIG. 9 in an assembled state and with the protective cap 124 removed. FIG. 10A is a top cross-sectional side view of the catheter assembly 400 of FIG. 9 in an assembled state. The catheter assembly is shown with the catheter hub 102 having a pair of wings 102a, 102b and the catheter tube 104 extending out a distal end thereof and the needle 108 attached to a needle hub 106 and the needle projecting through the catheter hub 102 and the catheter tube 104 in the ready to use position of FIG. 10A, and more closely shown in the partial cut-away view of FIG. 10. The needle 108 also projects through the valve 136, the valve actuator 134, and the needle guard 132 in the ready to use position.

In the ready position with the needle hub 106 registered to the catheter hub 102 and the needle tip extending out the distal end or distal opening 112 (of FIG. 9) of the catheter tube 104, the catheter assembly 100 is ready for use, such as to perform a venipuncture or intravenous access. Sometimes the ready position first requires removing a protective cap 124 (FIG. 9) from the catheter assembly or needle assembly 100.

Located internally of the catheter hub 102 is the valve 136 having a valve disc 410 and a valve skirt 412 (FIG. 21B), the valve disc 410 comprising one or more flaps 326 and one or more slits 324 to be opened by a valve actuator. In an embodiment, the valve skirt 412 is positioned in a recessed section 420 formed in the interior cavity 130 of the catheter hub 102 and is axially slidable along the interior of the catheter hub 102 when actuated to open for fluid flow, as further discussed below. The valve 136 is spaced from a reduced neck section 424 of the catheter hub 102, which anchors the funnel section of the bushing 138 in place. The space between the reduced neck section 424 and the valve skirt of the valve may be referred to as the distal interior cavity 130a.

With reference to FIGS. 21A-21C and continued reference to FIG. 10, in an example, the valve 136 comprises a valve disc 410 comprising a valve outside diameter, a valve thickness measured orthogonal to the valve diameter, and one or more slits 324 formed through the valve thickness defining two or more flaps 326, as previously described with reference to the valve 136 of FIGS. 8A-8C. For example, one or two or three slits 324 may be provided through the thickness of the valve disc to define two, three, or more flaps. In the illustrated embodiment, the valve skirt 412 extends axially of the valve disc 410, forming a generally cylindrical skirt section 430. In some embodiments, the valve skirt 412 may be sloped such that the valve skirt forms a frusto-conical structure 432. The valve skirt 412 forms a distal opening 434 having an area or dimension that is sized and shaped to receive the distal valve opener 252, as further discussed below. A tapered or radiused entrance 434 can be provided at the distal opening 434 to receive the nose 440 of the distal valve actuator 252 to open the valve flaps 326 of the valve disc, as further discussed below.

With further reference to FIG. 21A, the distal opening 434 extends into a distal holding space 441 defined by the valve skirt 412. The holding space 441 is defined by a first interior section 442 having a first internal diameter and a second interior section 444 having a second internal diameter, which is a larger than the first internal diameter. A shoulder 446 is provided at the interface between the first interior section 442 and the second interior section 444. In an example, the shoulder 448 can have a radius.

With reference again to FIG. 10 and continued reference to FIG. 21A, the valve 136 can comprise an outer perimeter that can float inside the interior cavity 130 of the catheter hub 102, between the proximal valve actuator 134 and the bushing 138. For example, the outer perimeter of the valve 136 can move proximally and distally within the interior cavity 130 of the catheter hub 102 and not be restrained, other than perhaps friction or touching, by the catheter hub along an axial direction of the catheter assembly. In an example, the cylindrical portion 430 of the skirt section 412 of the valve is pressed against the interior surface of the interior cavity 130 in a slight interference fit to form a seal therebetween. The generally flat outer contour of the cylindrical portion 430 can allow the valve 136 to move in the axial direction when pushed by the proximal valve actuator 134 while maintaining concentricity with the bore of the catheter hub 102.

In some examples, the outer perimeter of the cylindrical section 430 of the valve 136 can be the same, smaller, or larger than the outer perimeter of the nose section 470 of the proximal valve actuator 134. The relative dimensions between the cylindrical section 430 of the valve and the outer perimeter of the proximal valve actuator 134, such as the nose section 470, can be configured so that the valve actuator 134 can push against the proximally facing surface 456 of the valve disc 410 to axially move the valve 136. Generally speaking, the relative dimensions of the nose section 470 of the valve actuator 134 and the outer perimeter of the cylindrical section 430 are such that the nose section 470 pushes against the proximally facing surface 456 of the valve, when pushed distally by a male medical implement, at a location closer to the outer perimeter of the valve disc 410 than to the center or central portion 458 of the valve disc 410. In contrast, the distal valve actuator 252 is configured to push against the valve disc 410 at a location closer to the center or central portion 458 of the valve disc 410 than to the outer perimeter of the valve disc 410, as further discussed below.

Since the valve 136 can float within the interior 130 of the catheter hub 102, such as move axially along the lengthwise axis of the catheter hub, the valve can be positioned inside a single hub body catheter hub 102. In other words, the valve 136 does not have to be retained inside a catheter hub by two or more catheter hub bodies, such as along a seam of two or more hub bodies. However, the various components described herein may readily be used with a multi-piece catheter hub without deviating from the scope of the present disclosure.

With continued reference to FIG. 10 and to FIG. 18A-18D, the proximal valve actuator 134 comprises a nose section 470, which can be generally cylindrical and terminates in an actuation end 472. The actuation end 472 can have a blunt distal end surface or has a sharp edge. The nose section 470 can have a wall surface with a continuous circumference or continuous perimeter section 580, without a gap or slit, such as a cylinder with a continuous wall. The nose section 470 can define a bore. In some examples, a plurality of spaced apart slits and/or openings can be provided on the nose section 470, away from the continuous perimeter section 580, to permit flow or fluid flushing.

Two actuating elements or plunger elements 152 can extend proximally of the nose section 470. For example, the two plunger elements 152 can be unitarily formed with the nose section 470 and can extend from the nose section in the proximal direction. A gap or space 154 can be provided between the two plunger elements 152 for positioning the needle guard or tip protector 132 therebetween. The gap for positioning the needle guard can be called a holding space 474. The two plunger elements 152 can each comprise at least two lengthwise edges and the edges can be spaced from one another. The lengthwise edges of the plunger elements 152 can align with a lengthwise axis of the valve opener.

In an example, a projection 480 extends outwardly from an outer surface 482 of one or both plunger elements 152 (FIGS. 18A-18D). As shown, a projection 480 extends from the outer surface 482 of each plunger element 152. Each projection 480 resembles a ramp surface having a generally flat edge for abutting a shoulder 421 in the recessed section 420 (FIG. 10) of the catheter hub 102 to restrict the valve actuator 134 from moving in the proximal direction. The ramp surface of the projection 480 and the direction of the ramp allows the actuator 134 to be inserted into the interior 130 of the catheter hub 102 from the open end and be seated within the recessed section 420, as further discussed below. Some embodiments of a valve actuator may utilize other shapes for the nose section 470, such as cuboid, rectangular, conical, pyramidal, chamfered or the like.

In an example, the valve actuator or valve opener 134 has a lengthwise axis and the one or more actuating elements 152 extend axially or parallel to the lengthwise axis. In a particular example, two actuating elements 152 are diametrically opposed to one another along the lengthwise axis. In other examples, the actuating elements 152 are not equally space around the periphery of the nose section 470. As shown in FIG. 18C, the two actuating elements 152 define an outer diameter having a dimension that is approximately similar or the same as the diameter of the nose section 470.

In an example, the actuating elements 152 are flexible and deflectable so that when pushed by a male Luer tip, the actuating elements can defect or flex. The actuating elements 152 can be deflectable by selecting a material that has the requisite resilient properties. In other examples, the actuating elements are deflectable by incorporating one or more weakened sections, such as by incorporating a structurally thin section, by incorporating cut-outs, by employing a small cross-section compared to other sections of the same elongated actuating element, or combinations thereof. Alternatively, the actuating elements 152 can be flexible and deflectable by selecting a material that has the requisite resilient properties and by incorporating one or more weakened sections.

In still other examples, each actuating element 152 has more than one different cross-sectional profiles or contour along a length section. For example, an elongated plunger element can have a square profile located adjacent a crescent-shaped profile.

In an example, the actuating elements 152 are rigid and not deflectable or deformable when loaded, such as when pushed, by a male Luer tip. Further, stabilizing elements may be incorporated to increase the rigidity of the two actuating elements 152, as further discussed below. The two actuating elements 152 may each include a cross-sectional profile, at least at a proximal end, that overlaps a push end of a male tip so that the male tip can push the valve actuator into the valve 136, as previously discussed with reference to FIGS. 5C and 5D.

The nose section 470 of the valve actuator 134 can be configured to engage the valve 136 to open the valve disc 410 when an axial force is applied by a male tip to the actuating elements 152 towards the distal end of the catheter assembly 400, such as during the insertion of an IV drip line of a male Luer connector. Generally, the nose section 470 is rigid relative to the more pliable valve 136, which allows the nose section 470, and more specifically the actuation end 472, to actuate the valve 136, such as to deflect the one or more flaps 326 and open the one or more slits 324 on the valve disc 410. The nose section 470 may be made of a non-compressible material, such as metal, a rigid plastic, or a hard elastomer for pushing against and opening the valve.

The illustrated valve actuator embodiment 134 includes a pair of opposed bands or stabilizers 484, 484 (collectively or individually referred to as stabilizer or stabilizers 484) connecting the two actuating elements 152 at a location along the length of the actuating elements that are between the nose section 470 and the proximal most end or end surface 486 of the valve actuator 134. In some examples, the stabilizers 484 can be located at the proximal end of the two actuating elements 152 so that proximal edges of the stabilizers 484 are generally flush with the proximal end surfaces of the actuating elements. The two stabilizer elements 484, 484 can be referred to as a first or upper stabilizer element and a second or lower stabilizer element. One or more holes can be provided with the actuating elements 152 and/or the stabilizer elements 484 for molding purposes, such as for the core pins.

In one embodiment, the stabilizers or stabilizer elements 484 are arc-shaped, forming an arc following the interior profile of the catheter hub 102 and connecting one actuating element 152 to another actuating element 152. The stabilizers or stabilizer elements 484 may form a substantially cylindrical section on the body of the valve actuator, which cylindrical section is spaced apart from the nose section 470 of the valve actuator. In other words, the valve actuator 134 can be elongated and can have sections that are continuous along a radial direction and sections with reliefs or through passages through the wall of the actuator that are not continuous along the radial direction. As used herein, the terms "relief", "opening", and "through passage" can be used interchangeably.

In an example, the stabilizers 484 define a continuous body section 580 (FIG. 18A) along a perimeter or radial direction of the valve actuator 134 that is spaced from a continuous body section of the nose section 470, which is also continuous along a perimeter or radial direction. The two stabilizers or stabilizer elements 484 may be joined together with the two plunger elements 152 to form a ring structure, called a stabilizing ring 490. Optionally, the two stabilizers 484 may be slightly offset and angled from each other, as shown in FIG. 18C. In some embodiments, there may be one, three, or a different number of actuating elements 152 or different number of stabilizers elements 484. In an example, the valve actuator 134, with the stabilizers or stabilizer elements 484 and projections 480, is made from plastic, such as by plastic injection molding.

The stabilizers 484 can help the valve actuator 134 remain centered within the catheter hub 102 while the actuator 134 moves, such as when pushed by a male Luer tip following successful venipuncture. By staying centered, the nose section 470 can be better aligned with the valve disc 410, such as the slits on the valve disc, allowing for smooth actuation of the valve 136. The stabilizers 484, or the stabilizing ring 490, can also provide an engagement, via friction or snug fit, with the interior of the catheter hub 102 to prevent the actuator 134 from sliding in the proximal direction following removal of the male Luer tip.

In one embodiment, the nose section 470 is configured to push against the proximal facing surface 456 (FIG. 21A) of the valve disc 410 and the distal valve opener 252 is configured to push against the distally facing surface 457 of the valve disc 410 to open the slits 324 and deflect the flaps 326. In an example, the nose section 470 of the proximal valve actuator 134 is configured to push against the outer region 460 of the proximal facing surface 456 of the valve disc 410 and the distal valve opener 252, such as the nose section 440 (FIG. 10) of the distal valve actuator 252, is configured to push against the central region 458 of the distally facing surface 457 of the valve disc 410 to open the slits 324 and deflect the flaps 326.

A relief, opening, or through passage 494 is provided between the nose section 470 and the stabilizing ring 490. The two reliefs or through passages 494 provide clearance so that the interior or central part of the valve actuator 134 and the interior surface of the catheter hub 102 can be in open communication. In other words, between the continuous section of the nose section 470, the continuous perimeter section defined by the two stabilizers 444, 444 and the plunger elements 152, i.e., the stabilizing ring 490 (FIGS. 18A-18C), are one or two reliefs, through passages, or openings 494. The nose section 470 can define a bore and the stabilizing ring 490 can define a bore. A needle guard or tip protector 132 located in the holding space 474 of the valve actuator 134 can project from the holding space at least partially through the through passages 494 to either contact the perimeter of the reliefs 494 and/or the interior surface of the catheter hub, as further discussed below.

The stabilizing ring 490 of the valve actuator 134 can have an inside diameter that is smaller than the diameter defined by the diagonal section or elbows 304 of the two arms 288, 290 of the needle guard 132 when the two arms are biased outwardly by the side of the needle shaft in the ready to use position. Thus, during installation of the needle guard 132 into the holding space 474 of the valve actuator 134, the diagonal section or elbows 304 of needle guard 132 can deflect to pass through the stabilizing ring 490 and into the open areas defined by the reliefs 494.

When the tip protector 132 is positioned between the two plunger elements 152, the two distal walls 300, 302 (FIG. 7) of the needle guard 132, more specifically the two diagonal sections or elbows 304, can be located in the reliefs 494 as shown in FIG. 10 and discussed above to engage the guard engagement surface on the interior surface of the catheter hub 102. This allows the needle guard 132 to project from the holding space 474 of the valve actuator 134 through the two reliefs 494 so that one or both elbows 304 engage the guard engagement surface of the catheter hub, such as the shoulder 421 in the recessed section 420 of the catheter hub 102 or other guard engagement surfaces in the catheter hub 102. The needle guard 132 can therefore be retained within the interior of the catheter hub by projecting through the two reliefs 494 in the ready to use position and during retraction of the needle following successful venipuncture until the needle tip moves proximal of the two distal walls on the needle guard, at which time the needle guard 132 can close over the needle tip and be removed with the needle as discussed above with reference to FIG. 3.

With further reference to FIGS. 18A-18D, each stabilizer element 484 has a distal edge or first edge 496a and a proximal edge or second edge 496b. Alternatively to contacting the shoulder 421 of the recessed section 420 of the catheter hub or other guard engagement surface inside the catheter hub 102, the elbows 304 of the needle guard 132 can be spaced from the interior surface of the catheter hub, or spaced from the shoulder 421, and be retained by the perimeters 544 of the two reliefs 494, such as by the distal edges 496a of the two stabilizer elements 484. Thus, the perimeters 544 or distal edge 496a of one or both stabilizer elements 484 can provide the restraining surface to prevent the needle guard 132 from early activation during retraction of the needle, prior to the needle tip moving proximally of the two distal walls 300, 302 of the needle guard 132 (FIG. 7). Thus, the reliefs or through passages 494 of the present valve actuator 134 can function as choke points or restraining points to restrict the needle guard from proximal movement until the needle guard 132 reduces its radial profile, such as following movement of the needle tip proximally of the distal walls 300, 302 of the needle guard. In an example, the perimeters 584 of the through passages 494 can function as choke points for limiting proximal movement of the needle guard until after activation. In a particular example, one or both distal edges 496a of the stabilizer elements 484 can function as choke points. In other examples, a gap between two interior surfaces of the two stabilizer elements 484 define the choke gap for restricting early activation of the needle guard.

In some examples, one or both stabilizer elements 484 can have a slit or a channel, thus dividing the arc-shaped of each stabilizing element into two segments having a gap or a slit between the two segments. Even with a slit on one or both stabilizer elements 484, the stabilizing ring 490, which can be a non-continuous ring, similar to a ring with one or more slots formed through the ring, can still provide the restraining surface to prevent the needle guard 132 from early activation during retraction of the needle, prior to the needle tip moving proximally of the two distal walls 300, 302 (FIG. 7). Further, the two segments of each stabilizer element 484 can provide stability and reinforcement of the two plunger elements 152 on the valve actuator 134.

The restraining surface of each distal edge 496a can be referred to as a restrict point, choke gap, or choke point as noted above since it provides a rigid structure that prevents the needle guard from moving proximally thereof unless or until the needle guard first activates and collapses radially to reduce its radial profile to then slip proximally of the choke point. In an example, one or two elbows 304 (FIG. 7) of the needle guard 132 can be restricted by the choke point from moving in the proximal direction until the one or two elbows of the needle guard deflect to reduce needle guard's radial profile. In an example, when the radial profile of the needle guard is reduced, the needle guard can slip through the bore defined by the stabilizing ring 490, from a distal position of the stabilizing ring to a proximal position of the stabilizing ring.

The valve opener 134 can be made from a metal material or from a plastic material. When made from a metal material, the valve opener 134 can be formed by bending or deep draw methods and the arc shape cross section of the actuating element 152 can provide added rigidity when pushed by the male Luer. When made from a metal material, such as one of the actuators of FIGS. 19A-19D and 20A-20B, the stabilizer elements 484 can each be made from two stabilizer segments having a slit or a slot between the two segments. When utilizing stabilizing segments, the stabilizing ring formed thereby can be non-continuous.

Each actuating element 152 can comprise at least two lengthwise edges and a rib can be provided along one or both of the lengthwise edges of the actuating element to further add structural rigidity. One or more gaps can be provided between any two actuating elements 152. The one or more gaps can provide clearance or space for fluid flow flowing thereacross, such as during flushing blood or IV infusion. A gap between the actuating elements 152 can define a holding space 474 to accommodate a tip protector 132, as further discussed below.

Figure 11:
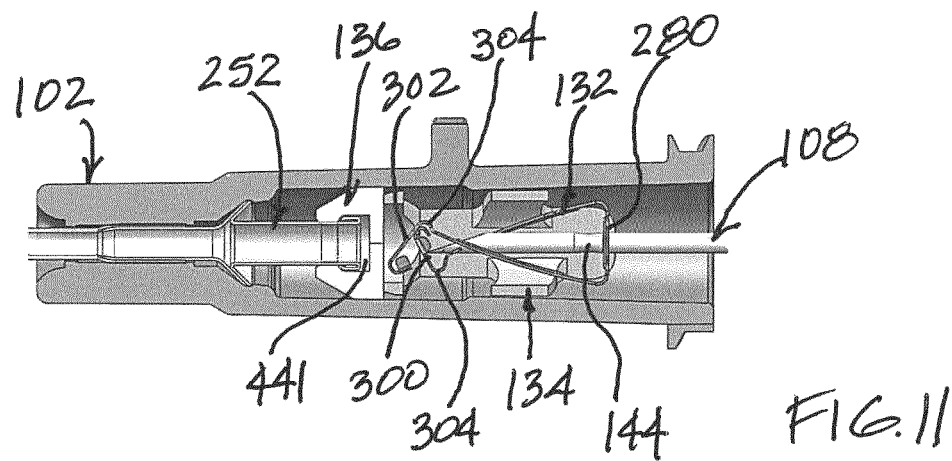
FIG. 11 is a partial cross-sectional side view of the needle assembly of FIG. 10 with the needle being retracted from the catheter hub.
Figure 12:
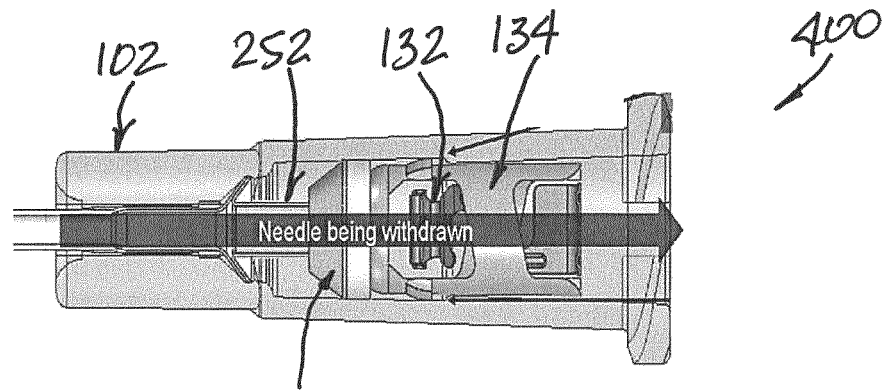
FIG. 12 is a partial cross-sectional side view of the needle assembly of FIG. 11 rotated 90 degrees.

In some embodiments, a majority or most if not all of the tip protector 132 fits within a holding space 474 (FIG. 18A-18D) formed by the body of the actuator 134, between the two plunger elements 152, in the ready to use position, as shown in FIGS. 10 and 11. This allows the catheter hub 102 to be more compact, as less longitudinal space is needed within the hub to fit both the actuator 134 and the tip protector 132 serially lengthwise or when the two only partially overlap in the axial direction. In FIGS. 11 and 12, the tip protector 132 is shown fitting completely within the holding space 474 of the actuator 134 to further reduce the needed space or length in the catheter hub 102. As shown, the proximal wall 280 of the needle guard 132 is generally flush or even with the proximal end surfaces 486 of the two plunger elements 152. In other examples, the proximal wall 280 of the needle guard 132 can locate distally of the proximal end surfaces 486 or proximally of the proximal end surfaces.

When the tip protector 132 only engages with the distal edge 446a of the relief or through passage 494 in the actuator, then no deformity or change of diameter is required on the inside wall of the catheter hub 102 and the tip protector 132 can be placed further proximally in the female Luer taper section of the catheter hub while complying with the international Luer standard for conical fittings and the overall length of the catheter hub 102 can be reduced accordingly.

With reference now to FIG. 15 in addition to FIG. 10, the distal valve actuator or opener 252 of the present embodiment comprises a base 510, a leg extension 512 and a proximal tip or nose section 440. The base 510 can be sized with an outward tapering feature to mate with the funnel section of the bushing 138. In an example, the base 510 is sized to have a contact fit with the funnel section of the bushing 138. For example, the base 510 can contact the proximally facing surface of the funnel section of the bushing 138. The base 510 can have a rim 514 for wedging against the reduced neck section 424 at the distal interior cavity 130a of the catheter hub. As shown, the reduced neck section 424 blocks the rim 514 of the base 510 from displacing in the proximal direction.

In an example, the distal valve actuator 252 can be formed by deep draw methods, allowing the base 510 to be flared from a proximal end of a cylindrical tube or structure. The leg extension 512 can be elongated and extends in the proximal direction of the base 510 and terminates in a nose section or proximal tip 440. In an example, the leg extension 512 is generally cylindrical and defines a bore 518. The wall 520 defining the bore 518 can be continuous along the circumference. In some examples, slits or slots may be provided in or through the wall 520 of the leg extension 512 for fluid flow thereacross, such as for flushing. When slits or slots are incorporated, the distal valve opener or actuator 252 can have two or more leg extensions 512, each with a nose section or proximal tip.

In an example, the proximal end of the leg extension 512 is folded to form a folded section 522, similar to a hemmed pants. The folded section 522 therefore includes two wall layers 520 and a rounded proximal edge 524 formed by folding a surface on itself, which can be called a folded edge. A shoulder 526 is provided at the interface between the leg extension 512 and the nose section 440.

As shown in FIG. 10, the nose section 440 of the distal valve actuator 252 projects into the distal holding space 441 (FIG. 21A) of the valve 136 in the ready to use position with the rounded proximal edge 524 either in contact with the distally facing surface 457 of the valve disc 410 or spaced from the distally facing surface 457. In an example, the interior diameter of the first interior section 442 of the valve 136 contacts the exterior surface of the wall 520. In a particular example, the interior diameter of the first interior section 442 grips the exterior surface of the wall 520 of the leg extension 512. A seal can be provided between the first interior section 442 of the valve and the exterior surface of the wall 520 of the distal actuator 252. The seal can be a fluid tight seal. The tension or interference provided by the first interior section 442 gripping the exterior of the wall 520 can be adjusted by selecting the inside diameter of the first interior section, the material type for the seal, which can be made from a poly-isoprene or any suitable bio-compatible elastic material, the durometer of the molded seal, and/or the length of the first interior section 442. In an alternative embodiment, there is no seal between the first interior section 442 and the exterior wall 520.

In the ready to use position of FIG. 10, the shoulder 526 at the nose section 440 of the distal valve actuator 252 is located distally of the shoulder 446 located between the first interior section 442 and the second interior section 444 of the distal holding space 441 of the valve 136. In an example, the folded section 522, which has a larger diameter than the diameter of the leg extension 512, is located in the second interior section 444. The wall 520 of the leg extension 512 can contact the first interior section 442 when the folded section 522 is located in the second interior section 444. The shoulder 526 of the distal valve actuator 252 can contact or be spaced from the shoulder 446 inside the distal holding space 441 in the ready to use position.

FIG. 11 shows the needle assembly 400 of FIG. 10 during retraction of the needle 108 following intravenous access. As shown, the needle tip 110 has moved proximally of the two distal walls 300, 302 of the needle guard thereby removing the bias between the needle and the two arms 288, 290 of the needle guard (FIG. 7). The two arms 288, 290 and the two distal walls 300, 302 move radially to reduce the radial profile of the needle guard 132. For example, the distance between the two elbows 304 of the needle guard 132 decreases between the position of FIG. 10 and the position of FIG. 11 when the two distal walls 300, 302 are no longer biased by the needle to decrease the radial profile of the needle guard 132. The radial profile at the elbows 304 are now smaller than the choke points defined by the two distal edges 496*a* of the stabilizing ring 490 of the proximal valve actuator 134. Further, because the proximal wall 280 on the needle guard 132 remains the same, a needle guard section distal of the stabilizing ring 490 is smaller in radial dimension than the radial dimension of the proximal wall 280 located proximal of the stabilizing ring 490.

As the needle 108 further moves in the proximal direction, the change in profile 144 on the needle engages the proximal wall 280 of the needle guard 132 to remove the needle guard from the catheter hub with the needle, as previously discussed. In an example, proximal movement of the needle 108 moves the distal walls 300, 302 and the two elbows 304 of the needle guard 132 through the bore defined by the stabilizing ring 490 of the proximal valve actuator 134 and out the proximal opening of the catheter hub 102.

In an example, the valve 136 closes upon removal of the needle 108 from the valve disc 410, as shown in FIG. 11. In some examples, there may or may not be a slight gap or leakage of fluid through the slits 324 when the valve closes as shown. However, leakage, if any, is minimal and a practitioner is allotted ample time to prepare the catheter hub 102 for fluid transfer without risking fluid flow out the open proximal end of the catheter hub when the valve closes. In an example, blood flashback from a patient can accumulate at the distal holding space 441 of the valve 136. As a fluid tight seal can be provided between the leg extension 512 of the distal valve actuator 252 and the first interior section 442 of the valve 136, the distal interior cavity 130*a* of the catheter hub 102 can remain relatively free of any blood flashback.

FIG. 12 is similar to FIG. 11 with the viewing angle rotated 90 degrees. As shown, the two elbows 304 of the needle guard are recessed into holding space 474 of the proximal valve actuator 134, moving from the reliefs 494 radially inwardly into the holding space 474 upon movement of the needle tip 110 proximally of the two distal walls 300, 302 of the needle guard 132.

Figure 13:
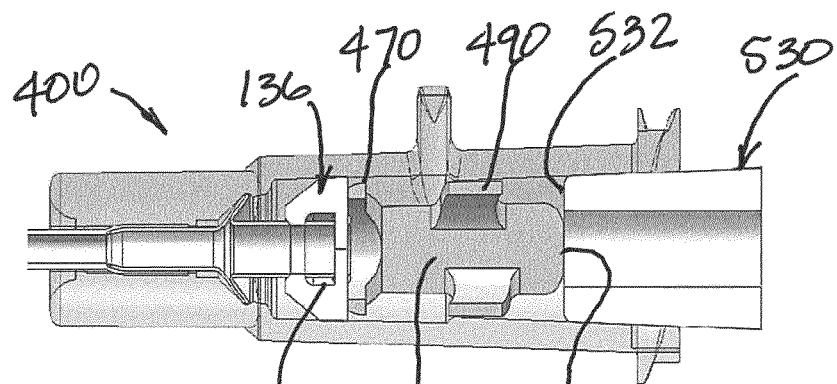
FIG. 13 is a partial cross-sectional side view of the needle assembly of FIG. 10 with the needle removed from the catheter hub and a male medical tip inserted into the proximal opening of the catheter hub.

FIG. 13 is a partial cross-sectional side view of the needle assembly 400 of FIG. 10 with the needle and needle hub completely removed from the catheter hub 102 and a male medical implement 530 is inserted in the proximal opening of the catheter hub 102. The male medical implement 530 can be a male Luer tip of a syringe or an IV tubing adapter. As shown, the distal end 532 of the male tip 530 contacts the proximal end surface 486 of the proximal valve actuator 134 but the male Luer of the tip and female Luer of the catheter hub have not seat or register with one another. In other words, the male Luer tip 530 can still advance further distally into the catheter hub 102 from the position of FIG. 13 to push the valve disc 410 of the valve 136 into the distal valve opener 252.

Figure 14:
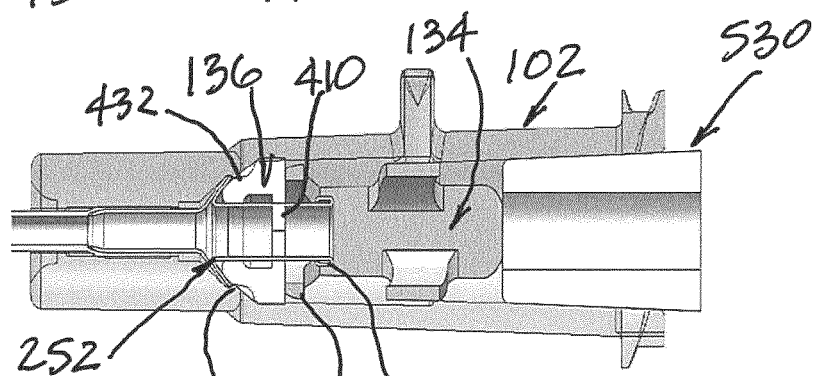
FIG. 14 is a partial cross-sectional side view of the needle assembly of FIG. 13 with the needle removed from the catheter hub and a male medical tip pushing a valve actuator into the valve to open fluid flow through the valve.

FIG. 14 is similar to FIG. 13 but with the male medical implement 530 fully inserted into the proximal opening of the catheter hub 102 and advancing the proximal valve opener 134 distally forward to push the valve axially distally forward further against the distal valve opener 252. In an example, the stabilizing ring 490 provides a bearing surface or support for the proximal valve actuator 134 as the actuator moves. The nose section 470 of the actuator 134 pushes against the outer periphery of the proximally facing surface 456 of the valve disc 410 to axially move the valve 136. As shown, the cylindrical section 430 of the valve skirt 412 slides axially against the interior surface of the interior cavity 130. In an example, the valve skirt 412 is pushed distally until the frusto-conical section 432 of the valve skirt 412 contacts the reduced neck section 424 of the catheter hub 102. In another example, the registering of the two Luer surfaces stops the male tip 530 from moving the valve skirt into contact with the reduced neck section 424.

In an example, when the valve 136 is moved distally by the proximal valve opener 134, the valve disc 410 slides over the leg extension 512 and the nose section 440 of the distal valve opener 252 and the distal valve opener 252 penetrates through the slits 324 and deflecting the flaps 326 (FIGS. 21A and 21C). In an example, the flaps 326 deflect radially and proximally when actuated. That is, whereas the valve skirt 412 and the valve disc 410 move distally forward when actuated by the proximal valve opener 134, which is moved distally forward by a male Luer tip 530, the flaps 326 of the valve disc 410 are deflected radially and proximally, opposite to the direction of movement of the valve skirt 412. In an example, part of the two or more flaps 326 of the valve are situated between the nose section 470 of the proximal valve opener 134 and the leg extension 512 of the distal valve opener 252 when the valve is actuated by both the proximal and distal valve actuators. In some examples, part of the two or more flaps 326 of the valve 136 are situated between the nose section 470 of the proximal valve opener 134 and the nose section 440 of the distal valve opener 252 when the valve is actuated by both the proximal and distal valve actuators.

In an example, the needle device 400 has a one-time valve actuation mechanism or one-time use since the valve 136 does not return to its closed position, similar to the position of FIG. 11 or 13, upon removal of the male Luer tip 530. In some examples, the proximal valve actuator 134 similarly does not return to its non-actuating position, as shown in FIGS. 10 and 11, when the male Luer tip 530 is removed. As shown, when the valve 136 is actuated, the nose section 440 of the distal valve actuator 252 moves a penetrating distance into the valve and proximally of the valve disc 410 such that friction and other constraints prevents their separation.

In an alternative embodiment, the nose section 440 of the distal valve actuator 252 can be configured so that when the valve disc 410 is pushed into the nose section 440 of the distal valve actuator 252 during activation, the actuation or activation end 524 of the distal actuator does not extend too far proximally of a plane defined by the valve disc 410 of the valve 136. This configuration can ensure that the valve 136 is pushed back in the proximal direction by the flaps 326 as the flaps return to their more relaxed state when the male Luer implement 530 is removed. A conical configuration at the nose section 440 of the distal valve actuator 252 can be such a configuration, which maintains an axial directed force vector that is greater than a perpendicular force vector. The angle of the cone can be designed to provide the necessary force vectors when the distal actuator 252 has reached its maximum proximal movement and its minimum proximal movement. The difference between the maximum movement and minimum movement of a standard Luer connector is approximately 2.5 millimeters. Thus, current and future ISO standards for a male standard Luer connector can be consulted or considered in designing the angle of the cone of the actuator to ensure separation between the valve and the distal valve actuator.

Alternatively or additionally, a resilient element, such as a spring or an elastic element or ring, can be incorporated at the distal cavity chamber 130a of the catheter hub 102 to increase the re-coil or returning forces of the valve 132 to facilitate pushing the valve 136 and the proximal valve actuator 134 in the proximal direction and away from the distal valve actuator 252 following removal of the male tip 530 to return to the pre-activated position or valve closed position. The resilient element 276, which can be similar to the elastic element of FIG. 1 or a helical spring, can also help to close the flaps of the valve disc. In this manner, the valve 132 can be re-closed and the proximal valve actuator 134 can return to the proximal position after the initial activation and re-open and so forth, repeatedly. Alternatively or additionally, the flaps 326 can be made thicker to provide sufficient restoring forces without the need for a resilient element 276.

FIG. 16 is a perspective view of a bushing 640 in accordance to further aspects of the present disclosure. The structure of FIG. 16 may also be viewed as a distal actuator in accordance to further aspects of the present disclosure. Yet, the structure of FIG. 16 may be considered a combination bushing and distal actuator 640. As shown, the combination structure 640 of FIG. 16 has a bushing end 642 and an actuator end 644, which can be considered a distal valve opener 644. In an example, the bushing end 642 has a sleeve 648 and a base 650, which can have a funnel shape, for wedging a proximal end of a catheter tube against the interior of a catheter hub 102. The valve actuator end 644 can comprise a base 652, a shoulder 654, a leg extension 512, and a nose section 440, which can be similar to the valve actuator 252 of FIG. 15.

In an example, the combination structure 640 of FIG. 16, which can alternatively be called a bushing or a valve actuator, can be unitarily formed from a metal material, such as by deep draw methods. Alternatively, the combination structure 640 can be formed from two or more separately formed components that are subsequently attached to one another, such as by crimping or welding. When inserted into a catheter hub to secure a catheter tube, as shown in FIG. 17, the base 650 of the bushing end 642 can wedge against a shoulder inside the bore of the nose section 103 and the base 652 of the actuator end 644 can wedge against the internal surface of the bore. In some examples, the leg extension 512 can comprise slits or slots. If incorporated, the distal valve actuator or opener 644 can have two or more leg extensions each with a nose section or proximal actuating tip.

FIG. 17 is a partial cross-sectional side view of a needle assembly having the combination structure 640 of FIG. 16, shown without a needle for clarity. As shown, the bushing end 642 secures a catheter tube 104 to the nose section 103 of the catheter hub 102 and the actuator end 644 projects into a distal holding space 441 of the valve 136, similar to embodiments described above, such as with reference to FIGS. 10 and 11. Also shown is a needle guard 132 and a proximal valve opener 134, similar to that of FIGS. 10 and 11. A needle hub 106 is shown in contact with the catheter hub 102 but shown without a needle for clarity, which if shown would project out the distal end of the needle hub and through the catheter hub 102, the proximal valve actuator 134, the valve 136, the combination structure 640, and the catheter tube 104.

With reference now to FIGS. 18A and 18C, a perspective view and a top or plan view of a valve opener or actuator 134 are shown. The valve opener 134 can be used with any needle assembly described elsewhere herein, such as shown in FIGS. 10-14 and 17. As shown, the valve actuator 134 has a nose section 470 defining a bore and an actuating end 472. Two plunger elements 152 extend proximally of the nose section 470. The nose section 470 defines a first continuous perimeter section 580. Other locations of the nose section 470, away from the first continuous perimeter section 580, can comprise a slit or a slot.

Two stabilizer elements 484, 484 are attached to the two plunger elements 152 to form a stabilizing ring 490, as previously discussed. The stabilizing ring 490 defines a second continuous perimeter section 582 of the valve actuator and has a bore. Each stabilizer element 484 can comprise two edges 496a, 496b. In an example, the two edges 496a, 496b of each stabilizer element can be parallel to one another. As shown, the two stabilizer elements 484 are skewed or slanted so that while two edges 496a, 496b of each stabilizer element can be parallel to one another, the two edges 496a, 496b from one stabilizer element are not parallel to the two edges 496a, 496b of the other stabilizer element. As shown, the proximal edges 496b of the two stabilizer elements 484 are offset along an axial direction or lengthwise direction of the valve actuator. As shown, the distal edges 496a of the two stabilizer elements 484, 484 are offset along an axial direction.

Two reliefs or two through passages 494 are provided on the valve opener 134, each defined or bounded by the first continuous perimeter section 580, the two plunger elements 152, and the stabilizing ring 490. The two reliefs or through passages 494 may be referred to as a first relief or first through passage and a second relief or second through passage. In an example, each relief or through passage has a perimeter 584. In an example, each perimeter 584 can be defined by the structure of the continuous perimeter section 580, the two plunger elements 152, and the respective stabilizer elements 484, 484. As the two stabilizer elements 484, 484 can skew or slant in different directions, the two perimeters 584 of the two reliefs or through passages 494 can be different, such as having different perimeter contours or shapes. As shown, the two perimeters 584 are each defined by a continuous loop. In other words, in the present embodiment, the perimeters 584 do not have a slit or a slot to form an open perimeter. However, where a stabilizer element 484 includes a slot or a slit, the perimeter can be an open perimeter or a non-continuous perimeter.

In some examples, the two stabilizer elements 484, 484 can extend laterally without skewing or slanting in the distal direction or the proximal direction. When so configured, the edges 496a, 496b of the two stabilizer elements 484, 484 are parallel to one another. Additionally, the four edges 496a, 496b of the two stabilizer elements 484, 484 can be parallel to one another and axially offset. That is, the proximal edge 496b of one stabilizer element can be located more proximally or distally that the proximal edge 496b of the other stabilizer element while the four edges are parallel to one another. One or more holes can be incorporated with the stabilizer elements 484 and/or the plunger elements 152 for manufacturing purposes, such as for core pins.

With continued reference to FIGS. 18A and 18C, two plunger element stubs or extensions 152a are shown extending proximally of the stabilizing ring 490. In an example the two plunger element stubs 152a can extend from the stabilizing ring 490 and axially align with the plunger elements 152 located distally of the stabilizing ring 490. In other examples, the two plunger element stubs 152a are not axially aligned with the two plunger elements 152 located distally of the stabilizing ring 490. In still other examples, only one plunger element stub 152a aligns with one of the two plunger elements 152. For a valve opener or actuator with only one plunger element 152 between the first and second continuous perimeter sections, only one of the two plunger element stubs 152a or none of the plunger element stubs can align with the one plunger element.

In some examples, there can be more than two plunger element stubs or extensions 152a extending proximally of the stabilizing ring 490. The two or more plunger element stubs or extensions 152a can be equally spaced around the proximal periphery of the stabilizing ring 490 or randomly spaced around the proximal periphery of the stabilizing ring 490. The plunger element stubs can extend the overall length of a valve actuator. The number of plunger element stubs and/or the arc-curve of each plunger element stub, which defines a width of each plunger element stub, can provide a greater overlapping surface with a male Luer tip than fewer numbers or for a plunger element stub with a relatively smaller arc-curve.

With still further reference to FIG. 18C, the two plunger elements 152 are each shown with a projection 480 on an outside surface 482 of each plunger element 152. As previously described, the two projections 482 can be located inside a recessed section 420 (FIG. 10) of the catheter hub 102 so that a shoulder 421 at a proximal end of the recessed section 420 can provide a stop surface to prevent dislodgement of the valve opener 134 in the proximal direction. In some examples, only one projection 480 is employed on one of the two plunger elements 152 to prevent dislodgement of the valve opener 134 in the proximal direction. The projection 480 can be formed by adding material to the plunger element during injection molding at the site of the projection.

With reference now to FIGS. 18B and 18D, which is a side view and a cross-sectional view of the valve opener 134 of FIG. 18C taken along lines 18D-18D, a holding space 474 is shown, which can be located between two plunger elements 152, inside the stabilizing ring 490, between two plunger element stubs 152a, or combinations thereof. As previously described, part or all of a needle guard or tip protector 132 can be located in the holding space 474 in a ready to use position and one or two elbows 304 of the tip protector 132 (FIG. 7) can project out the relief(s) 494.

A proximal wall 280 (FIG. 7) of a needle guard 132 can be flush with the proximal end surface 486 of a plunger element stub 152a, located proximally of the end surface 486, or located distally of the end surface 486. If no plunger element stub is incorporated, a proximal wall of a needle guard 132 can be flush with the proximal edge of one or both stabilizer elements 484, 484, located proximally of the proximal edge of one or both stabilizer elements 484, 484, or located distally of the proximal edge of one or both stabilizer elements 484, 484.

With still further reference to FIG. 18D, the distance between the two inside surfaces 586 of the two stabilizer elements 484, 484 define a choke gap, choke point, or restricting point for a needle guard to limit proximal movement of the needle guard in a ready to use position and/or during retraction of the needle following intravenous access, as previously discussed. That is, before the needle tip moves proximally of one or two distal blocking walls of a needle guard, the choke point or gap is too small for the needle guard to pass proximally of the choke point or restricting point. However, after the needle tip moves proximally of one or two distal blocking walls of the needle guard, the two distal walls move radially inwardly to decrease the needle guard's radial profile, which is smaller than the choke point. At that point, with a smaller radial profile measured at the two elbows of the needle guard, the needle guard can move proximally of the choke point.

With reference now to FIGS. 19A and 19B, a perspective view and a side view of a valve opener or actuator 700 in accordance to an alternative aspect of the present disclosure is shown. The valve opener 700 can be used with any of the needle assemblies disclosed elsewhere herein, as a proximal valve opener spaced from a bushing 138. As shown, the valve actuator 700 has a nose section 470 defining a bore and two plunger elements 152 extending proximally of the nose section 470. An actuation end is located at a distal end of the nose section. The nose section 470 defines a first continuous perimeter section 580. Other locations of the nose section 470, away from the first continuous perimeter section 580, can comprise a slit or a slot.

Two stabilizer elements 484, 484 are attached to the two plunger elements 152 to form a stabilizing ring 490. Each stabilizer element 484 can comprise two edges 496a, 496b, which can be referred to as a distal edge 496a and a proximal edge 466b. In an example, the two edges 496a, 496b of each stabilizer element are parallel to one another. The two edges 496a, 496b from one stabilizer element 484 are also parallel to the two edges 496a, 496b of the other stabilizer element. As shown, the proximal edges 496b of the two stabilizer elements 484, 484 are aligned along an axial direction or lengthwise direction of the valve actuator. As shown, the distal edges 496a of the two stabilizer elements 484, 484 are also aligned along an axial direction. In other examples, the edges of the two stabilizer elements 484 can be offset axially. In some examples, rather than a single stabilizer element 484, two stabilizer segments having a slit or slot therebetween can be used.

Two reliefs or two through passages 494 can be provided on the valve opener 700, each defined or bounded by the continuous perimeter section 580, the two plunger elements 152, and the respective stabilizer elements 484, 484. The two reliefs or through passages 494 may be referred to as a first relief or first through passage and a second relief or second through passage. In an example, each relief or through passage has a perimeter 584. In an example, each perimeter 584 can be defined by the structure of the continuous perimeter section 580, the two plunger elements 152, and the respective stabilizer element 484. The two perimeters 584 of the two reliefs or through passages 494 can be the same, as shown, or can have different perimeter contours or shapes.

The valve opener 700 of the present embodiment can be made from a metal material. For example, a stamped metal sheet, such as a stamped stainless steel sheet, can be cold worked using deep draw methods to form the shape shown. The various openings or gaps can be punched or stamped and then cold worked to form the disclosed shaped. Each plunger element 152 comprises at least two lengthwise edges and a rib can be provided along one or both of the lengthwise edges to further add structural rigidity. One or more gaps 154 can be provided between any two plunger elements 152. The gaps 154 can provide clearance or space for fluid flow flowing thereacross, such as during IV infusion. The gap 154 can also be utilized to accommodate a needle guard 132, as shown in FIGS. 1 and 10.

FIG. 19C is a top view of the actuator of FIG. 19B, which has rotated 90 degrees. Two plunger element stubs or extensions 152a are shown extending proximally of the stabilizing ring 490. In an example the two plunger element stubs 152a can extend from the stabilizing ring 490 and axially align with the plunger elements 152 located distally of the stabilizing ring 490. In other examples, the two plunger element stubs 152a are not axially aligned with the two plunger elements 152 located distally of the stabilizing ring 490. In still other examples, only one plunger element stub 152a aligns with one of the two plunger elements 152.

In some examples, the valve opener 700 terminates at the stabilizing ring 490 and the actuator is without any plunger element stubs 152a. In still other examples, each plunger element stub 152a located proximally of each plunger element can be considered part of the same plunger element and the stabilizer elements 484 extend radially from the two lengthwise edges of the two plunger elements 152 at a location distal of the proximal surface 486.

In some examples, there can be more than two plunger element stubs or extensions 152a extending proximally of the stabilizing ring 490. The two or more plunger element stubs or extensions 152a can be equally spaced around the proximal periphery of the stabilizing ring 490 or randomly spaced around the proximal periphery of the stabilizing ring 490. The plunger element stubs can extend the overall length of a valve actuator 700. The number of plunger element stubs and/or the arc-curve of each plunger element stub, which defines a width of each plunger element stub, can provide a greater overlapping surface with a male Luer tip than fewer numbers or for a plunger element stub with a relatively smaller arc-curve. In some examples, the plunger elements stubs 152a have curved profiles that can resemble that of the plunger elements of FIGS. 5C and 5D, wherein the concave and convex surfaces of the plunger elements can face in either direction, inwards or outwards relative to the lengthwise axis of the valve actuator.

With still further reference to FIG. 19C, the two plunger elements 152 each comprises a projection 480 on an outside surface 482 of each plunger element. As previously described, the two projections 480 can be located inside a recessed section 420 (FIG. 10) of a catheter hub so that a shoulder 421 at a proximal end of the recessed section 420 can provide a stop surface to prevent dislodgement of the valve opener 700 in the proximal direction. In some examples, only one projection 480 is employed on one of the two plunger elements 152 to prevent dislodgement of the valve opener 700 in the proximal direction. In an example, each projection 480 can be formed by cold-working a surface of the stamped metal sheet at the respective plunger element to push out a protruding surface.

With reference now to FIG. 19D, which is a cross-sectional side view of the valve opener 134 of FIG. 19C taken along lines 19D-19D, the nose section 470 is shown necked down with two radiused sections 702 into the plunger elements 152. Each plunger element 152 extends in the proximal direction with a generally constant width and then necks up with a second set of radiused sections 704, which transition into the stabilizer segments 484. A recessed surface 710 forming one of the projections 480 is shown on the plunger element 152.

Another pair of radiused sections 706 are located proximally of the stabilizer segments 484 to form the plunger element stubs 152a. The plunger elements 152 and the plunger element stubs 152a both have two spaced apart lengthwise edges, which can be provided with ribs to add strength to the respective structure. From about within the stabilizing ring 490 and extending in a proximal direction, each plunger element stub 152a can bulge outwardly with an outward bulging portion 714 relative to the lengthwise axis to form curved surfaces along the cross-section of each stub 152a. The bulging portion 714 can also be formed inwardly to form an inward bulging portion. This feature can be included to form the concave and convex surfaces for the plunger element stubs, as previously discussed with reference to FIGS. 5C and 5D.

With continued reference to FIGS. 19C and 19D, a holding space 474 is shown, which can be between two plunger elements 152, inside the stabilizing ring 490, between two plunger element stubs 152a, or combinations thereof. As previously described, part or all of a needle guard or tip protector 132 (FIG. 7) can be located in the holding space 474 in a ready to use position and one or two elbows 304 of the tip protector 132 can project out the reliefs 494.

A proximal wall of a needle guard 132 (FIG. 7) can be flush with the proximal end surface 486 of a plunger element stub 152a, located proximally of the end surface 486, or located distally of the end surface 486. If no plunger element stub is incorporated, a proximal wall of a needle guard 132 can be flush with the proximal edge 496b of one or both stabilizer elements 484, located proximally of the proximal edge 496b of one or both stabilizer elements 484, or located distally of the proximal edge 496b of one or both stabilizer elements 484.

With still further reference to FIG. 19D, the distance between the two inside surfaces 486 of the two stabilizer elements 484, 484 define a restricting point, a choke gap or a choke point for a needle guard to limit proximal movement of the needle guard in a ready to use position and/or during retraction of the needle following intravenous access, as previously discussed. That is, before the needle tip moves proximally of one or two distal blocking walls 300, 302 of a needle guard 132 (FIG. 7), the choke point or gap is too small for the needle guard to pass proximally of the choke point. However, after the needle tip moves proximally of one or two distal blocking walls of the needle guard, the two distal walls move radially inwardly to decrease the needle guard's radial profile, which is smaller than the choke point. At that point, with a smaller radial profile measured at two elbows 304 (FIG. 7), the needle guard can move proximally of the choke point.

FIG. 20A is a perspective view of a proximal valve opener or actuator 760 provided in accordance to further aspects of the present disclosure. FIG. 20B is an end view of the valve actuator 760 of FIG. 20A, looking at the nose section 470. The valve actuator 760 is usable with any of the needle devices discussed elsewhere herein, such as the needle device of FIGS. 1 and 10.

The present valve actuator 760 is similar to the valve actuator of FIGS. 19A-19C with a few exceptions. In the present embodiment, the nose section 470 is formed by folding a wall layer to produce a folded section 762, similar to the nose section 440 of the distal actuator 252 of FIG. 15. The end surface 764 of the folded layer terminates roughly between the nose section 470 and the stabilizing ring 490. In an example, the end surface 764 is located closer to the stabilizing ring 490 than the nose section 470 but the final location is not so limited. In an example, the end surface 764 defines a shoulder 766 on each of the two plunger elements 152. The two shoulders 766 can provide similar functions as the projections 480 on the valve actuator 700 of FIGS. 19A-19D.

In an example, cut-outs or notches 780 can be provided at the folded edge 782 of the nose section 470. Optionally, the notches 780 can be omitted. The notches 780 can be provided to permit flow-through, such as for flushing and reducing or eliminating fluid stagnation. In an example, eight equally spaced apart notches 780 can be provided at the folded edge 782. In other examples, fewer or more than eight notches 780 can be provided and the notches can be randomly spaced along the folded edge 782.

FIGS. 21A-21C show different views of a seal 136 in accordance with aspects of the present disclosure. FIG. 21A shows a cross-sectional side view of the valve. FIG. 21B shows a perspective view of the valve. FIG. 21C is a front view of the valve, looking at the valve skirt 412 and the opening 434 at the distal end of the valve skirt.

Methods of making and of using the catheter assemblies and their components described elsewhere herein are within the scope of the present disclosure.

Although limited embodiments of catheter assemblies and their components have been specifically described and illustrated herein, many modifications and variations will be apparent to those skilled in the art. For example the needle guard may be of one piece or can be integrated from more than one piece, such as from multiple pieces. Furthermore, it is understood and contemplated that features specifically discussed for one catheter assembly or for one component may be adopted for inclusion with another catheter assembly or another component, provided the functions are compatible. Accordingly, it is to be understood that the catheter assemblies and their components constructed according to principles of the disclosed devices, systems, and methods may be embodied other than as specifically described herein. The valve and valve opener described herein can also be used with a needle hub by locating them inside a female Luer taper of the needle hub. The valve and valve opener can also be used in the female connector of an infusion needle or a blood collection device or a central venous catheter or peripherally inserted central catheter (PICC). In other words, the valve and valve opener can be used in any medical device intended for infusion or bodily fluid collection with a female Luer housing or hub. The disclosure is also defined in the following claims.

What is claimed is:

1. A needle assembly comprising:
    a needle hub with a needle extending from a distal end of the needle hub;
    a catheter tube attached to a catheter hub and having the needle extending through the catheter tube in a ready to use position;
    a valve positioned in an interior cavity of the catheter hub, said valve comprising an outer perimeter that axially floats when moved by a proximal valve opener, which is also positioned in the interior cavity of the catheter hub and proximal of the valve;
    a distal valve opener comprising a leg extension extending in a proximal direction of a base of a bushing, which is located distally of the valve; and
    a needle guard comprising a proximal wall with an opening having the needle passing therethrough located, at least in part, in a holding space of the proximal valve opener.

2. The needle assembly of claim 1, wherein the leg extension of the distal valve opener is axially fixed inside the interior cavity of the catheter hub.

3. The needle assembly of claim 1, wherein the valve comprises three slits and three flaps and wherein the distal valve opener comprises three spaced apart leg extensions.

4. The needle assembly of claim 3, wherein the three leg extensions are aligned with the three flaps.

5. The needle assembly of claim 1, wherein the proximal valve opener has a nose section sized for abutting contact with a proximally facing surface of the valve.

6. The needle assembly of claim 1, wherein the proximal valve opener has two reliefs, openings or through passages and wherein the needle guard has two elbows, one each extending at least partly through a respective relief, opening or through passage.

7. The needle assembly of claim 1, wherein the proximal valve opener has a first continuous perimeter section spaced from a second continuous perimeter section.

8. The needle assembly of claim 1, wherein the valve comprises a skirt section extending distally of a valve disc.

9. The needle assembly of claim 1, wherein the base of the bushing and the leg extension are unitarily formed.

10. The needle assembly of claim 1, wherein the proximal valve opener comprises two stabilizer elements connecting two plunger elements and wherein a gap between the two stabilizer elements define a choke point for limiting proximal movement of the needle guard.

11. A method of manufacturing a needle assembly comprising:
    providing a catheter hub with a catheter tube with a distal opening, said catheter hub comprising a hub body defining an interior cavity and a proximal opening;
    positioning a bushing inside the catheter hub and against the catheter tube and positioning a valve proximal of the bushing and proximal of a leg extension, which has a nose section for abutting a distally facing surface of the valve; the valve being axially displaceable inside the interior cavity of the catheter hub along an axial direction of the catheter hub and comprises two or more flaps;

positioning a proximal valve opener proximal of the valve and inside the interior cavity of the catheter hub;

placing a needle, which is attached to a needle hub, through the catheter hub, the valve, and the catheter tube so that a tip of the needle extends out the distal opening of the catheter tube; and positioning a needle guard comprising a proximal wall with an opening having the needle passing therethrough located, at least in part, in a holding space of the proximal valve opener.

12. The method of claim 11, further comprising placing an elbow of the needle guard through a relief, opening or through passage of the proximal valve opener.

13. The method of claim 11, wherein the leg extension is unitarily formed with the bushing.

14. The method of claim 11, wherein the proximal valve opener has a nose section sized for abutting contact with a proximally facing surface of the valve.

15. The method of claim 11, wherein the proximal valve opener has a first continuous perimeter section spaced from a second continuous perimeter section.

16. The method of claim 11, wherein the proximal valve opener comprises two stabilizer elements connecting two plunger elements and wherein a gap between the two stabilizer elements define a choke point for limiting proximal movement of the needle guard.

17. A catheter assembly comprising:
a needle hub with a needle having a needle tip extending from a distal end of the needle hub;
a catheter tube attached to a catheter hub and having the needle extending through the catheter tube in a ready to use position;
a valve comprising a valve disc positioned in an interior cavity of the catheter hub,
a first valve opener positioned distally of the valve disc;
a second valve opener positioned proximally of the valve disc; and
a needle guard comprising a proximal wall with an opening having the needle passing therethrough, said needle guard configured to cover said needle tip in a protective position.

* * * * *